United States Patent
Hall et al.

(10) Patent No.: US 12,233,051 B2
(45) Date of Patent: *Feb. 25, 2025

(54) TREATING PRIMARY OR IDIOPATHIC HYPEROXALURIA WITH SMALL MOLECULE INHIBITORS OF LACTATE DEHYDROGENASE

(71) Applicants: VANDERBILT UNIVERSITY, Nashville, TN (US); The UAB Research Foundation, Birmingham, AL (US); The United States of America, as Represented by the Secretary, Department of Health and Human Services, Bethesda, MD (US)

(72) Inventors: Matthew Hall, Damestown, MD (US); Daniel J. Urban, Poolesville, MD (US); John Knight, Birmingham, AL (US); Ross Holmes, Birmingham, AL (US); Kyle David Wood, Birmingham, AL (US); Alex Waterson, Birmingham, AL (US); Victor M. Darley-Usmar, Birmingham, AL (US); Leonard M. Neckers, Bethesda, MD (US)

(73) Assignees: VANDERBILT UNIVERSITY, Nashville, TN (US); THE UAB RESEARCH FOUNDATION, Nashville, TN (US); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/352,721

(22) Filed: Jul. 14, 2023

(65) Prior Publication Data
US 2023/0372308 A1    Nov. 23, 2023

Related U.S. Application Data

(63) Continuation of application No. 17/322,260, filed on May 17, 2021, now Pat. No. 11,752,138.

(60) Provisional application No. 63/026,296, filed on May 18, 2020.

(51) Int. Cl.
A61K 31/427    (2006.01)
A61K 31/4439   (2006.01)
A61K 31/506    (2006.01)

(52) U.S. Cl.
CPC ........ *A61K 31/427* (2013.01); *A61K 31/4439* (2013.01); *A61K 31/506* (2013.01)

(58) Field of Classification Search
CPC .......................... A61K 31/427; A61K 31/4439
See application file for complete search history.

(56) References Cited

U.S. PATENT DOCUMENTS

| | | |
|---|---|---|
| 10,351,532 B2 | 7/2019 | Maloney et al. |
| 10,954,228 B2 | 3/2021 | Maloney et al. |
| 10,961,200 B2 | 3/2021 | Maloney et al. |

*Primary Examiner* — Kamal A Saeed
(74) *Attorney, Agent, or Firm* — CANTOR COLBURN LLP

(57) ABSTRACT

The disclosure provides methods of treating a patient having primary hyperoxaluria or idiopathic hyperoxaluria comprising administering a therapeutically effective amount of compound of the formula

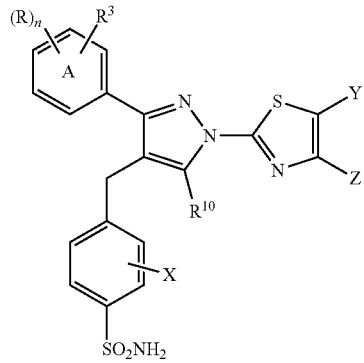

and pharmaceutically acceptable salts, solvates, and hydrates thereof to the patient. The variables, e.g. ring A, n, R, $R^3$, $R^{10}$, X, Y, and Z are defined herein. These compounds act as lactate dehydrogenase inhibitors and are useful inhibiting the conversion of glyoxylate to oxalate. When administered to a patient having a disease or disorder associated with elevated oxalate levels, such as PH type 1, type 2, or type 3 or idiopathic hyperoxaluria the compounds prevent or substantially reduce the amount and buildup of oxalate the patient's kidneys, bladder, urinary tract and other parts of the patient's body.

19 Claims, 2 Drawing Sheets

TREATING PRIMARY OR IDIOPATHIC HYPEROXALURIA WITH SMALL MOLECULE INHIBITORS OF LACTATE DEHYDROGENASE

CROSS REFERENCE TO RELATED APPLICATIONS

This application is a continuation of U.S. application Ser. No. 17/322,260, filed May 17, 2021, which claims priority to U.S. Provisional Appl. No. 63/026,296, filed May 18, 2020, both of which are hereby incorporated by reference in their entirety.

BACKGROUND

Primary hyperoxalurias (PHs) are rare autosomal recessive disorders caused by the overproduction of oxalate, leading to recurrent calcium oxalate kidney stone disease and, in some cases, end-stage renal disease. PH type 1 is an autosomal recessive disease caused by mutations in the gene encoding alanine-glycolate aminotransferase (AGXT), an enzyme responsible for converting glyoxylate to glycine. The excess glyoxylate is converted to oxalate which, if not excreted, damages the kidneys, liver, and other organs. PH 1 symptoms can be severe and are often apparent a few months after birth; median onset of symptoms is at 5-6 years. Patients with PH type 1 usually develop kidney stones and urinary tract stones. PH type 1 causes accumulation of oxalate elsewhere in the body, including in bone, skin, retinas, and myocardium. Left untreated, PH type 1 causes kidney failure and end-stage renal disease, which are often fatal.

PH type 2 is an inherited autosomal recessive disorder caused by mutations in the gene for the glyoxylate reductase/hydroxypyruvate reductase (GPHPR) enzyme. GPHPR is the enzyme responsible for converting excess glyoxylate to glycolate. Lack of GPHPR enzyme function leads to an excess of glyoxylate and buildup of oxalate. PH type 2 causes symptoms similar to those of PH type 1, though symptoms are usually less severe, and patients are often not afflicted until mid-life.

PH type 3 is an inherited autosomal recessive disorder caused by mutations in the gene for 4-hydroxy-2-oxoglutarate aldolase 1 (HOGA1). Few cases of this disorder have been diagnosed. PH type 3 also causes a buildup of oxalate. About 50% of PH type 3 patients develop kidney stones before the age of 5. However, the symptoms of this disorder may lessen in adolescence.

Liver-kidney and isolated kidney transplantation are the treatment of choice in primary hyperoxaluria type 1 and type 2, respectively. Lactate dehydrogenase (LDH) is a key enzyme responsible for the conversion of glyoxylate to oxalate. One promising strategy to treat PHs is to reduce the production of oxalate by diminishing the activity of LDH. The use of oral small molecule LDH inhibitors can potentially remove the need for liver and kidney transplants in these patients, remove calcium oxalate deposits, prevent kidney and liver damage, and thus improve length and quality of life for PH patients.

Kidney stone formers on metabolic workup may have hyperoxaluria (as defined by 24 hour urinary parameters with urine oxalate >40 mg/day). These stone formers, whether they represent idiopathic calcium oxalate stone formers or undefined (non-PH 1/2/3 primary hyperoxaluria) stone formers, may benefit from treatment with oxalate lowering agents.

Minimally potent LDHA inhibitors have been known for several years. For example, gossypol is a nonselective inhibitor of LDH that blocks the binding of NADH, with a K, for LDHA and lactate dehydrogenase B (LDHB) of 1.9 and 1.4 µM, respectively (Doherty et al., *J. Clin. Invest.*, 2013, 123(9): 3685-3692). Billiard et al. (*Cancer and Metabolism*, 2013, 1(19): 1-17) reports that certain derivatives of 3-((3-carbamoyl-7-(3,5-dimethylisoxazol-4-yl)-6-methoxyquinolin-4-yl) amino) benzoic acid are potent inhibitors of LDH and were 10- to 80-fold more selective for LDHA inhibition than LDHB inhibition. However, the in vivo bioavailability of theses inhibitors was found to be poor.

The majority of previously reported LDH inhibitors suffer from modest LDH inhibition, poor cellular penetration and poor pharmacokinetic properties, making their application as therapies challenging. Furthermore, the specific requirements of an effective agent for the treatment of hyperoxaluria differs significantly from those required for oncology. Most oncology agents have a systemic tissue distribution profile, ensuring compound can inhibit cancer cells throughout the body. In contrast, with hyperoxaluria, one desires a liver-targeted tissue distribution profile, with improved activity in hepatocytes and little or no cytotoxicity.

In view of the foregoing, there remains a need to provide orally available LDH inhibitors with potency and selectivity for LDH and adequate bioavailability for the treatment of PH.

SUMMARY

This disclosure provides a method of treating primary hyperoxaluria in a patient comprising, administering a therapeutically effective amount of a compound of Formula I or a pharmaceutically acceptable salt, solvate, or hydrate thereof to the patient:

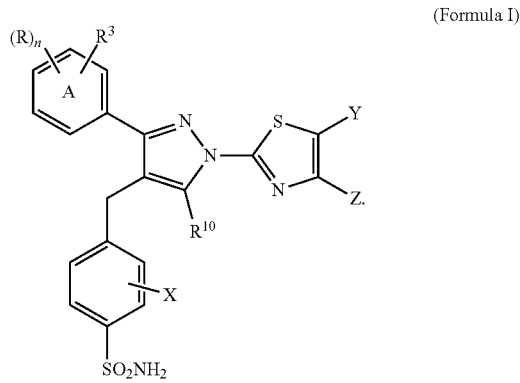

(Formula I)

Within Formula I the variables, e.g. X, Y, Z, R, n, $R^3$, and $R^{10}$ carry the following definitions:

The A ring,

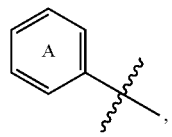

is phenyl or pyridyl.

X is hydrogen or a halogen.

Y is hydrogen or $C_1$-$C_2$alkyl.

Z is —CO$_2$H, —CONH$_2$, —CONH(CN), —CONHSO$_2$CH$_3$, —CONH(OH), —COCF$_3$, CH(OH)CF$_3$, —CH$_2$OH, or —B(OH)$_2$.

n is 0, 1, 2, or 3.

R is independently chosen at each occurrence from halogen, hydroxyl, C$_1$-C$_4$alkyl, and C$_1$-C$_4$ alkoxy.

R$^3$ is a —C(O)CH$_3$, a substituted or unsubstituted phenyl group, a substituted or unsubstituted indanyl group, a substituted or unsubstituted tetrahydronaphthyl group, a substituted or unsubstituted cyclohexenyl group, a substituted or unsubstituted indenyl group, a substituted or unsubstituted 2,6-diazaspiro[3.3]heptanyl group, a substituted or unsubstituted imidazolyl group, a substituted or unsubstituted dihydrofuranyl group, a substituted or unsubstituted pyrrolidinyl group, a substituted or unsubstituted pyridyl group, a substituted or unsubstituted pyrimidinyl group, a substituted or unsubstituted thiazolyl group, a substituted or unsubstituted spiro[2.5]oct-5-enyl, a substituted or unsubstituted benzimidazolyl group.

Or, R$^3$ is -L-Q, wherein L is an C$_2$-C$_4$alkynyl group, an ethylenylene group, a cyclopropylene group, or a cyclobutylene group, and wherein Q is hydrogen, a C$_1$-C$_5$alkyl group, a substituted or unsubstituted C$_3$-C$_6$ cycloalkyl group, or a substituted or unsubstituted five-membered heterocycle having 1 to 3 heteroatoms selected from N, O, and S.

Or, R$^3$ is —NR$^5$C(O)R$^4$, —C(O)NR$^5$R$^6$, wherein R$^4$ is hydrogen, C$_1$-C$_5$alkyl, or substituted or unsubstituted phenyl, and R$^5$ and R$^6$ are each independently hydrogen or C$_1$-C$_5$alkyl, wherein R$^5$ and R$^6$ optionally form a ring, and wherein R$^4$ and R$^5$ optionally form a ring.

R$^{10}$ is hydrogen or (cyclopropyl)C$_0$-C$_4$alkyl, which cyclopropyl is optionally substituted with methyl or cyclopropyl or fused to a cyclopropyl group in spiro orientation, or R$^{10}$ is (cyclopropyl)C$_1$-C$_4$alkyl in which the C$_1$-C$_4$alkyl is substituted with cyclopropyl.

Compound disclosed herein and the pharmaceutically acceptable salts, hydrates and solvates thereof, are useful for treating a disease or disorder associated with elevated oxalate levels. In certain embodiments, the disease or disorder is hyperoxaluria, chronic kidney disease (CKD), end stage renal disease (ESRD) or kidney stone disease. In yet certain embodiments, the disease or disorder is primary hyperoxaluria, idiopathic hyperoxaluria or idiopathic oxalate kidney stone disease.

In another aspect, provided herein are methods of treating a disease or disorder associated with elevated oxalate levels, comprising administering to a subject having such disease or disorder, a therapeutically effective amount of one or more compounds disclosed herein, or a pharmaceutically acceptable salt, hydrate or solvate thereof, or the pharmaceutical compositions disclosed herein. In certain embodiments, the disease or disorder is hyperoxaluria, chronic kidney disease (CKD), end stage renal disease (ESRD) or kidney stone disease. In yet certain embodiments, the disease or disorder is primary hyperoxaluria, idiopathic hyperoxaluria or idiopathic oxalate kidney stone disease. In yet certain embodiments, the disease or disorder is associated with the AGXT, GRHPR or HOGA1 mutation, or a combination of mutations thereof.

The disclosure also includes a method of preventing the symptoms of primary hyperoxaluria or reducing the severity of the symptoms of primary hyperoxaluria in a patient, comprising determining the patient has a mutation in a gene encoding an enzyme, the mutation causing a loss of enzyme function or a reduction in enzyme activity, where the enzyme is selected from:

(a) alanine-glycolate aminotransferase (AGXT);
(b) glyoxylate reductase/hydroxypyruvate reductase (GPHPR); and
(c) 4-hydroxy-2-oxoglutarate aldolase 1 (HOGA1);

and administering a therapeutically effective amount of a compound of Formula I or a pharmaceutically acceptable salt, solvate, or hydrate thereof to the patient.

In addition, this disclosure includes a method of preventing or reducing the symptoms of kidney disease and preventing or reducing stone formation in patients with idiopathic calcium oxalate kidney stone disease or those with currently undefined primary hyperoxaluria.

Compounds and compositions of Formula I have been described previously in U.S. application Ser. Nos. 15/540,893 and 16/313,737, both of which are hereby incorporated by reference in their entirety for their teachings regarding compounds of Formula I and their function as LDH inhibitors.

It has been discovered that a compound of Formula I is effective in inhibiting lactate dehydrogenase A (LDHA) and/or lactate dehydrogenase B (LDHB) activity, thereby making the compound effective in treating primary hyperoxaluria.

This disclosure provides methods of treating primary hyperoxaluria (PH) type 1, type 2, or type 3, as well as idiopathic hyperoxaluria, in a patient comprising administering a compound of Formula I, or salt, solvate, or hydrate thereof to the patient.

DETAILED DESCRIPTION

Figure 1:
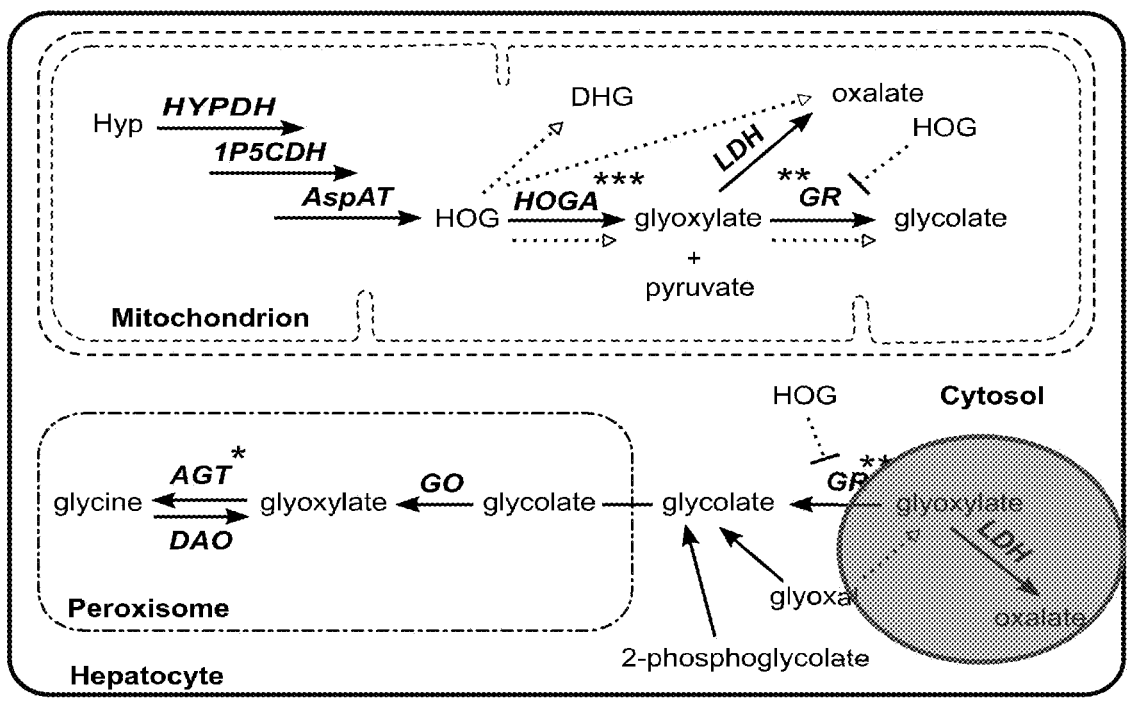
FIG. 1. Glyoxylate detoxification pathway in human hepatocytes. *=PH type 1; =PH type 2; and *=PH type 3.
Figure 2:
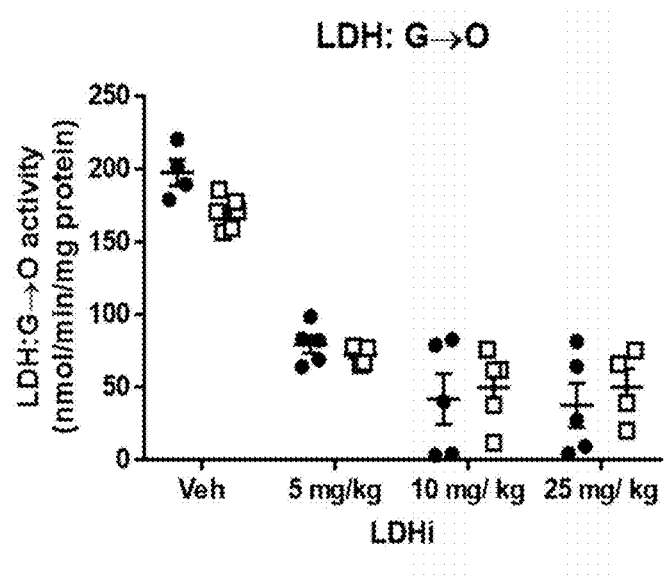
FIG. 2. LDH activity as measured by the rate of conversion of glyoxylate (G) to oxalate (O) in mice livers. Wild type mice, closed circles; AGXT null mice; open squares. Maximal suppression of oxalate production in mice liver was observed with 5-10 mg/kg of inhibitor compound 247, oral daily dose given for 5 days. Liver was harvested from animals two hours after delivery of the last drug dose. Enzyme assays were performed with liver lysates in 0.1M Glycine-Sodium hydroxide buffer, pH 9.6, 20 mM glyoxylate, 3.25 mM NAD+, and the rate of increase in absorbance at 340 nm monitored at room temperature FIG. 3. 24-hr Urinary oxalate (measured as mg oxalate/g creatinine) as a function of LDH inhibitor concentration (mg/kg) in AGXT null mice. A 47-58% reduction in oxalate production was observed with oral dosing of an LDHA inhibitor. Oxalate levels were restored to approximately WT levels with relatively low doses of inhibitor (5-10 mg/kg). Male adults were singly housed in Nalgene metabolic cages and 24 urines collected before (indicated as "0" in graph) and after LDH inhibitor treatment. Mice were fed a purified diet devoid of oxalate to eliminate the contribution of dietary oxalate absorption to urinary oxalate excretion. Urinary creatinine and urinary oxalate were measured by a chemical analyzer and ion chromatography coupled with mass spectrometry, respectively. LDH inhibitor was delivered at 5, 10 or 25 mg/kg daily for 5 days and the mean of the last three days of 24 hour urinary analyte determinations was used to characterize excretions in each mouse.
Figure 3:
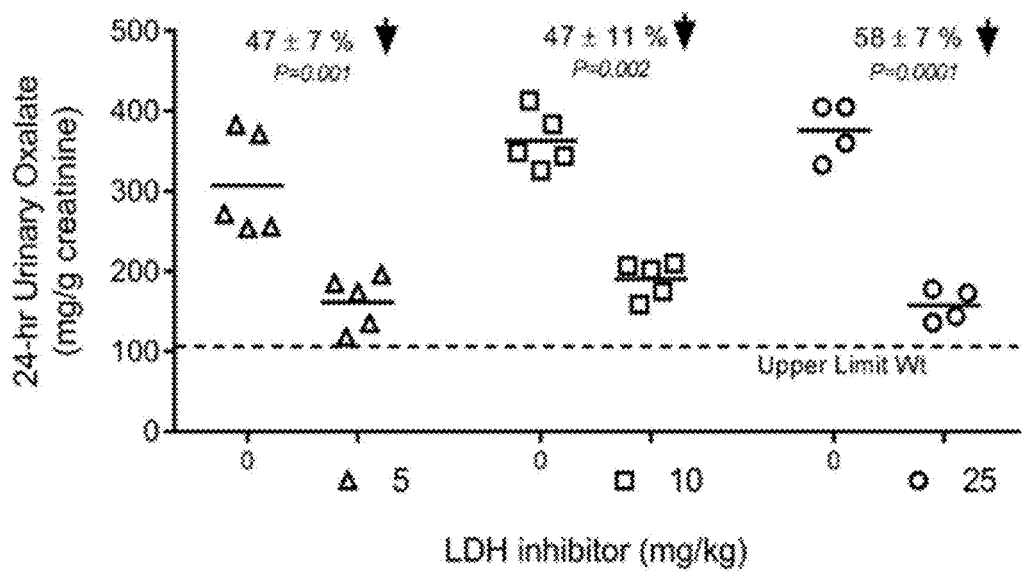

The disclosure includes a method of treating primary hyperoxaluria in a patient comprising administering a compound of Formula I or pharmaceutically acceptable salt, solvate, or hydrate thereof to the patient. The variables in Formula I, e.g. X, Y, Z, R, n, $R^3$, and $R^{10}$, can carry the definitions set forth in the SUMMARY section or may carry any of the definitions set forth herein. Any combination of the variable definitions set for this permitted for a compound of Formula I so long as a stable compound results. The term "compound of Formula I" includes the pharmaceutically acceptable salts, solvates, or hydrates of compounds of Formula I unless clearly contraindicated by the text.

This disclosure also includes compounds of Formula I-A, and pharmaceutically acceptable salts, solvates, or hydrates thereof. With Formula I-A the variables X, Y, Z, R, n, $R^3$, and $R^{10}$, can carry the definitions set forth for Formula I, either in the SUMMARY section or below.

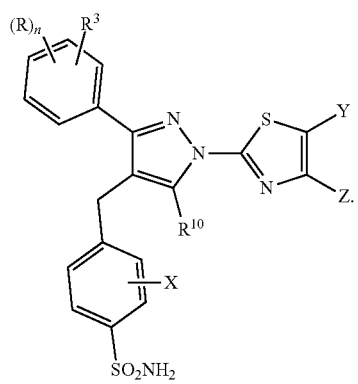

(Formula I-A)

In Formula I, X may be hydrogen, fluorine, or chlorine, and may be in the ortho or meta position (with respect to the point of attachment of the phenyl). The disclosure includes compounds and salts, solvates, and hydrates of Formula I in which X is fluorine and is in the meta position with respect to the point of attachment of the phenyl.

Groups that may substitute $R^3$ include halogen, CHO, $C_1$-$C_6$alkyl, $C_1$-$C_6$alkoxy, mono- and di ($C_1$-$C_4$alkylamine), (cycloalkyl)$C_0$-$C_2$alkyl (e.g. cyclopropyl, cyclopropylmethyl, cyclobutyl), $C_1$-$C_2$haloalkyl, and $C_1$-$C_2$haloalkoxy.

$R^3$ may be a substituted phenyl group, substituted with fluorine, chlorine, a $C_1$-$C_5$alkyl group, —$CF_3$, —$CHF_2$, $CH_3CO$—, $CH_3CO$—, —CN, —$N(CH_3)_2$, or a combination thereof.

$R^3$ may be a -L-Q where L is L is an $C_2$-$C_4$alkynyl group, an ethylenylene group, a cyclopropylene group, or a cyclobutylene group and Q is furanyl, thienyl, oxazolyl, thiazolyl, or 2,3-dihydrofuranyl group, each of which $R^3$ may be unsubstituted or substituted with one or more substituents independently selected at each occurrence from halogen, $C_1$-$C_4$alkyl, and $C_1$-$C_4$alkoxy, trifluoromethyl, difluoromethyl, cyclopropyl, and cyclobutyl.

$R^3$ may be a 1-cyclohexene group substituted with a $C_1$-$C_5$alkyl group, —$CF_3$, or $CH_3O$—.

$R^3$ may be a spiro[2.5]oct-5-enyl group.

$R^3$ is a cis-ethylenylene group or a trans-ethylenylene group.

$R^3$ may be a five-membered heterocycle substituted with fluorine, chlorine, $C_1$-$C_5$alkyl, —$CHF_2$, —$CF_3$, or a combination thereof.

$R^3$ may be a 2,6-diazaspiro[3.3]heptanyl group of the formula

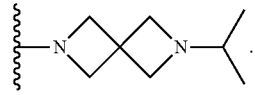

$R^{10}$ may be (cyclopropyl)$CH_2$—.

$R^{10}$ may be hydrogen.

$R^3$ may be -L-Q, where L is an ethynyl group and Q is a five-membered heteroaryl group (such as thienyl, thiazolyl, furanyl, or imidazolyl), which is unsubstituted or substituted with one or more substituents independently chosen from halogen, $C_1$-$C_5$alkyl, $C_1$-$C_5$alkoxy, —$CHF_2$, —$CF_3$, cyclopropyl, and cyclobutyl.

Q may be a five-membered heteroaryl group chosen from thienyl, thiazolyl. oxazolyl, and furanyl, each of which is unsubstituted or substituted with one or more substituents independently chosen from halogen, $C_1$-$C_5$alkyl, $C_1$-$C_5$alkoxy, —$CHF_2$, —$CF_3$, cyclopropyl, and cyclobutyl.

$R^{10}$ may be (cyclopropyl)$CH_2$— or (cyclopropyl)$CH_2CH_2$—.

Y may be hydrogen.

Z may be —COOH, —$CH_2OH$, or —$CONH_2$.

Any of the foregoing definitions of variables for compounds of Formula I may be combined so long as a stable compound results and all such combinations are within the scope of the disclosure.

The methods of this disclosure can include administration of compounds and pharmaceutically acceptable salts, solvates, and hydrates of Formula I in which n is 0; X is fluorine in the meta position; Y is hydrogen; Z is —COOH, —$CH_2OH$, or —$CONH_2$;

$R^3$ is -L-Q, where L is an ethynyl group and Q is a five-membered heteroaryl group chosen from thienyl, thiazolyl. oxazolyl, and furanyl, each of which is unsubstituted or substituted with one or more substituents independently chosen from halogen, $C_1$-$C_5$alkyl, $C_1$-$C_5$alkoxy, —$CHF_2$, —$CF_3$, cyclopropyl, and cyclobutyl; and $R^{10}$ is (cyclopropyl)$C_0$-$C_4$alkyl.

This disclosure also includes method of using compounds of Formula I and salts, solvates, or hydrates thereof to treat hyperoxoaluria in which the following conditions are met:

(i) X is hydrogen or fluoro; Y is hydrogen; and Z is —$CO_2H$.

(ii) $R^{10}$ is (cyclopropyl)$C_0$-$C_2$alkyl.

(iii) The A ring is phenyl; R is halogen and n is 0 or 1; and $R^3$ is phenyl, which is unsubstituted or substituted with one or two substituents independently chosen from halogen, $C_1$-$C_4$alkyl, $C_1$-$C_4$alkoxy, $C_1$-$C_2$haloalkyl, and $C_1$-$C_2$haloalkoxy. (iv) The A ring is phenyl; R is halogen and n is 0 or 1; $R^3$ is -L-Q, wherein L is an ethynyl group; and Q is a 2-thienyl, 2-thiazolyl, or cyclopentyl, each of which is unsubstituted or substituted with 1 or two substituents independently chosen from halogen, $C_1$-$C_4$alkyl, $C_1$-$C_4$alkoxyl, $C_1$-$C_2$haloalkyl, and $C_1$-$C_2$haloalkoxy.

(iv) The A ring is phenyl; R is halogen and n is 0 or 1; $R^3$ is -L-Q, wherein L is an ethynyl group; and Q is a 2-thienyl, 2-thiazolyl, or cyclopentyl, each of which is unsubstituted or substituted with 1 or two substituents independently chosen from halogen, $C_1$-$C_4$alkyl, $C_1$-$C_4$alkoxyl, $C_1$-$C_2$haloalkyl, and $C_1$-$C_2$haloalkoxy.

(v) The A ring is phenyl; R is halogen and n is 0 or 1; and $R^3$ is indenyl, which is unsubstituted.

(vi) The A ring is 2-pyridyl; R is halogen and n is 0 or 1; $R^3$ is -L-Q, wherein L is an ethynyl group; and Q is a 2-thienyl, 2-thiazolyl, or cyclopentyl, each of which is unsubstituted or substituted with 1 or two substituents independently chosen from halogen, $C_1$-$C_4$alkyl, $C_1$-$C_4$alkoxyl, $C_1$-$C_2$haloalkyl, and $C_1$-$C_2$haloalkoxy.

Examples of compounds useful in the methods of this disclosure include:

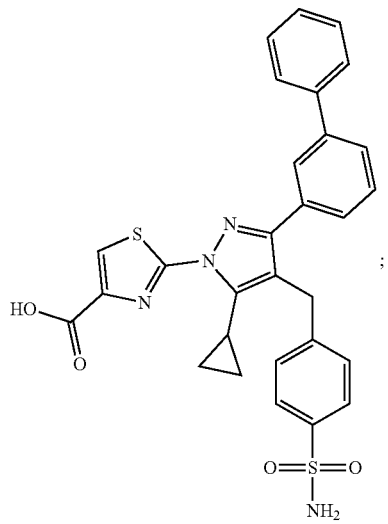

;

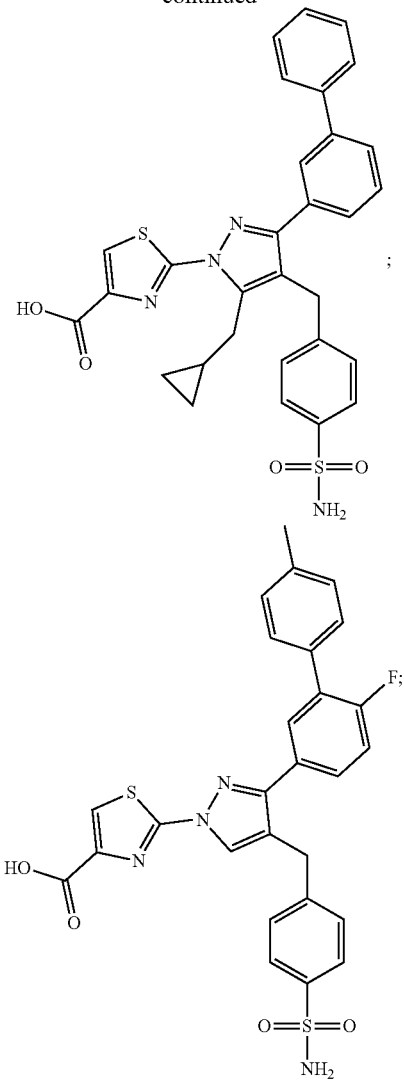

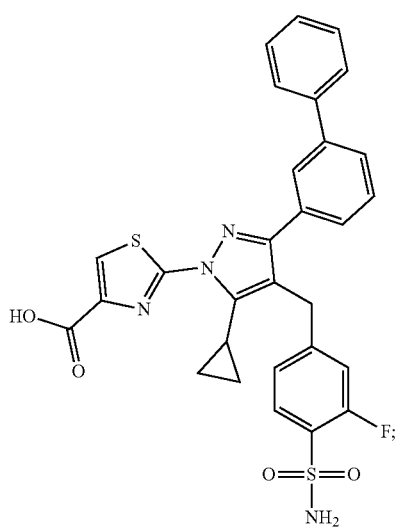

;

This disclosure also includes a method of using compounds of Formula II:

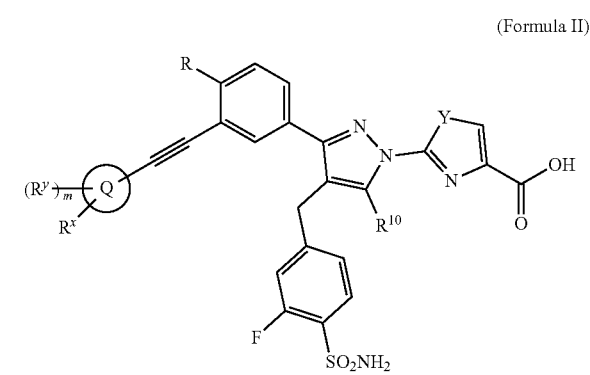

(Formula II)

and salts, solvates, or hydrates thereof, to treat hyperoxaluria, wherein:
Y is O or S;
Q is thienyl;

$R^x$ is halogen, $C_1$-$C_4$alkyl, $CHF_2$, $CF_3$, cyclopropyl or cyclobutyl;
$R^y$ is $C_1$-$C_4$alkyl;
$R^{10}$ is (cyclopropyl)$C_0$-$C_3$alkyl optionally substituted with one or two groups independently selected from methyl and cyclopropyl;
R is hydrogen or fluoro; and
m is 0 or 1.

In certain embodiments, the disclosure herein is to a method of using a compound of Formula II and salts, solvates, and hydrates thereof, to treat hyperoxaluria, wherein Y is O or S; Q is thienyl, RN is halogen, $C_1$-$C_4$alkyl, $CHF_2$ or $CF_3$; $R^y$ is $C_1$-$C_4$alkyl; $R^{10}$ is (cyclopropyl)$C_0$-$C_2$alkyl optionally substituted with one or two groups independently selected from methyl and cyclopropyl; R is hydrogen or fluoro; and m is 0.

In certain embodiments, the disclosure herein is to a method of using a compound of Formula II and salts, solvates, or hydrates thereof, to treat hyperoxaluria, wherein Y is O or S; Q is thienyl, RN is halogen, $C_1$-$C_4$alkyl, $CHF_2$ or $CF_3$; $R^y$ is $C_1$-$C_4$alkyl; $R^{10}$ is (cyclopropyl)$C_0$-$C_2$alkyl optionally substituted with one or two groups independently selected from methyl and cyclopropyl; R is hydrogen or fluoro; and m is 0. In certain embodiments, the disclosure herein is to a method of using a compound of Formula II and salts, solvates, and hydrates thereof, to treat hyperoxaluria, wherein Y is O or S; Q is thienyl, RN is $C_1$-$C_4$alkyl; $R^y$ is $C_1$-$C_4$alkyl; $R^{10}$ is (cyclopropyl)$C_0$-$C_2$alkyl; R is hydrogen or fluoro; and m is 0.

In certain embodiments, the disclosure herein is to a method of using a compound of Formula II and salts, solvates, and hydrates thereof, to treat hyperoxaluria, wherein R is fluoro and the remaining variables of Formula II are as described above. In certain embodiments, the disclosure herein is to a method of using a compound of Formula II and salt solvates, and hydrates thereof, to treat hyperoxaluria, wherein $R^{10}$ is cyclopropylmethyl and the remaining variables of Formula II are as described above. In certain embodiments, the disclosure herein is to a method of using a compound of Formula II and salts, solvates, and hydrates thereof, to treat hyperoxaluria, wherein Y is S and the remaining variables of Formula II are as described above.

This disclosure also includes a method of using compounds of Formula II-A:

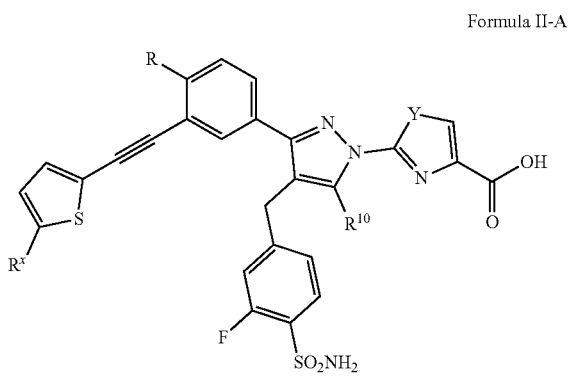

Formula II-A and salts, solvates, and hydrates thereof, to treat hyperoxaluria, wherein:
Y is O or S;
$R^x$ is halogen, $C_1$-$C_4$alkyl, $CHF_2$, $CF_3$, cyclopropyl or cyclobutyl;
$R^{10}$ is (cyclopropyl)$C_0$-$C_3$alkyl optionally substituted with one or two groups independently selected from methyl and cyclopropyl; and
R is hydrogen or fluoro.

In certain embodiments, the disclosure herein is to a method of using a compound of Formula II-A and salts, solvates, and hydrates thereof, to treat hyperoxaluria, wherein Y is O or S; RN is halogen, $C_1$-$C_4$alkyl, $CHF_2$, $CF_3$, cyclopropyl or cyclobutyl; $R^{10}$ is (cyclopropyl)$C_0$-$C_2$alkyl optionally substituted with one or two methyl groups; and R is hydrogen or fluoro.

In certain embodiments, the disclosure herein is to a method of using a compound of Formula II-A and salts, solvates, and hydrates thereof, to treat hyperoxaluria, wherein Y is O or S; RN is halogen, $C_1$-$C_4$alkyl, $CHF_2$ or $CF_3$; $R^{10}$ is (cyclopropyl)$C_0$-$C_2$alkyl; and R is hydrogen or fluoro.

In certain embodiments, the disclosure herein is to a method of using a compound of Formula II-A and salts, solvates, and hydrates thereof, to treat hyperoxaluria, wherein Y is O or S; RN is $C_1$-$C_4$alkyl; $R^{10}$ is (cyclopropyl)$C_1$-$C_3$alkyl; and R is hydrogen or fluoro.

In certain embodiments, the disclosure herein is to a method of using a compound of Formula II-A and salts, solvates, and hydrates thereof, to treat hyperoxaluria, wherein R is fluoro and the remaining variables of Formula II-A are as described above. In certain embodiments, the disclosure herein is to a method of using a compound of Formula II-A and salts, solvates, and hydrates thereof, to treat hyperoxaluria, wherein $R^{10}$ is cyclopropylmethyl and the remaining variables of Formula II are as described above. In certain embodiments, the disclosure herein is to a method of using a compound of Formula II-A and salts, solvates, and hydrates thereof, to treat hyperoxaluria, wherein Y is S and the remaining variables of Formula II-A are as described above.

Formula I includes the following compounds of Table 7, below, and their pharmaceutically acceptable salts, solvates, and hydrates.

Compounds of Formula I are set forth below in Table 7 as representative examples. Ester prodrugs and pharmaceutically acceptable salts, solvates, and hydrates of the exemplified compounds are also included in the disclosure.

Terminology

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or language denoting examples (e.g., "such as") provided herein, is intended merely to better illuminate the invention and does not pose a limitation on the scope of the invention unless otherwise claimed. No language in the specification should be construed as indicating any non-claimed element as essential.

The term "substituted," as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes a heteroaromatic moiety, the resulting molecule can sometimes adopt tautomeric forms. For example, a pyridyl group substituted by oxo at the 2- or 4-position can sometimes be written as a pyridine or hydroxypyridine. Combinations of substituents and/or variables are permissible only if such combinations result in stable compounds or useful synthetic intermediates. A stable compound or stable structure is meant to imply a compound that is sufficiently robust to survive isolation from a reaction mixture and subsequent formulation into an effective therapeutic agent. Unless otherwise specified, substituents are named into the core structure. For example, it is to be understood that aminoalkyl means the point of attachment of this substituent to the core structure is in the alkyl portion and alkylamino means the point of attachment is a bond to the nitrogen of the amino group.

Suitable groups that may be present on a "substituted" or "optionally substituted" position include, but are not limited to, halogen (fluorine, chlorine, bromine, and iodine); cyano; —OH; —CH$_2$F, —CHF$_2$, —CF$_3$, nitro; linear, branched, or cyclic alkyl groups (including cycloalkyl and (cycloalkyl)alkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms, alkanoyl groups having 2 to about 8 carbon atoms. For example, suitable groups that may be present on a "substituted" or "optionally substituted" position include hydroxyl, halogen, —CH$_2$F, —CHF$_2$, —CF$_3$, cyano, alkyl groups, and alkoxy groups. Two geminal alkyl substituents (i.e., two substituents attached to the same carbon atom) may optionally form a ring. Non-limiting examples of such substituted groups are spiro[2.5]octanyl and spiro[2.5]octenyl groups.

In any of the embodiments above, the "alkyl," unless otherwise indicated, is a straight-chain or branched alkyl substituent containing from, for example, from about 1 to about 8 carbon atoms, e.g., from about 1 to about 6 carbon atoms. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs as part of a group, such as, e.g., in $C_3$-$C_6$ cycloalkylalkyl, hydroxyalkyl, haloalkyl (e.g., monohaloalkyl, dihaloalkyl, and trihaloalkyl), cyanoalkyl, aminoalkyl, alkylamino, dialkylamino, arylalkyl, etc. The alkyl can be substituted or unsubstituted, as described herein. Even in instances in which the alkyl is an alkylene chain (e.g., —(CH$_2$)$_n$—), the alkyl group can be substituted or unsubstituted. An example of a substituted alkylene chain includes —CF$_2$-cyclopropyl.

The term "cycloalkyl," as used herein, means a cyclic alkyl group that is fully saturated or partly unsaturated, containing from, for example, 3 to 6 or 7 carbon atoms. Examples of such cycloalkyl groups include saturated cycloalkyl groups such as cyclopropyl, cyclobutyl, cyclopentyl, cyclohexyl, and the like, and unsaturated cycloalkyl groups such as cyclobutene, cyclopentene, and cyclohexene. The cycloalkyl group can be substituted or unsubstituted, as described herein. "Cycloalkyl" also includes multicyclic cycloalkyl groups having up to 10 carbon atoms, which may be fused, bridged, or spiro ring systems.

In any of the embodiments above, the term "hydroxy" refers to the group —OH.

In any of the embodiments above, the term "alkoxy" includes linear or branched alkyl groups, that are attached to a divalent oxygen. The alkyl groups are the same as described herein.

In any of the embodiments above, the term "halo" refers to a halogen selected from fluorine, chlorine, bromine, and iodine.

"Haloalkyl" is an alkyl group as described herein substituted with at least one halogen substituents up to the maximum possible number of halogen substituents. In some embodiments haloalkyl groups have 1 or 2 carbon atoms. Examples of haloalkyl groups include trifluoromethyl, trichloromethyl, trifluoromethyl, dichloromethyl, difluoroethyl (—CH$_2$CHF$_2$), pentafluoromethyl, and the like. "Haloalkoxy" is a haloalkyl group, as described herein, attached to the group it substitutes via a divalent oxygen.

The term "heteroaryl," as used herein and unless otherwise indicated, represents a stable an aromatic 5-, 6- or 7-membered monocyclic- or stable 9- or 10-membered fused bicyclic ring system, which consists of carbon atoms and from one to four, or from one to three, heteroatoms selected from the group consisting of N, O and S wherein the nitrogen and sulfur heteroatoms may optionally be oxidized, and the nitrogen heteroatom may optionally be quaternized. In the case of a "heteroaryl" which is a bicyclic group, the second ring need not comprise a heteroatom and may be fused to a benzene ring. Accordingly, bicyclic "heteroaryl" includes, for example, a stable 5- or 6-membered monocyclic aromatic ring consisting of carbon atoms and from one to four, or from one to three, heteroatoms, as defined immediately above, fused to a benzene ring, or a second monocyclic "heteroaryl," or a "heterocyclyl," a "cycloalkyl," or a "cycloalkenyl," as defined above. Examples of heteroaryl groups include, but are not limited to, benzimidazole, benzopyrazole, benzisothiazole, benzisoxazole, benzofuran, isobenzofuran, benzothiazole, benzothiophene, benzotriazole, benzoxazole, furan, furazan, imidazole, indazole, indole, indolizine, isoquinoline, isothiazole, isoxazole, naphthyridine, oxadiazole, oxazole, phthalazine, pteridine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, benzimidazole, benzothiadiazole, isoindole, pyrrolopyridines, imidazopyridines such as imidazo[1,2-a]pyridine, pyrazolopyridine, pyrrolopyrimidine and N-oxides thereof.

The term "hydrate" as used herein and unless otherwise indicated, refers to a compound provided herein or a salt thereof, that further includes a stoichiometric or non-stoichiometric amount of water bound by non-covalent intermolecular forces.

The term "in vivo" as used herein and unless otherwise indicated, refers to a process or event occurring in a living organism or living system.

The term "calcium oxalate stones" as used herein and unless otherwise indicated, refers to crystalline material comprising calcium oxalate salt present as stones or plaques in the kidney, bladder or urinary tract.

The term "hyperoxaluria" refers to a condition characterized by elevated levels of oxalate in the urine or plasma, or by the presence of kidney stones. In certain embodiments, hyperoxaluria is characterized by urinary oxalate excretion rate of greater than about 0.5 mmol/1.73 m$^2$ per day, greater than about 0.7 mmol/1.73 m$^2$ per day, greater than about 0.8 mmol/1.73 m2, greater than about 1.0 mmol/7.2 m$^2$ per day, greater than about 1.2 mmol/1.73 m$^2$ per day or greater than about 2 mmol/1.73 m$^2$ per day. In certain embodiments, elevated oxalate levels means having an oxalate excretion rate that is greater than normal urinary excretion, which is less than about 0.45 mmol/1.73 m$^2$ per day. In certain embodiments, elevated oxalate levels means having a urinary oxalate excretion rate that is greater than about 40 mg/day. In certain embodiments, elevated oxalate levels means having a urinary oxalate excretion rate that is greater than about 45 mg/day. In certain embodiments, the urinary oxalate excretion rate is about two-fold higher than normal. In certain embodiments, the urinary oxalate excretion rate is about four-fold higher than normal. In yet certain embodiments, hyperoxaluria is characterized by urinary oxalate/creatinine ratio greater than the reference range for age. In certain embodiments, hyperoxaluria is characterized by glycolate/creatinine ratio greater than the reference range for age. Hyperoxaluria includes both primary hyperoxaluria and secondary hyperoxaluria.

"Primary hyperoxaluria" refers to a condition characterized by the overproduction of oxalate and/or defective production or function of one or more enzymes that regulate the levels of oxalate in the body. In certain embodiments, the primary hyperoxaluria is associated with deficiency in the expression of alanine:glyoxylate aminotransferase (AGT) or a mutation in AGXT, the gene encoding AGT, and may be classified as Type 1 primary hyperoxaluria, or PH1. In certain embodiments, the primary hyperoxaluria is associated with deficiency in the expression of glyoxylate reductase (GR) or a mutation in the gene encoding GR (GRPHR), and which may be classified as Type 2 primary hyperoxaluria, or PH2. In yet other embodiments, the primary hyperoxaluria is associated with the deficiency in the expression of 4-hydroxy-2-oxoglutarate aldolase (HOGA) or a mutation in the gene encoding HOGA (HOGA1), and which may be classified as Type 3 primary hyperoxaluria, or PH3.

"Secondary hyperoxaluria" refers to a condition characterized by elevated levels of oxalate in the urine or plasma, or the presence of kidney stones. Secondary hyperoxaluria includes enteric hyperoxaluria caused for example, by increased intake and intestinal absorption of dietary oxalate, excessive intake of oxalate precursors and alteration in the intestinal microflora. Secondary hyperoxaluria also includes idiopathic hyperoxaluria, of unknown etiology.

The term "solvate" as used herein and unless otherwise indicated, refers to a solvate formed from the association of one or more solvent molecules to a compound provided herein. The term "solvate" includes hydrates (e.g., monohydrate, dehydrate, trihydrate, and the like).

The term "treating," "treat," or "treatment" refers generally to administering one or more pharmaceutical substances, especially at least one compound of Formula (I) to a patient that has a disease, disorder or condition, or has a symptom or condition of a disease or disorder, or has a predisposition toward a disease or disorder, with the purpose to cure, heal, relieve, alter, alleviate, ameliorate, slow the progress of, delay the onset of, reduce the risk of, improve or affect the disease, disorder or condition or one or more symptoms thereof or the predisposition toward the disease, disorder or condition or its recurrence.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state or to treat the disease or condition.

In any of the embodiments described herein, a compound of the present invention can also be provided as a prodrug, which is a drug derivative or drug precursor compound that typically is inactive or less than fully active until it is converted in the body through a normal metabolic process such as, for example, hydrolysis of an ester or amide form of the drug, to the active drug. A prodrug may be selected and used instead of the parent drug because, for example, in its prodrug form it is less toxic, and/or may have better absorption, distribution, metabolism and excretion (ADME) characteristics, and the like, than the parent drug. A prodrug might also be used to improve how selectively the drug interacts with cells or processes that are not its intended target. This approach may be employed particularly, for example, to prevent or decrease adverse effects, especially in cancer treatments, which may be especially prone to having severe unintended and undesirable side effects.

The term "prodrug" denotes a derivative of a compound, which derivative, when administered to warm-blooded animals, e.g., humans, is converted into the compound (drug). For example, the enzymatic and/or chemical hydrolytic cleavage of a derivative compound of the present invention occurs in such a manner that the proven drug form is released, and the moiety or moieties split off remain nontoxic or are metabolized so that nontoxic metabolites are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

The prodrug can be prepared in situ during the isolation and purification of the compound of Formula I, including a compound of Formula I, or by separately reacting the purified compound with a suitable derivatizing agent. For example, hydroxy groups can be converted into esters via treatment with a carboxylic acid in the presence of a catalyst. Examples of cleavable alcohol prodrug moieties include substituted or unsubstituted, branched or unbranched alkyl ester moietieds, e.g., ethyl esters, alkenyl esters, di-alkylamino alkyl esters, e.g., dimethylaminoethyl ester, acylamino alkyl esters, acyloxy alkyl esters (e.g., pivaloyloxymethyl ester), aryl esters, e.g., phenyl ester, aryl-alkyl esters, e.g., benzyl ester, optionally substituted, e.g., with methyl, halo, or methoxy substituents aryl and aryl-alkyl esters, amides, alkyl amides, di-alkyl amides, and hydroxy amides.

Knowing the disclosures herein, it will be appreciated also that a compound of the present disclosure can be in the form of a prodrug, and that such prodrugs can be prepared using reagents and synthetic transformations that are well-known to those having ordinary skill in the art. The effectiveness of a particular prodrug can be determined using one or more analytical methods (e.g. pharmacokinetics, bioassays, in vivo efficacy studies, and the like) that are well-known to those of ordinary skill in the art.

More specifically, a prodrug of a compound of Formula I, may be prepared using routine chemical procedures. For example, a hydroxyl substituent on a compound of Formula I can be substituted with —CO-alkyl, —CO$_2$alkyl, —CONH-alkyl, —CO-alkenyl, —CO$_2$-alkenyl, —CONH-alkenyl, —CO-aryl, —CO$_2$-aryl, —CONH-aryl, —CO-heterocycle, —CO$_2$-heterocycle, —CONH-heterocycle, or —PO$_3$H$_2$. Specific modifying groups of hydroxyl include, for example, acetyl, propionyl, isobutyryl, pivaloyl, palmitoyl, benzoyl, 4-methylbenzoyl, dimethylcarbamoyl, dimethylaminomethylcarbonyl, sulfo, alanyl, and fumaryl group.

An amino group can be substituted with —CO-alkyl, —CO$_2$-alkyl, —CO-alkenyl, —CO$_2$— alkenyl, —CO$_2$-aryl, —CO-aryl, —CO-heterocycle, —CO$_2$-heterocycle, or —PO$_3$H$_2$. The alkyl, alkenyl, aryl, and heterocycle moieties are optionally substituted by halogen, alkyl, hydroxyl, alkoxy, carboxy, amino, an amino acid residue, —PO$_3$H$_2$, —SO$_3$H, —OPO$_3$H$_2$, and —OSO$_3$H. Specific modifying groups of amino include, for example, tert-butyl, docosanoyl, pivaloylmethyloxy, alanyl, hexylcarbamoyl, pentylcarbamoyl, 3-methylthio-1-(acetylamino)propylcarbonyl, 1-sulfo-1-(3-ethoxy-4-hydroxyphenyl)methyl, (5-methyl-2-oxo-1,3-dioxol-4-yl)methyl, (5-methyl-2-oxo-1,3-dioxol-4-yl)methoxycarbonyl, tetrahydrofuranyl, and pyrrolidylmethyl.

Suitable modifying groups of carboxyl include, for example, methyl, ethyl, propyl, isopropyl, butyl, isobutyl, tert-butyl, pivaloyloxymethyl, carboxymethyl, dimethylaminomethyl, 1-(acetyloxy)ethyl, 1-(ethoxycarbonyloxy)ethyl, 1-(isopropyloxycarbonyloxy)ethyl, 1-(cyclohexyloxycarbonyloxy)ethyl, carboxylmethyl, (5-methyl-2-oxo-1,3-dioxol-4-yl)methyl, benzyl, phenyl, o-tolyl, morpholinoethyl, N,N-diethylcarbamoylmethyl, and phthalidyl.

The compounds of the present disclosure include the compounds themselves, as well as their salts, solvate and solvate of the salt, if applicable. In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. For example, an inorganic acid (e.g., hydrochloric acid, sulfuric acid, phosphoric acid, or hydrobromic acid), an organic acid (e.g., oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, or benzylsulfonic acid), an inorganic base (e.g., sodium hydroxide, potassium hydroxide, calcium hydroxide, magnesium hydroxide, or ammonium hydroxide), an organic base (e.g., methylamine, diethylamine, triethylamine, triethanolamine, ethylenediamine, tris(hydroxymethyl)methylamine, guanidine, choline, or cinchonine), or an amino acid (e.g., lysine, arginine, or alanine) can be used. Generally, non-aqueous media such as ether, ethyl acetate, ethanol, isopropanol, or acetonitrile are typical. Lists of suitable salts are found in *Remington's Pharmaceutical Sciences,* 18th ed., Mack Publishing Company, Easton, P A, 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium of salt.

The present disclosure also encompasses all suitable isotopic variants of the compounds according to the present disclosure, whether radioactive or not. An isotopic variant of a compound according to the present disclosure is understood to mean a compound in which at least one atom within the compound according to the present disclosure has been exchanged for another atom of the same atomic number, but with a different atomic mass than the atomic mass which usually or predominantly occurs in nature. Examples of isotopes which can be incorporated into a compound according to the present disclosure are those of hydrogen, carbon, nitrogen, oxygen, fluorine, chlorine, bromine and iodine, such as $^2$H (deuterium), $^3$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{125}$I, $^{129}$I and $^{131}$I. Particular isotopic variants of a compound according to the present disclosure, especially those in which one or more radioactive isotopes have been incorporated, may be beneficial, for example, for the examination of the mechanism of action or of the active compound distribution in the body. Compounds labelled with $^3$H, $^{14}$C and/or $^{18}$F isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. In some embodiments, hydrogen atoms of the compounds described herein may be replaced with deuterium atoms. In certain embodiments, "deuterated" as applied to a chemical group and unless otherwise indicated, refers to a chemical group that is isotopically enriched with deuterium in an amount substantially greater than its natural abundance. Isotopic variants of the compounds according to the present disclosure can be prepared by various, including, for example, the methods described below and in the working examples, by using corresponding isotopic modifications of the particular reagents and/or starting compounds therein.

Pharmaceutical Compositions

The methods described herein comprise administering a compound of Formula I or a prodrug or a pharmaceutically acceptable salt thereof in the form of a pharmaceutical composition. In particular, a pharmaceutical composition will comprise at least one compound of Formula I or a prodrug or a pharmaceutically acceptable salt thereof and a pharmaceutically acceptable carrier. The pharmaceutically acceptable excipients described herein, for example, vehicles, adjuvants, carriers or diluents, are well-known to those who are skilled in the art and are readily available to the public. Typically, the pharmaceutically acceptable carrier is one that is chemically inert to the active compounds and one that has no detrimental side effects or toxicity under the conditions of use.

The pharmaceutical compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously.

In accordance with any of the embodiments, the compound of Formula I or a prodrug or a pharmaceutically acceptable salt thereof can be administered orally to a subject in need thereof. Formulations suitable for oral administration can consist of (a) liquid solutions, such as an effective amount of the compound dissolved in diluents, such as water, saline, or orange juice and include an additive, such as cyclodextrin (e.g., α-, β-, or γ-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of Formula I or a salt thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the inhibitors in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of Formula I may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

The compound of Formula I or a prodrug or a pharmaceutically acceptable salt, solvate, or hydrate thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

The dose administered to the mammal, particularly human and other mammals, in accordance with the present disclosure should be sufficient to affect the desired response. One skilled in the art will recognize that dosage will depend upon a variety of factors, including the age, condition or disease state, predisposition to disease, genetic defect or defects, and body weight of the mammal. The size of the dose will also be determined by the route, timing and frequency of administration as well as the existence, nature, and extent of any adverse side-effects that might accompany the administration of a particular inhibitor and the desired effect. It will be appreciated by one of skill in the art that various conditions or disease states may require prolonged treatment involving multiple administrations.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Dosage forms include from about 0.001 mg to about 2,000 mg (including, from about 0.001 mg to about 1,000 mg, from about 0.001 mg to about 500 mg, from about 0.01 mg to about 250 mg) of a compound of Formula (I) or a salt (e.g., a pharmaceutically acceptable salt) thereof as defined anywhere herein. The dosage forms can further include a pharmaceutically acceptable carrier and/or an additional therapeutic agent.

Appropriate dosage levels may be determined by any suitable method. Preferably, the active substance is administered at a frequency of 1 to 4 times per day for topical administration, or less often if a drug delivery system is used. Nevertheless, actual dosage levels and time course of administration of the active ingredients in the pharmaceutical compositions of the present disclosure may be varied so as to obtain an amount of the active ingredient which is effective to achieve a desired therapeutic response for a particular patient, composition and mode of administration, without being intolerably toxic to the patient. In certain cases, dosages may deviate from the stated amounts, in particular as a function of age, gender, body weight, diet and general health status of the patient, route of administration, individual response to the active ingredient, nature of the preparation, and time or interval over which administration takes place. Thus, it may be satisfactory in some cases to manage with less than the aforementioned minimum amount, whereas in other cases the stated upper limit may be exceeded. It may in the event of administration of larger amounts be advisable to divide these into multiple individual doses spread over the day.

Methods of Treatment

The methods of this disclosure comprise administering an effective amount of a compound of Formula I or a prodrug or a pharmaceutically acceptable salt, solvate, or hydrate thereof. Compounds of this disclosure have shown activity as LDH inhibitors.

LDH inhibitors may prove to be effective for diseases resulting from an increase in oxalate or where oxalate reduction may be beneficial. An example is primary hyperoxaluria, which is a disease resulting from an overproduction of oxalate, for example, due to overproduction or accumulation of its precursor, glyoxylate. Provided herein therefore are methods of treating or preventing diseases or disorders associated with elevated oxalate levels. Diseases or disorders associated with elevated oxalate levels include hyperoxaluria, chronic kidney disease (CKD), end stage renal disease (ESRD) or kidney stone disease. In certain embodiments, the hyperoxaluria is associated with various digestive or bowel diseases such as Crohn's diseases, Hirschspring's disease, cystic fibrosis and chronic biliary or pancreatic pathology. In certain embodiments, the hyperoxaluria is associated with bariatric surgery and ileal resection. In certain embodiments, the chronic kidney disease is associated with diabetes, hypertension, previous episode(s) of acute kidney injury, cardiovascular disease or dyslipidemia. In certain embodiments, the kidney stone disease is idiopathic kidney stone disease, or kidney stone disease associated with hyperparathyroidism or other disorders of calcium metabolism. In certain embodiments, the elevated oxalate levels is associated with diabetes mellitus, obesity or metabolic syndrome (MS). The compounds and compositions provided herein may be used to treat or prevent hyperoxaluria, including primary hyperoxaluria and the subtypes PH1, PH2 and PH3 as well as secondary hyperoxaluria, including enteric hyperoxaluria and idiopathic hyperoxaluria. The compounds and compositions provided herein may be used to treat calcium oxalate stone formation, for example, in the kidney, urinary tract or bladder, treat calcium oxalate deposition in other tissues and organs outside the kidney (systemic oxalosis) or prevent or delay kidney damage or the onset of chronic kidney disease (CKD) or end stage renal disease (ESRD).

Methods of treatment include administering a sufficient amount of a compound, salt, or hydrate thereof to provide a meaningful benefit to a patient having a condition or disease associated with elevated oxalate levels. In certain embodiments, elevated oxalate levels means having a urinary oxalate excretion rate of greater than about 0.5 mmol/1.73 $m^2$ per day, greater than about 0.7 mmol/1.73 $m^2$ per day, greater than about 0.8 mmol/1.73 $m^2$ per day, greater than about 1.0 mmol/1.73 $m^2$ per day, greater than about 1.2 mmol/1.73 $m^2$ per day or greater than about 2 mmol/1.73 $m^2$ per day. In certain embodiments, elevated oxalate levels means having a urinary oxalate excretion rate that is greater than normal urinary oxalate excretion. In certain embodiments, normal oxalate urinary excretion is less than about 0.45 mmol/1.73 $m^2$ per day, less than about 0.46 mmol/1.73 $m^2$ per day or less than about 0.5 mmol/1.73 $m^2$ per day. In certain embodiments, elevated oxalate levels means having a urinary oxalate excretion rate that is greater than about 40 mg/day. In certain embodiments, elevated oxalate levels means having a urinary oxalate excretion rate that is greater than about 45 mg/day. In certain embodiments, the urinary oxalate excretion rate is about two-fold higher than normal. In certain embodiments, the urinary oxalate excretion rate is about four-fold higher than normal. In certain embodiments, elevated oxalate levels means having a plasma oxalate levels greater than normal plasma oxalate levels of about 1 µmol/L to about 3 µmol/L. In certain embodiments, elevated oxalate levels means having a plasma oxalate level equal to or greater than about 10 µmol/L. In certain embodiments, elevated oxalate levels means having a plasma oxalate level equal to or greater than about 20 µmol/L.

The meaningful benefit observed in the patient can be to any suitable degree, for example a decrease in symptoms of 10, 20, 30, 40, 50, 60, 70, 80, 90%, or more. In some aspects, one or more symptoms of primary hyperoxaluria are prevented, reduced, halted, or eliminated subsequent to administration of a compound of Formula I, including a compound of Formula I, or a prodrug or a pharmaceutically acceptable salt, solvate, or hydrate thereof, thereby effectively treating primary hyperoxaluria to at least some degree. Symptoms of primary hyperoxaluria include the formation of kidney stones and symptoms associated with kidney stones, such as severe or sudden abdominal or flank pain, frequent urination, blood in urine, and fever. At later stages, symptoms of primary hyperoxaluria include decreased kidney function and end stage renal disease, and the symptoms associated with decreased kidney function and end stage renal disease, such as decreased urine output, failure to make urine, poor appetite, anemia, nausea, vomiting, and changes to hair, skin, and bone. Another symptom of primary hyperoxaluria is oxalosis, which can cause skin ulcers, bone disease, and in children, failure to grow.

The disclosure provide a method treating kidney disease and kidney stones, reducing the symptoms of kidney disease, reducing the size of kidney stones, reducing the amount of kidney stones, reducing the rate of kidney stone formation, preventing kidney disease, or preventing kidney stone formation in patients with idiopathic calcium oxalate kidney stone disease or undefined primary hyperoxaluria by administering a compound of Formula I or salt, solvate, or hydrate thereof to a patient in need of such treatment.

Effective amounts may vary depending upon the biological effect desired in the individual, condition to be treated, and/or the specific characteristics of the compound of Formula I, including a compound of Formula I, or a prodrug or a pharmaceutically acceptable salt, solvate, or hydrate thereof, and the individual. In this respect, any suitable dose of the compound of Formula I or a prodrug or a pharmaceutically acceptable salt, solvate, or hydrate thereof can be administered to the patient (e.g., human), according to the type of primary hyperoxaluria to be treated, the severity of the patient's symptoms, the patient's age, weight, sex and so forth. Various general considerations taken into account in determining the "effective amount" are known to those of skill in the art and are described, e.g., in Gilman et al., eds., Goodman And Gilman's: *The Pharmacological Bases of Therapeutics*, 8th ed., Pergamon Press, 1990; and Remington's Pharmaceutical Sciences, 17th Ed., Mack Publishing Co., Easton, Pa., 1990, each of which is herein incorporated by reference. The dose of the compound of Formula I, including a compound of Formula I, or a prodrug or a pharmaceutically acceptable salt, solvate, or hydrate thereof desirably comprises about 0.01 mg per kilogram (kg) of the body weight of the mammal (mg/kg) to about 1000 mg/kg (e.g., from about 0.01 to about 100 mg/kg, from about 0.1 to about 100 mg/kg) every 4 to 120 hours, or according to the requirements of the particular drug, dosage form, and or route of administration. The daily dose may be administered as a single dose, or one or more divided doses.

An effective amount may also be an amount effective to produce 24 hour urine oxalate amounts of less than defined amount, for example an amount sufficient to provide urine oxalate levels of less than 100 mg/day, less than 80 mg/day, 60 mg/day, less than 50 mg/day, less than 40 mg/day, or less than 30 mg/day. An "effective amount" can also be an amount sufficient to show a meaningful benefit in an individual, e.g., decreasing at least one symptom of primary hyperoxaluria, delaying or preventing the onset of primary hyperoxaluria in an individual known to be at risk for developing hyperoxaluria due to having a genetic mutation in alanine-glycolate aminotransferase (AGXT); glyoxylate reductase/hydroxypyruvate reductase (GPHPR), 4-hydroxy-2-oxoglutarate aldolase 1 (HOGA1), or other enzyme determined to be associated with the development of primary hyperoxaluria.

In an aspect, a compound Formula I inhibits LDHA and/or LDHB. In an embodiment, a compound of Formula I is selective for LDHA and/or LDHB relative to other dehydrogenases (e.g., GAPDH and PHGDH). For example, the compound can be at least 2 times (e.g., at least 5 times, at least 10 times, at least 20 times, at least 50 times, or at least 100 times) more selective for LDHA and/or LDHB compared to one or more other dehydrogenases.

While not wishing to be bound by any particular theory, it is believed that inhibition of LDH reduces or prevents the conversion of glyoxylate to oxalate. Excess oxalate can cause the formation of oxalate crystals, which can form kidney stones or oxalate deposits in the urinary tract, liver, and other parts of a patient's body, resulting in hyperoxaluria. LDH activity can be measured by any suitable method, including the assays described herein. Oxalate production and the accumulation of oxalate-containing stones or deposits can also be measured by a variety of methods. For example, oxalate production can be measured by level of oxalate in a patient's blood or urine. Kidney stone formation can be monitored by ultrasound, MRI, CT scan, or intravenous pyleography.

The disclosure is further directed to a method of inhibiting lactate dehydrogenase A (LDHA) and/or lactate dehydrogenase B (LDHB) activity in a cell comprising administering a compound of Formula I, or a prodrug or a pharmaceutically acceptable salt, solvate, or hydrate thereof to a cell, whereby activity of LDHA and/or LDHB is inhibited. LDHA and LDHB activity can be measured by any method known in the art for measuring enzyme inhibitions, including by the assays described herein. Typically, inhibition of LDHA and LDHB activity will be demonstrated by a decrease in lactate accumulation and/or an increase in pyruvate relative to a control sample.

The disclosure includes methods of treating primary hyperoxaluria and idiopathic hyperoxaluria by administering a therapeutically effective amount of a compound of Formula I or a salt, solvate, or hydrate or prodrug thereof, wherein a therapeutically effective amount is an amount sufficient to prevent primary hyperoxaluria or iodopathic hyperoxaluria in a patient known to be at risk for primary hyperoxaluria or iodopathic hyperoxaluria, delay the onset of primary hyperoxaluria or iodopathic hyperoxaluria in a patient known to be at risk for primary hyperoxaluria or iodopathic hyperoxaluria, decrease the severity of primary hyperoxaluria or iodopathic hyperoxaluria, or decrease the symptoms of hyperoxaluria. The therapeutically effective amount of a compound of Formula I, or a salt, solvate, or hydrate or prodrug thereof, can also be an amount sufficient to significantly reduce the concentration of oxalate in the patient's urine or blood compared to the level of oxalate in the patient's urine or blood prior to administration of the compound of Formula I, or a salt, solvate, or hydrate or prodrug thereof.

The therapeutically effective amount is an amount sufficient to reduce LDH activity in the patient's liver compared to the level of LDH activity in the patient's liver prior to administration of the compound of Formula I or salt, solvate, or hydrate or prodrug thereof.

The therapeutically effective amount of a compound of Formula I, or a salt, solvate, or hydrate or prodrug thereof can also be an amount sufficient to decrease the mean size of kidney stones in the patient's kidneys or decrease the total number of kidney stones in the patient's kidneys.

The disclosure includes a method of treating primary hyperoxaluria wherein the primary hyperoxaluria is primary hyperoxaluria type 1 (PH type 1).

The disclosure includes a method of treating primary hyperoxaluria wherein the primary hyperoxaluria is primary hyperoxaluria type 2 (PH type 2).

The disclosure includes a method of treating primary hyperoxaluria wherein the primary hyperoxaluria is primary hyperoxaluria type 3 (PH type 3).

This disclosure includes a method of treating primary hyperoxaluria wherein the primary hyperoxaluria is not yet defined (non PH1/2/3)

This disclosure includes a method of treating idiopathic hyperoxaluria wherein the idiopathic is defined as any stone former with calcium oxalate stones.

Combination Methods of Treatment

Methods of the disclosure include administering a compound of Formula I, or salt, solvate, hydrate, or prodrug thereof, as a monotherapy, i.e. the compound of Formula I is the only active agent. In certain embodiments of this method, the compound of Formula I, including a compound of Formula I, or a prodrug or a pharmaceutically acceptable salt, solvate, or hydrate thereof can be co-administered with one or more additional active agent. The terms "co-administered" or "co-administration" refer to simultaneous or sequential administration. A compound may be administered before, concurrently with, or after administration of another compound.

One or more than one, e.g., two, three, or more additional therapeutic agents can be administered. In this regard, the present disclosure is directed a pharmaceutical composition comprising a pharmaceutically acceptable carrier and a combination of the compound of Formula I, including a compound of Formula I, or a prodrug or a pharmaceutically acceptable salt, solvate, or hydrate thereof and at least one additional active agent useful for treating the causes or symptoms of primary hyperoxaluria.

The at least one additional active agent can be Vitamin B-6, phosphate, citrate, stiripentol (DIACOMIT), freeze-dried live *Oxalobacter formigenes* (OXABACT, by OxThera), reloxaliase (ALLN-177, by Allena Pharmaceuticals), or an RNAi. Example of RNAi include DCR-PHXC (by Dicerna) and Lumasiran (by Alnylam Pharmaceuticals).

For purposes of the present disclosure, the term "patient" typically is directed to a mammal. Mammals include, but are not limited to, the order Rodentia, such as mice, and the order Logomorpha, such as rabbits. In some aspects, the mammals are from the order Carnivora, including Felines (cats) and Canines (dogs), Artiodactyla, including Bovines (cows) and Swines (pigs) or of the order Perssodactyla, including Equines (horses). In some aspects, the mammals are of the order Primates, Ceboids, or Simioids (monkeys) or of the order Anthropoids (humans and apes). In embodiments of the disclosure, the patient is a human. The "patient" may also be a companion animal such as a dog or cat.

The following examples are provided for further illustration, and should not be construed as limiting in any way.

EXAMPLES

Example 1. Inhibition of Ldha Activity

This example describes a human LDHA primary biochemical assay employed in the characterization of a compound of Formula I in an embodiment of the disclosure.

Test compounds were placed in a Greiner Bio-One (Monroe, NC) 1536-well black solid bottom assay plate. 200 millimolar (mM) Tris HCl, pH 7.4, 100 micromolar (µM) EDTA and 0.01% TWEEN-20™, final concentration, was used as the assay buffer. The LDHA reagent was 2 nanomolar (nM) Human LDHA (Meridian Life Science, Inc., Memphis, TN), final concentration, in assay buffer. The substrate reagent was 0.06 mM NADH and 0.2 mM sodium pyruvate, final concentration, in assay buffer. The resazurin/diaphorase coupling reagent was 0.037 mM resazurin and 0.133 milligrams per milliliter (mg/mL) diaphorase, final concentration, in assay buffer. The sequence of steps, amount and types of reagents, and time required for each step are set forth in Table 1. The inhibition of LDHA activity was measured by fluorescence emission.

TABLE 1

| Sequence | Parameter | Value | Notes |
|---|---|---|---|
| 1 | Reagent | 3 µL | LDHA reagent |
| 2 | Compound | 23 nL | Compound of Formula I |
| 3 | Time | 15 min | RT incubation |
| 4 | Reagent | 1 µL | Substrate reagent |
| 5 | Time | 7 min | RT incubation |
| 6 | Reagent | 1 µL | Resazurin/diaphorase coupling reagent |

TABLE 1-continued

| Sequence | Parameter | Value | Notes |
|---|---|---|---|
| 7 | Detector | Fluorescence (ex 525 nm/em 598 nm) | VIEWLUX ™ in end-point mode: 2 sec exp., 5000 excitation energy |

Example 2. Inhibition of Ldhb Activity

This example describes a human LDHB biochemical assay employed in the characterization of a compound of Formula I in an embodiment of the disclosure.

Test compounds were placed in a Greiner Bio-One (Monroe, NC) 1536-well black solid bottom assay plate. 200 mM Tris HCl, pH 7.4, 100 µM EDTA and 0.01% TWEEN-20™, final concentration, was used as the assay buffer. The LDHB reagent was 2 nM Human LDHB (Meridian Life Science, Inc., Memphis, TN), final concentration, in assay buffer. The substrate reagent was 0.13 mM NADH and 0.16 mM sodium pyruvate, final concentration, in assay buffer. The resazurin/diaphorase coupling reagent was 0.037 mM resazurin and 0.133 mg/mL diaphorase, final concentration, in assay buffer. The sequence of steps, amount and types of reagents, and time required for each step are set forth in Table 2. The inhibition of LDHB activity was measured by fluorescence emission.

TABLE 2

| Sequence | Parameter | Value | Notes |
|---|---|---|---|
| 1 | Reagent | 3 µL | LDHB reagent |
| 2 | Compound | 23 nL | Compound of Formula I |
| 3 | Time | 15 min | RT incubation |
| 4 | Reagent | 1 µL | Substrate reagent |
| 5 | Time | 7 min | RT incubation |
| 6 | Reagent | 1 µL | Resazurin/diaphorase coupling reagent |
| 7 | Detector | Fluorescence (ex 525 nm/em 598 nm) | VIEWLUX ™ in end-point mode: 2 sec exp., 5000 excitation energy |

Example 3. Inhibition of PHGDH Activity

This example describes a human PHGDH counterscreen biochemical assay employed in the characterization of a compound of Formula I in an embodiment of the disclosure.

Test compounds were placed in a Greiner Bio-One (Monroe, NC) 1536-well black solid bottom assay plate. 50 mM TEA, pH 8.0, 10 mM $MgCl_2$, 0.05% BSA, and 0.01% TWEEN-20™, final concentration, was used as the assay buffer. The substrate reagent was 10 µM EDTA, 0.625 mM glutamate, 500 nM human PSAT1, 500 nM human PSPH, 0.05 mM 3-phosphoglycerate, 0.1 mM resazurin, and 0.1 mg/mL diaphorase, final concentration, in assay buffer. The PHGDH reagent was 0.15 mM $NAD^+$ and 10 nM human PHGDH, final concentration, in assay buffer. The sequence of steps, amount and types of reagents, and time required for each step are set forth in Table 3. The inhibition of PHGDH activity was measured by fluorescence emission.

TABLE 3

| Sequence | Parameter | Value | Notes |
|---|---|---|---|
| 1 | Reagent | 3 µL | Substrate reagent |
| 2 | Compound | 23 nL | Compound of Formula I |
| 3 | Reagent | 1 µL | PHGDH reagent |

TABLE 3-continued

| Sequence | Parameter | Value | Notes |
|---|---|---|---|
| 4 | Detector | Fluorescence (ex 525 nm/em 598 nm) | VIEWLUX™ in end-point mode: 2 sec exp., 5000 excitation energy, use Δ between 0 and 30 min |

Example 4. Inhibition of GAPDH Activity

This example describes a human GAPDH counterscreen biochemical assay employed in the characterization of a compound of Formula I in an embodiment of the disclosure.

Test compounds were placed in a Greiner Bio-One (Monroe, NC) 1536-well black solid bottom assay plate. 105 mM Tris HCl, pH 7.4, 10 μM EDTA, 1.27 mM $KH_2PO_4$, 0.875 mM $MgCl_2$, 0.0875% BSA, 0.01 mM DTT, and 0.01% TWEEN-20™, final concentration, was used as the assay buffer. The substrate reagent was 0.48 mM glyceraldehyde 3-phosphate, 0.06 mM resazurin, and 0.21 mg/mL diaphorase, final concentration, in assay buffer. The GAPDH reagent was 0.007 mM $NAD^+$ and 2.5 nM human GAPDH, final concentration, in assay buffer. The sequence of steps, amount and types of reagents, and time required for each step are set forth in Table 4. The inhibition of GAPDH activity was measured by fluorescence emission.

TABLE 4

| Sequence | Parameter | Value | Notes |
|---|---|---|---|
| 1 | Reagent | 3 μL | Substrate reagent |
| 2 | Compound | 23 nL | Compound of formula (I) |
| 3 | Reagent | 1 μL | GAPDH reagent |
| 4 | Detector | Fluorescence (ex 525 nm/em 598 nm) | VIEWLUX™ in kinetic mode: 1 sec exp., 5000 excitation energy, use Δ between 0 and 20 min |

Example 5. Cell-Based Metabolite Assay

This example describes cell-based metabolite assay by mass spectrometry (MS) employed in the characterization of a compound of formula (I) in an embodiment of the disclosure.

The sequence of steps, amount and types of reagents, and time required for each step are set forth in Table 5.

TABLE 5

| Sequence | Parameter | Value | Notes |
|---|---|---|---|
| 1 | Reagent | Snu398 cells | 100k/well in 100 μL RPMI 10% FBS-phenol red |
| 2 | Time | 24 h | 37° C., 5% $CO_2$ incubation |
| 3 | Reagent | Wash | Aspirate media and replace with fresh |

TABLE 5-continued

| Sequence | Parameter | Value | Notes |
|---|---|---|---|
| 4 | Reagent | Compound | Dose LDHA inhibitors/controls in media |
| 5 | Time | 48 h | 37° C., 5% $CO_2$ incubation |
| 6 | Reagent | Media | Aspirate 75 μL of media and collect in separate plate. Snap freeze and store at −80° C. Pyruvate/lactate/NADH ion counts collected by Quintara Discovery, Inc. using MS-MS. |

Example 6. Colorimetric/Fluorometric Cell-Based Metabolite Assay

This example describes a cell-based metabolite assay by colorimetric/fluorometric detection.

Cell-based HT Lactate assay is a miniaturized Biovision Lactate Colorimetric/Fluorometric Assay Kit (Cat #K607-100). The assay is roughly a 3.5 hour assay run in a 1536 plate format. Cell number optimization should be run for each cell line to achieve an optimal number in which lactate production equals roughly 90% of the standard curve range. Cell number per well optimization has been performed with the following cell lines: MiaPaCa2—500 cells/well, SNU398—500 cells/well, and P493—500 cells/well. The sequence of steps, amount and types of reagents, and time required for each step are set forth in Table 6.

TABLE 6

| Sequence | Parameter | Value | Notes |
|---|---|---|---|
| 1 | Reagent | MiaPaCa2 cells | 500/well in 4 μL in DMEM 4.5 g/L Glucose, -Glutamate, -FBS, -Phenol Red |
| 2 | Reagent | Compound | Dose LDHA inhibitors with pin tool |
| 3 | Time | 2.5 hr | 37° C., 5% CO2 incubation |
| 4 | Reagent | Compound | 2 μL/well |
| 5 | Time | 48 h | RT |
| 6 | Read | Media | Absorbance (570 nm) and Fluorescence (Ex/Em = 535/590 nm) |

Table 7. Compounds Useful for Treating Primary Hyperoxaluria

Table 7 includes compounds useful for treating primary hyperoxaluria. The biochemical LDHA inhibitory activity, as measured by the assay set forth in Example 1, is shown in TABLE 7. Compounds shown in Table 7, except for compound 250-252, have been previously disclosed. Synthetic methods for making compounds shown in Table 7 have been previously reported and are readily apartment to those of skill in the art. The compounds are assigned an activity level based on $IC_{50}$ as follows: +++<100 nM; ++100 nM-1000 nM.

TABLE 7

| Cmpd ID | Structure | Compound name and physical data | Inhibitory activity IC$_{50}$ (μM) |
|---|---|---|---|
| 101 | 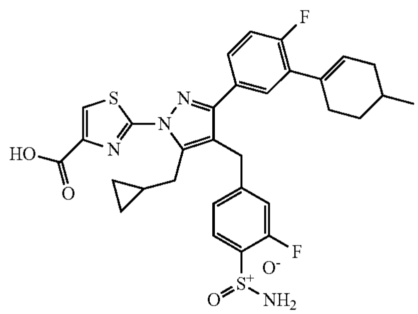 | 2-(5-(cyclopropylmethyl)-3-(6-fluoro-4'-methyl-2',3',4',5'-tetrahydro-[1,1'-biphenyl]-3-yl)-4-(3-fluoro-4-sulfamoylbenzyl)-1H-pyrazol-1-yl)thiazole-4-carboxylic acid, 1H NMR (400 MHz, DMSO-d6) δ 13.16 (s, 1H), 8.27 (s, 1H), 7.67 (t, J = 7.9 Hz, 1H), 7.57 (s, 2H), 7.48 (ddd, J = 8.5, 4.8, 2.3 Hz, 1H), 7.29 (dd, J = 7.5, 2.3 Hz, 1H), 7.22 (s, 1H), 7.21-7.13 (m, 2H), 7.05 (dd, J = 8.1, 1.6 Hz, 1H), 4.13 (s, 2H), 3.18 (d, J = 6.7 Hz, 3H), 2.32-2.07 (m, 3H), 1.83-1.57 (m, 2H), 1.37-1.21 (m, 1H), 1.20-1.09 (m, 1H), 0.97 (d, J = 6.4 Hz, 3H), 0.38-0.31 (m, 2H), 0.26-0.19 (m, 2H); MS [M + H]$^+$ = 625 | +++ |
| 102 | 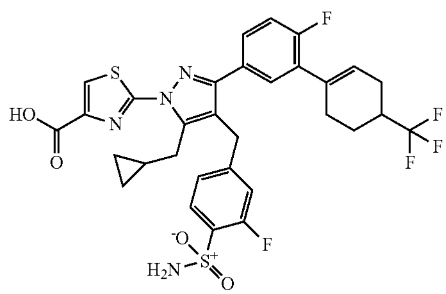 | 2-(5-(cyclopropylmethyl)-3-(6-fluoro-4'-(trifluoromethyl)-2',3',4',5'-tetrahydro-[1,1'-biphenyl]-3-yl)-4-(3-fluoro-4-sulfamoylbenzyl)-1H-pyrazol-1-yl)thiazole-4-carboxylic acid, 1H NMR (400 MHz, DMSO-d6) δ 13.15 (s, 1H), 8.29 (s, 1H), 7.66 (t, J = 7.9 Hz, 1H), 7.58 (s, 2H), 7.51 (ddd, J = 8.5, 4.8, 2.3 Hz, 1H), 7.31 (dd, J = 7.5, 2.3 Hz, 1H), 7.27-7.14 (m, 2H), 7.04 (dd, J = 8.1, 1.6 Hz, 1H), 5.83 (dd, J = 5.0, 2.5 Hz, 1H), 4.14 (s, 2H), 3.19 (d, J = 6.9 Hz, 2H), 2.47-2.13 (m, 3H), 2.08-1.97 (m, 1H), 1.63-1.47 (m, 1H), 1.22-1.08 (m, 1H), 0.39-0.31 (m, 2H), 0.28-0.19 (m, 2H); MS [M + H]$^+$ = 679 | +++ |
| 103 | 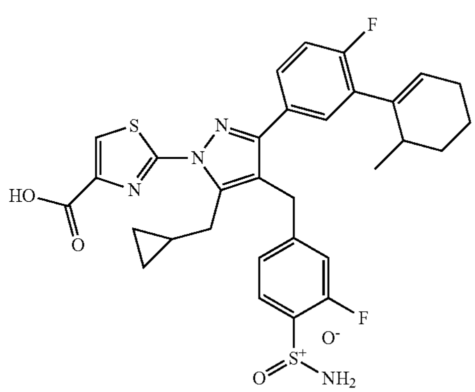 | 2-(5-(cyclopropylmethyl)-3-(6-fluoro-2'-methyl-2',3',4',5'-tetrahydro-[1,1'-biphenyl]-3-yl)-4-(3-fluoro-4-sulfamoylbenzyl)-1H-pyrazol-1-yl)thiazole-4-carboxylic acid, 1H NMR (400 MHz, DMSO-d6) δ 13.14 (s, 1H), 7.67 (t, J = 7.9 Hz, 1H), 7.57 (s, 2H), 7.48 (ddd, J = 8.5, 4.8, 2.3 Hz, 1H), 7.32-7.13 (m, 3H), 7.05 (dd, J = 8.1, 1.6 Hz, 1H), 5.80 (d, J = 3.1 Hz, 1H), 4.13 (s, 2H), 3.18 (d, J = 6.9 Hz, 2H), 2.24 (dd, J = 13.4, 4.8 Hz, 2H), 2.14 (d, J = 17.0 Hz, 1H), 1.79-1.63 (m, 4H), 1.27 (dtd, J = 12.4, 10.3, 5.1 Hz, 1H), 1.22-1.05 (m, 1H), 0.97 (d, J = 6.4 Hz, 3H), 0.40-0.30 (m, 2H), 0.33-0.19 (m, 2H); MS [M + H]$^+$ = 625 | +++ |
| 104 | 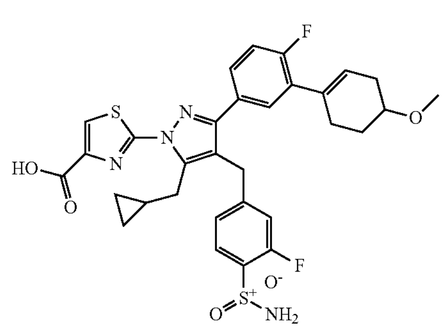 | 2-(5-(cyclopropylmethyl)-3-(6-fluoro-4'-methoxy-2',3',4',5'-tetrahydro-[1,1'-biphenyl]-3-yl)-4-(3-fluoro-4-sulfamoylbenzyl)-1H-pyrazol-1-yl)thiazole-4-carboxylic acid, 1H NMR (400 MHz, DMSO-d6) δ 13.14 (s, 1H), 8.29 (s, 1H), 7.67 (t, J = 7.9 Hz, 1H), 7.58 (s, 2H), 7.49 (ddd, J = 8.5, 4.8, 2.3 Hz, 1H), 7.29 (dd, J = 7.5, 2.3 Hz, 1H), 7.24-7.14 (m, 2H), 7.05 (dd, J = 8.1, 1.6 Hz, 1H), 5.73 (dd, J = 8.3, 4.3 Hz, 1H), 4.13 (s, 2H), 3.47 (dddd, J = 8.0, 6.7, 5.1, 2.9 Hz, 1H), 3.28 (s, 3H), 3.18 (d, J = 6.9 Hz, 2H), 2.45 (d, J = 5.5 Hz, 1H), 2.36-2.13 (m, 2H), 2.14-2.00 (m, 1H), 2.00-1.82 (m, 1H), 1.71-1.51 (m, 1H), 1.23-1.04 (m, 1H), 0.37-0.28 (m, 2H), 0.27-0.17 (m, 2H); MS [M + H]$^+$ = 641 | +++ |

TABLE 7-continued

| Cmpd ID | Structure | Compound name and physical data | Inhibitory activity IC$_{50}$ (μM) |
|---|---|---|---|
| 105 | 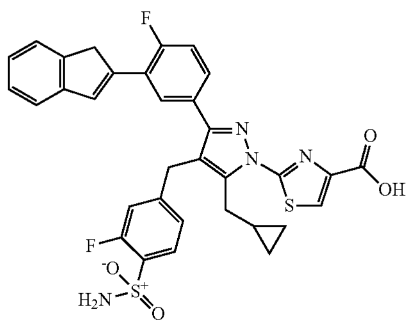 | 2-(5-(cyclopropylmethyl)-3-(4-fluoro-3-(1H-inden-2-yl)phenyl)-4-(3-fluoro-4-sulfamoylbenzyl)-1H-pyrazol-1-yl)thiazole-4-carboxylic acid, 1H NMR (400 MHz, DMSO-d6) δ 13.16 (s, 1H), 8.31 (s, 1H), 7.73 (t, J = 7.9 Hz, 1H), 7.61 (s, 2H), 7.67-7.54 (m, 2H), 7.56-7.44 (m, 2H), 7.41-7.16 (m, 5H), 7.13 (dd, J = 8.1, 1.6 Hz, 1H), 4.21 (s, 2H), 3.59 (d, J = 1.6 Hz, 2H), 3.20 (d, J = 6.9 Hz, 2H), 1.26-1.10 (m, 1H), 0.41-0.31 (m, 2H), 0.29-0.20 (m, 2H); MS [M + H]$^+$ = 645 | +++ |
| 106 | 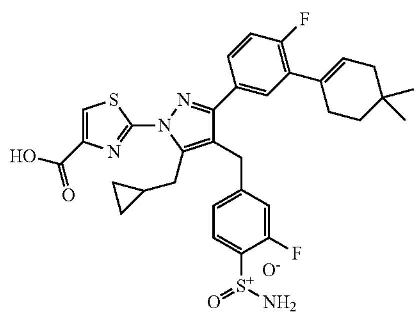 | 2-(5-(cyclopropylmethyl)-3-(6-fluoro-4',4'-dimethyl-2',3',4',5'-tetrahydro-[1,1'-biphenyl]-3-yl)-4-(3-fluoro-4-sulfamoylbenzyl)-1H-pyrazol-1-yl)thiazole-4-carboxylic acid, 1H NMR (400 MHz, DMSO-d6) δ 13.11 (s, 1H), 8.27 (d, J = 1.0 Hz, 1H), 7.64 (t, J = 7.9 Hz, 1H), 7.55 (s, 2H), 7.51-7.44 (m, 1H), 7.29-7.16 (m, 2H), 7.16 (t, J = 10.0 Hz, 2H), 7.02 (d, J = 8.1 Hz, 1H), 5.72 (dt, J = 4.9, 2.5 Hz, 1H), 4.11 (s, 2H), 3.15 (d, J = 6.8 Hz, 2H), 2.12 (d, J = 6.8 Hz, 2H), 1.90 (d, J = 3.3 Hz, 2H), 1.39 (t, J = 6.4 Hz, 2H), 1.12 (p, J = 6.6 Hz, 1H), 0.90 (s, 6H), 0.32 (d, J = 7.9 Hz, 2H), 0.21 (d, J = 4.9 Hz, 2H); MS [M + H]$^+$ = 639 | +++ |
| 107 | 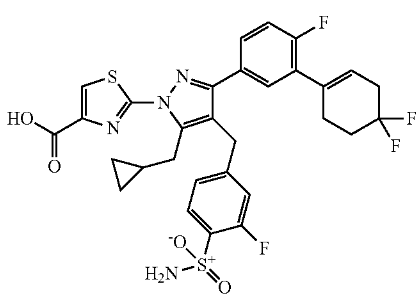 | 2-(5-(cyclopropylmethyl)-4-(3-fluoro-4-sulfamoylbenzyl)-3-(4',4',6-trifluoro-2',3',4',5'-tetrahydro-[1,1'-biphenyl]-3-yl)-1H-pyrazol-1-yl)thiazole-4-carboxylic acid, 1H NMR (400 MHz, DMSO-d6) δ 13.14 (s, 1H), 8.30 (s, 1H), 7.67 (t, J = 7.9 Hz, 1H), 7.59 (s, 2H), 7.53 (ddd, J = 8.5, 4.8, 2.3 Hz, 1H), 7.33 (dd, J = 7.5, 2.3 Hz, 1H), 7.25 (dd, J = 11.0, 8.6 Hz, 1H), 7.17 (dd, J = 11.3, 1.6 Hz, 1H), 7.05 (dd, J = 8.1, 1.6 Hz, 1H), 5.73 (d, J = 17.8 Hz, 1H), 4.14 (s, 2H), 3.24-3.13 (m, 3H), 2.78-2.63 (m, 2H), 2.48 (d, J = 11.3 Hz, 4H), 2.12 (tt, J = 14.0, 6.7 Hz, 2H), 1.23-1.08 (m, 1H), 0.39-0.31 (m, 2H), 0.27-0.19 (m, 2H); MS [M + H]$^+$ = 647 | +++ |
| 108 | 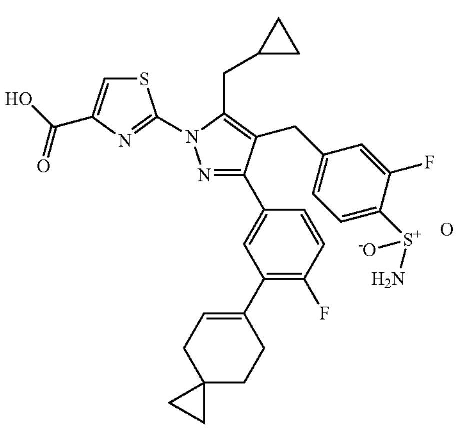 | 2-(5-(cyclopropylmethyl)-3-(4-fluoro-3-(spiro[2.5]oct-5-en-6-yl)phenyl)-4-(3-fluoro-4-sulfamoylbenzyl)-1H-pyrazol-1-yl)thiazole-4-carboxylic acid, 1H NMR (400 MHz, DMSO-d6) δ 13.13 (s, 1H), 8.30 (s, 1H), 7.67 (t, J = 7.9 Hz, 1H), 7.58 (s, 2H), 7.51 (ddd, J = 8.5, 4.8, 2.3 Hz, 1H), 7.29 (dd, J = 7.5, 2.3 Hz, 1H), 7.27-7.15 (m, 2H), 7.06 (dd, J = 8.1, 1.6 Hz, 1H), 5.86 (td, J = 3.6, 2.1 Hz, 1H), 4.14 (s, 2H), 3.18 (d, J = 6.9 Hz, 2H), 2.22 (q, J = 4.7, 4.2 Hz, 2H), 2.04 (dd, J = 3.9, 2.3 Hz, 2H), 1.44 (t, J = 6.1 Hz, 2H), 1.22-1.09 (m, 1H), 0.40-0.28 (m, 6H), 0.27-0.19 (m, 2H); MS [M + H]$^+$ = 637 | +++ |

TABLE 7-continued

| Cmpd ID | Structure | Compound name and physical data | Inhibitory activity IC$_{50}$ (μM) |
|---|---|---|---|
| 109 | 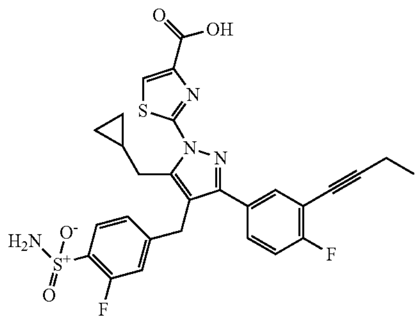 [SMILES: CCC#Cc1cc(-c2nn(-c3nc(C(=O)O)cs3)c(CC3CC3)c2Cc2ccc([S+](N)(=O)[O-])c(F)c2)ccc1F] | 2-(3-(3-(but-1-yn-1-yl)-4-fluorophenyl)-5-(cyclopropylmethyl)-4-(3-fluoro-4-sulfamoylbenzyl)-1H-pyrazol-1-yl)thiazole-4-carboxylic acid, 1H NMR (400 MHz, DMSO-d6) δ 8.00 (s, 1H), 7.66 (t, J = 7.9 Hz, 1H), 7.60-7.51 (m, 2H), 7.29 (dd, J = 9.4, 8.6 Hz, 1H), 7.15 (dd, J = 11.4, 1.6 Hz, 1H), 7.04 (dd, J = 8.1, 1.6 Hz, 1H), 4.14 (s, 2H), 3.17 (d, J = 6.9 Hz, 3H), 2.45 (t, J = 7.5 Hz, 2H), 1.17 (t, J = 7.5 Hz, 3H), 1.13-1.04 (m, 1H), 0.39-0.28 (m, 2H), 0.24-0.15 (m, 2H); MS [M + H]$^+$ = 583 | +++ |
| 110 | 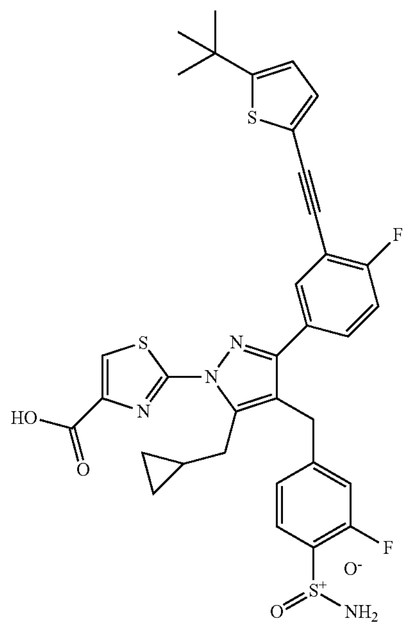 | 2-(3-(3-((5-(tert-butyl)thiophen-2-yl)ethynyl)-4-fluorophenyl)-5-(cyclopropylmethyl)-4-(3-fluoro-4-sulfamoylbenzyl)-1H-pyrazol-1-yl)thiazole-4-carboxylic acid, 1H NMR (400 MHz, DMSO-d6) δ 13.15 (s, 1H), 8.32 (s, 1H), 7.76-7.56 (m, 3H), 7.57 (s, 2H), 7.42-7.33 (m, 1H), 7.29 (d, J = 3.8 Hz, 1H), 7.16 (dd, J = 11.3, 1.6 Hz, 1H), 7.06 (dd, J = 8.2, 1.6 Hz, 1H), 6.92 (d, J = 3.7 Hz, 1H), 4.17 (s, 2H), 3.18 (d, J = 6.9 Hz, 2H), 1.36 (s, 9H), 1.26-1.07 (m, 1H), 0.40-0.30 (m, 2H), 0.27-0.19 (m, 2H); MS [M + H]$^+$ = 693 | ++ |
| 111 | 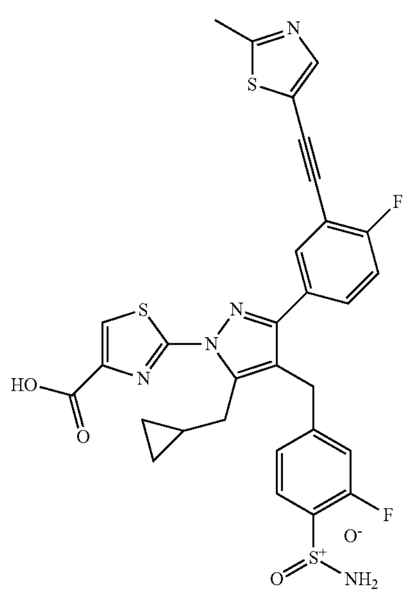 | 2-(5-(cyclopropylmethyl)-3-(4-fluoro-3-((2-methylthiazol-5-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.13 (s, 1H), 8.29 (s, 1H), 7.99 (s, 1H), 7.75 (dd, J = 6.8, 2.3 Hz, 1H), 7.68-7.59 (m, 2H), 7.54 (s, 2H), 7.42-7.33 (m, 1H), 7.14 (dd, J = 11.3, 1.5 Hz, 1H), 7.03 (dd, J = 8.1, 1.6 Hz, 1H), 4.15 (s, 2H), 3.16 (d, J = 6.8 Hz, 2H), 2.68 (s, 3H), 1.26-1.00 (m, 1H), 0.37-0.26 (m, 2H), 0.27-0.16 (m, 2H); MS [M + H]$^+$ = 652 | +++ |

TABLE 7-continued

| Cmpd ID | Structure | Compound name and physical data | Inhibitory activity IC$_{50}$ (μM) |
|---|---|---|---|
| 112 | 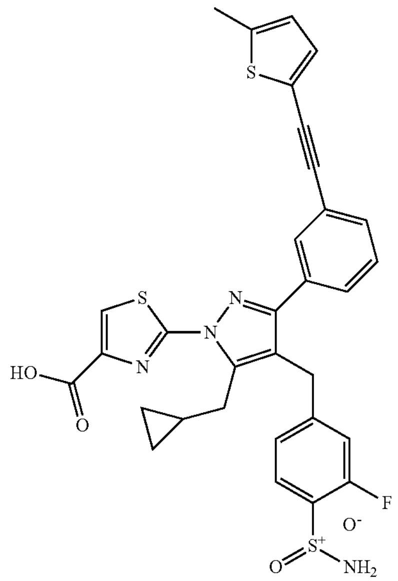 | 2-(5-(cyclopropylmethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.15 (s, 1H), 8.29 (s, 1H), 7.69-7.60 (m, 2H), 7.59-7.47 (m, 4H), 7.42 (t, J = 7.7 Hz, 1H), 7.22 (d, J = 3.6 Hz, 1H), 7.14 (dd, J = 11.3, 1.5 Hz, 1H), 7.04 (dd, J = 8.1, 1.5 Hz, 1H), 6.81 (dd, J = 3.6, 1.3 Hz, 1H), 4.16 (s, 2H), 3.16 (d, J = 7.1 Hz, 2H), 2.47-2.44 (m, 3H), 1.13 (dqd, J = 14.8, 7.2, 5.0 Hz, 1H), 0.38-0.28 (m, 2H), 0.26-0.15 (m, 2H); [M + H]$^+$ = 633 | +++ |
| 113 | 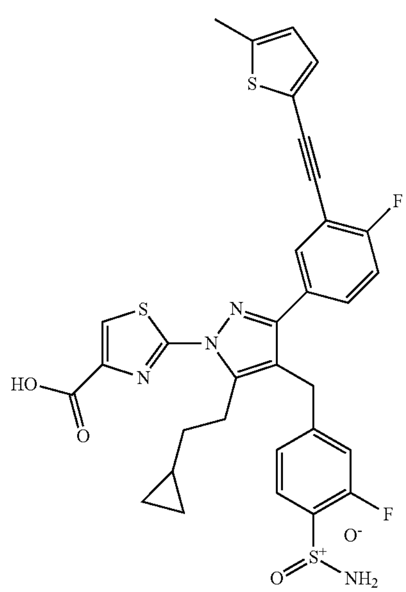 | 2-(5-(2-cyclopropylethyl)-3-(4-fluoro-3-((5-methylthiophen-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.09 (s, 1H), 8.27 (s, 1H), 7.74-7.54 (m, 3H), 7.56 (s, 2H), 7.37 (dd, J = 9.4, 8.7 Hz, 1H), 7.26 (dd, J = 3.6, 0.5 Hz, 1H), 7.16 (dd, J = 11.3, 1.6 Hz, 1H), 7.04 (dd, J = 8.1, 1.6 Hz, 1H), 6.83 (dt, J = 3.5, 1.1 Hz, 1H), 4.14 (s, 2H), 3.27-3.18 (m, 2H), 2.46 (d, J = 1.0 Hz, 3H), 1.41 (q, J = 7.3 Hz, 2H), 0.87-0.61 (m, 1H), 0.34-0.25 (m, 2H), 0.14-0.05 (m, 2H); MS [M + H]$^+$ = 665 | +++ |

TABLE 7-continued

| Cmpd ID | Structure | Compound name and physical data | Inhibitory activity IC$_{50}$ (μM) |
|---|---|---|---|
| 114 | 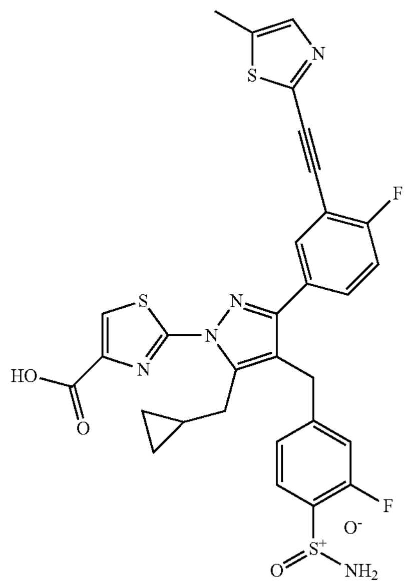 | 2-(5-(cyclopropylmethyl)-3-(4-fluoro-3-((5-methylthiazol-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.13 (s, 1H), 8.27 (s, 1H), 7.85 (dd, J = 6.8, 2.3 Hz, 1H), 7.72-7.59 (m, 3H), 7.54 (s, 2H), 7.41 (t, J = 9.1 Hz, 1H), 7.13 (d, J = 10.9 Hz, 1H), 7.03 (dd, J = 8.1, 1.6 Hz, 1H), 4.17 (s, 2H), 3.15 (dd, J = 6.0, 4.6 Hz, 3H), 2.50 (d, J = 1.2 Hz, 3H), 1.24-0.99 (m, 1H), 0.38-0.28 (m, 2H), 0.24-0.16 (m, 2H); MS [M + H]$^+$ = 652 | +++ |
| 115 | 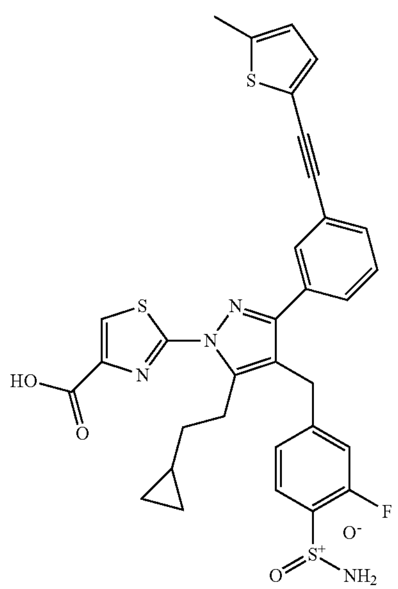 | 2-(5-(2-cyclopropylethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.09 (s, 1H), 8.26 (s, 1H), 7.70-7.62 (m, 2H), 7.57-7.53 (m, 3H), 7.51 (dt, J = 7.7, 1.4 Hz, 1H), 7.44 (td, J = 7.7, 0.6 Hz, 1H), 7.22 (dd, J = 3.6, 0.5 Hz, 1H), 7.16 (dd, J = 11.3, 1.6 Hz, 1H), 7.05 (dd, J = 8.1, 1.6 Hz, 1H), 6.81 (dt, J = 3.4, 1.1 Hz, 1H), 4.15 (s, 2H), 3.27-3.18 (m, 2H), 2.45 (d, J = 1.0 Hz, 3H), 1.41 (q, J = 7.3 Hz, 2H), 0.85-0.59 (m, 1H), 0.33-0.15 (m, 2H), 0.18--0.03 (m, 2H); MS [M + H]$^+$ = 647 | +++ |
| 116 | 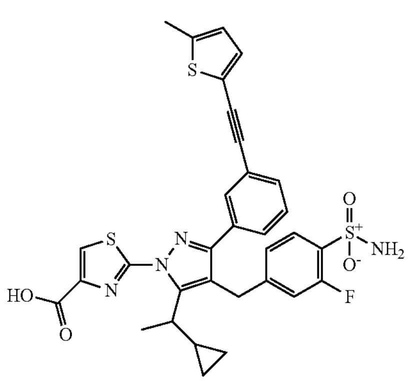 [SMILES: Cc1ccc(C#Cc2cccc(-c3nn(-c4nc(C(=O)O)cs4)c(C(C)C4CC4)c3Cc3ccc([S+](N)(=O)[O-])c(F)c3)c2)s1] | 2-(5-(1-cyclopropylethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.11 (s, 1H), 8.30 (s, 1H), 7.70-7.60 (m, 2H), 7.57-7.38 (m, 5H), 7.23-7.11 (m, 2H), 7.04 (dd, J = 8.1, 1.6 Hz, 1H), 6.80 (dt, J = 3.5, 1.1 Hz, 1H), 4.25-4.19 (m, 2H), 2.45 (d, J = 1.0 Hz, 3H), 1.35 (d, J = 7.2 Hz, 3H), 0.47 (td, J = 8.9, 8.1, 4.0 Hz, 1H), 0.26-0.09 (m, 2H); MS [M + H]$^+$ = 647 | ++ |

TABLE 7-continued

| Cmpd ID | Structure | Compound name and physical data | Inhibitory activity IC$_{50}$ (μM) |
|---|---|---|---|
| 117 | 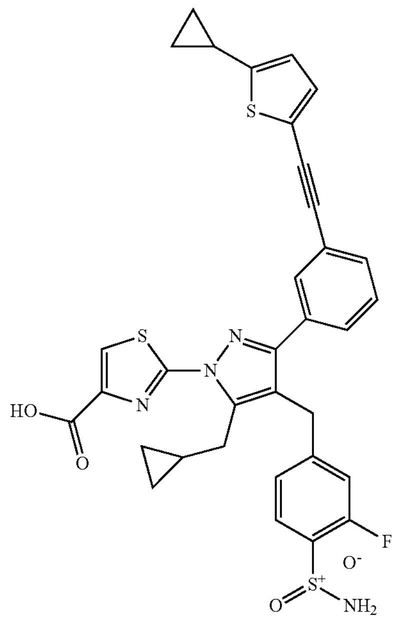 | 2-(5-(cyclopropylmethyl)-3-(3-((5-cyclopropylthiophen-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.12 (s, 1H), 8.29 (s, 1H), 7.68-7.60 (m, 2H), 7.58-7.52 (m, 3H), 7.48 (dt, J = 7.7, 1.5 Hz, 1H), 7.42 (td, J = 7.7, 0.6 Hz, 1H), 7.19 (d, J = 3.7 Hz, 1H), 7.13 (dd, J = 11.4, 1.6 Hz, 1H), 7.04 (dd, J = 8.1, 1.6 Hz, 1H), 6.79 (dd, J = 3.7, 0.7 Hz, 1H), 4.15 (s, 2H), 3.16 (d, J = 6.9 Hz, 2H), 2.15 (ttd, J = 8.3, 5.0, 0.7 Hz, 1H), 1.12 (dddd, J = 13.4, 8.1, 5.0, 1.9 Hz, 1H), 1.06-0.98 (m, 2H), 0.74-0.67 (m, 2H), 0.37-0.28 (m, 2H), 0.24-0.16 (m, 2H); MS [M + H]$^+$ = 659 | ++ |
| 118 | 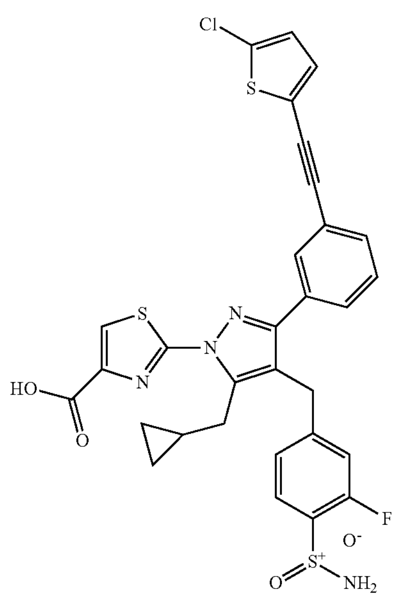 | 2-(3-(3-((5-chlorothiophen-2-yl)ethynyl)phenyl)-5-(cyclopropylmethyl)-4-(3-fluoro-4-sulfamoylbenzyl)-1H-pyrazol-1-yl)thiazole-4-carboxylic acid, 1H NMR (400 MHz, DMSO-d6) δ 13.13 (s, 1H), 8.29 (s, 1H), 7.68 (td, J = 1.7, 0.6 Hz, 1H), 7.66-7.57 (m, 2H), 7.56-7.49 (m, 3H), 7.44 (td, J = 7.8, 0.6 Hz, 1H), 7.31 (d, J = 3.9 Hz, 1H), 7.18-7.11 (m, 2H), 7.04 (dd, J = 8.1, 1.6 Hz, 1H), 4.16 (s, 2H), 3.24-3.12 (m, 2H), 1.23-1.03 (m, 1H), 0.41-0.26 (m, 2H), 0.24-0.16 (m, 2H); MS [M + H]$^+$ = 654 | +++ |

TABLE 7-continued

| Cmpd ID | Structure | Compound name and physical data | Inhibitory activity IC$_{50}$ (µM) |
|---|---|---|---|
| 119 | 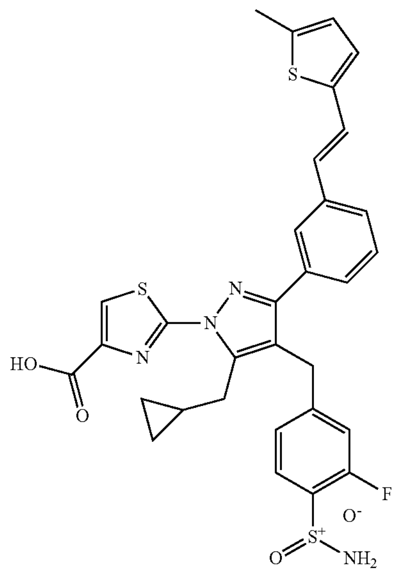 | (E)-2-(5-(cyclopropylmethyl)-4-(3-fluoro-4-sulfamoylbenzyl)-3-(3-(2-(5-methylthiophen-2-yl)vinyl)phenyl)-1H-pyrazol-1-yl)thiazole-4-carboxylic acid, 1H NMR (400 MHz, DMSO-d6) δ 13.11 (s, 1H), 7.68-7.59 (m, 2H), 7.56-7.48 (m, 3H), 7.44-7.31 (m, 2H), 7.20 (dd, J = 16.2, 0.6 Hz, 1H), 7.15 (dd, J = 11.4, 1.5 Hz, 1H), 7.05 (dd, J = 8.1, 1.6 Hz, 1H), 6.97 (d, J = 3.5 Hz, 1H), 6.81-6.70 (m, 2H), 4.16 (s, 2H), 3.16 (d, J = 6.9 Hz, 2H), 2.43 (d, J = 1.1 Hz, 3H), 1.29-0.96 (m, 1H), 0.38-0.27 (m, 2H), 0.25-0.17 (m, 2H); MS [M + H]$^+$ = 635 | +++ |
| 120 | 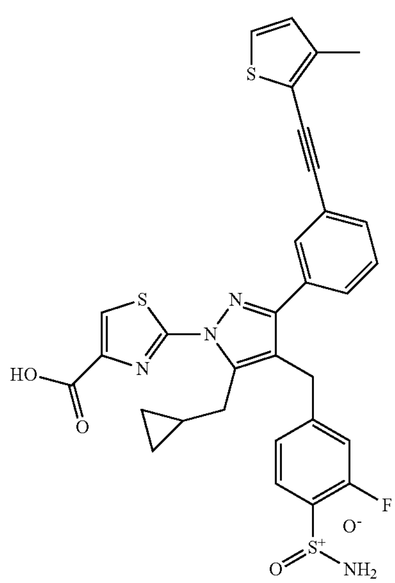 | 2-(5-(cyclopropylmethyl)-4-(3-fluoro-4-sulfamoylbenzyl)-3-(3-((3-methylthiophen-2-yl)ethynyl)phenyl)-1H-pyrazol-1-yl)thiazole-4-carboxylic acid, 1H NMR (400 MHz, DMSO-d6) δ 13.13 (s, 1H), 8.29 (s, 1H), 7.68-7.39 (m, 6H), 7.54 (s, 2H), 7.15 (dd, J = 11.4, 1.6 Hz, 1H), 7.09-6.96 (m, 2H), 4.17 (s, 2H), 3.15 (d, J = 6.9 Hz, 2H), 2.29 (s, 3H), 1.23-0.95 (m, 1H), 0.37-0.28 (m, 2H), 0.25-0.16 (m, 2H); MS [M + H]$^+$ = 633 | +++ |

TABLE 7-continued

| Cmpd ID | Structure | Compound name and physical data | Inhibitory activity IC$_{50}$ (μM) |
|---|---|---|---|
| 121 | 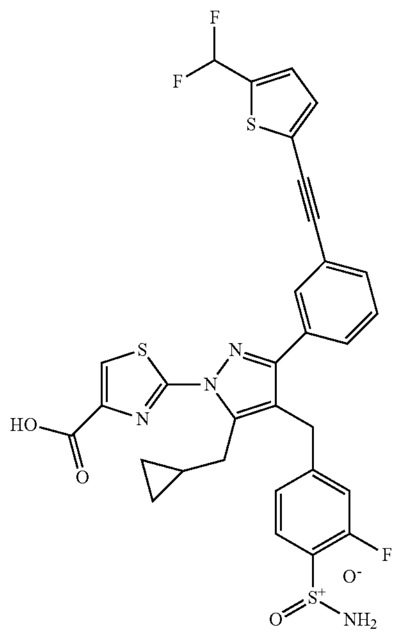 | 2-(5-(cyclopropylmethyl)-3-(3-((5-(difluoromethyl)thiophen-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.13 (s, 1H), 8.28 (s, 1H), 7.72 (td, J = 1.7, 0.6 Hz, 1H), 7.67-7.52 (m, 3H), 7.54 (s, 2H), 7.50-7.40 (m, 3H), 7.19-7.10 (m, 1H), 7.04 (dd, J = 8.1, 1.6 Hz, 1H), 4.17 (s, 2H), 3.16 (d, J = 6.9 Hz, 2H), 1.32-0.93 (m, 1H), 0.38-0.17 (m, 4H); MS [M + H]$^+$ = 669 | +++ |
| 122 | 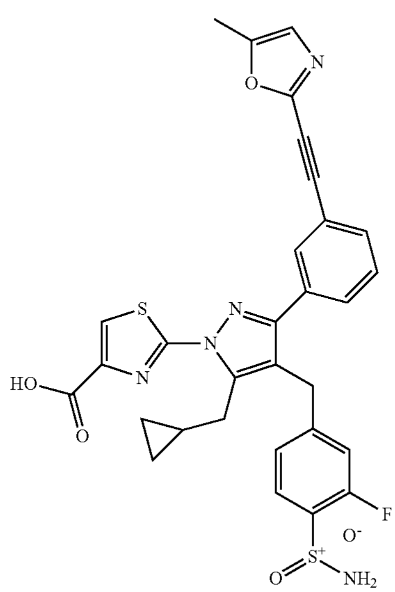 | 2-(5-(cyclopropylmethyl)-4-(3-fluoro-4-sulfamoylbenzyl)-3-(3-((5-methyloxazol-2-yl)ethynyl)phenyl)-1H-pyrazol-1-yl)thiazole-4-carboxylic acid, MS [M + H]$^+$ = 618 | +++ |

TABLE 7-continued

| Cmpd ID | Structure | Compound name and physical data | Inhibitory activity IC$_{50}$ (μM) |
|---|---|---|---|
| 123 | 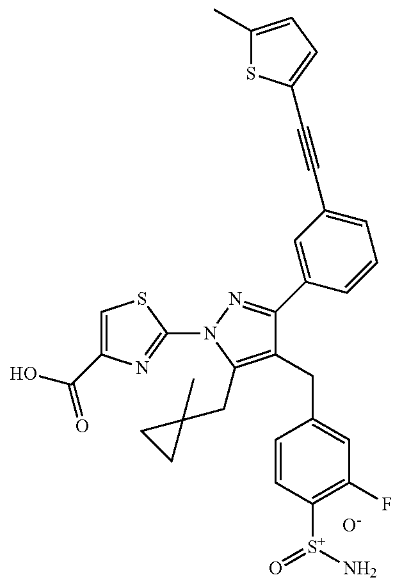 | 2-(4-(3-fluoro-4-sulfamoylbenzyl)-5-((1-methylcyclopropyl)methyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.13 (s, 1H), 7.67 (td, J = 1.7, 0.6 Hz, 1H), 7.61 (t, J = 7.9 Hz, 1H), 7.58-7.51 (m, 3H), 7.48 (dt, J = 7.7, 1.4 Hz, 1H), 7.40 (td, J = 7.7, 0.6 Hz, 1H), 7.21 (dd, J = 3.6, 0.5 Hz, 1H), 7.14-6.97 (m, 2H), 6.81 (dt, J = 3.6, 1.1 Hz, 1H), 4.19 (s, 2H), 3.42 (s, 2H), 2.45 (d, J = 1.0 Hz, 3H), 0.98 (s, 3H), 0.37-0.26 (m, 2H), 0.16-0.05 (m, 2H); MS [M + H]$^+$ = 647 | +++ |
| 124 | 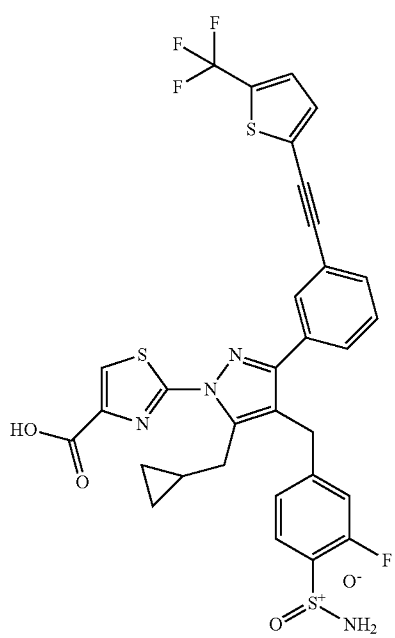 | 2-(5-(cyclopropylmethyl)-4-(3-fluoro-4-sulfamoylbenzyl)-3-(3-((5-(trifluoromethyl)thiophen-2-yl)ethynyl)phenyl)-1H-pyrazol-1-yl)thiazole-4-carboxylic acid, 1H NMR (400 MHz, DMSO-d6) δ 13.14 (s, 1H), 8.29 (s, 1H), 7.76-7.70 (m, 2H), 7.68-7.59 (m, 2H), 7.64-7.50 (m, 2H), 7.54 (s, 2H), 7.54-7.42 (m, 2H), 7.14 (dd, J = 11.4, 1.6 Hz, 1H), 7.04 (dd, J = 8.1, 1.6 Hz, 1H), 4.17 (s, 2H), 3.17 (d, J = 6.9 Hz, 2H), 1.34-1.00 (m, 1H), 0.38-0.17 (m, 4H); MS [M + H]$^+$ = 687 | ++ |

| Cmpd ID | Structure | Compound name and physical data | Inhibitory activity IC$_{50}$ (μM) |
|---|---|---|---|
| 125 | 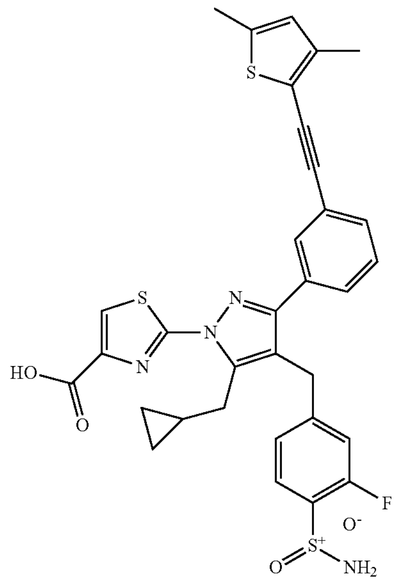 | 2-(5-(cyclopropylmethyl)-3-(3-((3,5-dimethylthiophen-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.12 (s, 1H), 8.29 (s, 1H), 7.68-7.59 (m, 2H), 7.64-7.47 (m, 2H), 7.54 (s, 2H), 7.52-7.38 (m, 2H), 7.14 (dd, J = 11.4, 1.6 Hz, 1H), 7.05 (dd, J = 8.1, 1.6 Hz, 1H), 6.69 (dt, J = 1.4, 0.7 Hz, 1H), 4.16 (s, 2H), 3.15 (d, J = 6.9 Hz, 2H), 2.39 (d, J = 1.1 Hz, 3H), 2.21 (s, 3H), 1.26-0.96 (m, 1H), 0.37-0.27 (m, 2H), 0.25-0.16 (m, 2H); MS [M + H]$^+$ = 647 | +++ |
| 127 | 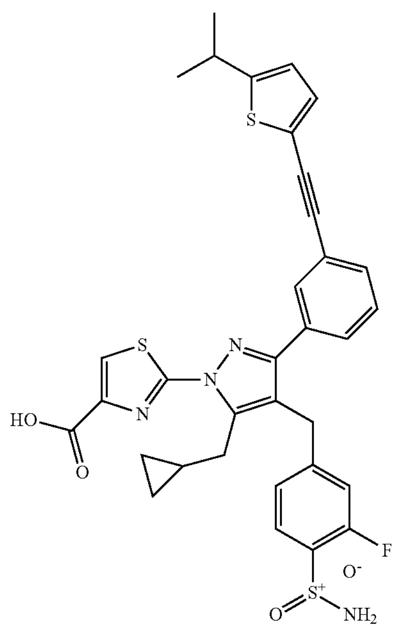 | 2-(5-(cyclopropylmethyl)-4-(3-fluoro-4-sulfamoylbenzyl)-3-(3-((5-isopropylthiophen-2-yl)ethynyl)phenyl)-1H-pyrazol-1-yl)thiazole-4-carboxylic acid, 1H NMR (400 MHz, DMSO-d6) δ 13.13 (s, 1H), 8.29 (s, 1H), 7.70-7.60 (m, 2H), 7.58-7.51 (m, 3H), 7.51 (s, 1H), 7.42 (td, J = 7.7, 0.6 Hz, 1H), 7.23 (d, J = 3.6 Hz, 1H), 7.18-6.99 (m, 2H), 6.86 (dd, J = 3.7, 1.0 Hz, 1H), 4.16 (s, 2H), 3.20-3.10 (m, 3H), 1.28 (s, 3H), 1.26 (s, 3H), 1.23-1.03 (m, 1H), 0.37-0.28 (m, 2H), 0.24-0.15 (m, 2H); MS [M + H]$^+$ = 661 | ++ |
| 128 | 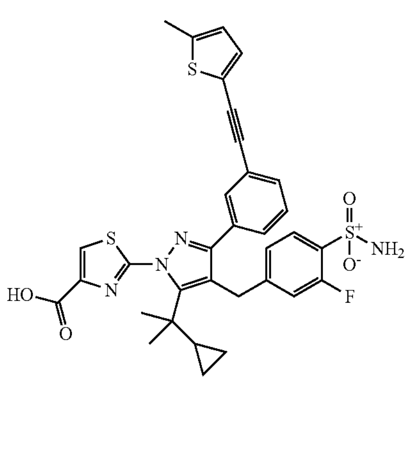 [SMILES: Cc1ccc(C#Cc2cccc(-c3nn(-c4nc(C(=O)O)cs4)c(C(C)(C)C4CC4)c3Cc3ccc([S+](N)(=O)[O-])c(F)c3)c2)s1] | 2-(5-(2-cyclopropylpropan-2-yl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.24 (s, 1H), 8.55 (s, 1H), 7.72 (t, J = 7.9 Hz, 1H), 7.57 (s, 2H), 7.53 (td, J = 1.6, 0.7 Hz, 1H), 7.49 (dt, J = 7.1, 1.8 Hz, 1H), 7.44-7.35 (m, 2H), 7.20-7.16 (m, 1H), 7.16-7.04 (m, 2H), 6.79 (dt, J = 3.4, 1.1 Hz, 1H), 4.28 (s, 2H), 2.44 (dd, J = 1.1, 0.4 Hz, 3H), 1.26 (tt, J = 8.3, 5.7 Hz, 1H), 1.17 (s, 6H), 0.27-0.12 (m, 4H); MS [M + H]$^+$ = 661 | ++ |

TABLE 7-continued

| Cmpd ID | Structure | Compound name and physical data | Inhibitory activity IC$_{50}$ (µM) |
|---|---|---|---|
| 129 | 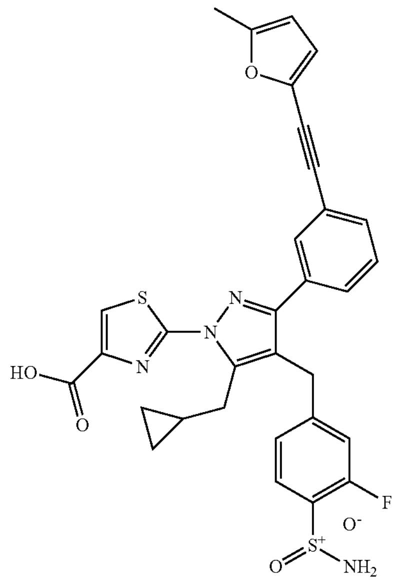 | 2-(5-(cyclopropylmethyl)-4-(3-fluoro-4-sulfamoylbenzyl)-3-(3-((5-methylfuran-2-yl)ethynyl)phenyl)-1H-pyrazol-1-yl)thiazole-4-carboxylic acid, 1H NMR (400 MHz, DMSO-d6) δ 13.13 (s, 1H), 8.28 (s, 1H), 7.68 (td, J = 1.7, 0.6 Hz, 1H), 7.63 (t, J = 7.9 Hz, 1H), 7.59-7.48 (m, 4H), 7.43 (td, J = 7.7, 0.6 Hz, 1H), 7.18-7.01 (m, 2H), 6.78 (dd, J = 3.3, 0.6 Hz, 1H), 6.20 (dq, J = 3.1, 1.0 Hz, 1H), 4.16 (s, 2H), 3.15 (d, J = 6.9 Hz, 2H), 2.29 (t, J = 0.7 Hz, 3H), 1.22-1.02 (m, 1H), 0.40-0.27 (m, 2H), 0.28-0.15 (m, 2H); MS [M + H]$^+$ = 617 | +++ |
| 130 | 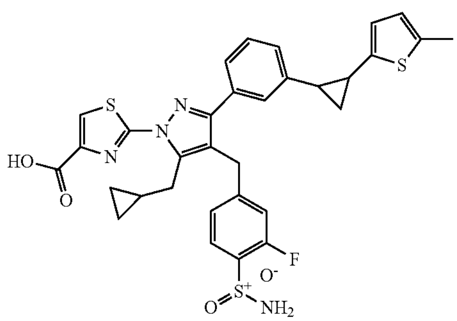 | 2-(5-(cyclopropylmethyl)-4-(3-fluoro-4-sulfamoylbenzyl)-3-(3-(2-(5-methylthiophen-2-yl)cyclopropyl)phenyl)-1H-pyrazol-1-yl)thiazole-4-carboxylic acid, 1H NMR (400 MHz, DMSO-d6) δ 13.13 (s, 1H), 8.28 (s, 1H), 7.65 (t, J = 7.9 Hz, 1H), 7.56 (s, 2H), 7.42-7.26 (m, 3H), 7.21-7.10 (m, 2H), 7.06 (dd, J = 8.1, 1.6 Hz, 1H), 6.66 (dd, J = 3.4, 0.7 Hz, 1H), 6.60 (dq, J = 3.4, 1.1 Hz, 1H), 4.15 (s, 2H), 3.17 (d, J = 7.0 Hz, 2H), 2.37 (d, J = 1.1 Hz, 3H), 2.26 (td, J = 7.2, 4.5 Hz, 1H), 2.20-2.09 (m, 1H), 1.37-1.28 (m, 2H), 1.21-1.04 (m, 1H), 0.45-0.29 (m, 2H), 0.27-0.15 (m, 2H); MS [M + H]$^+$ = 649 | +++ |
| 131 | 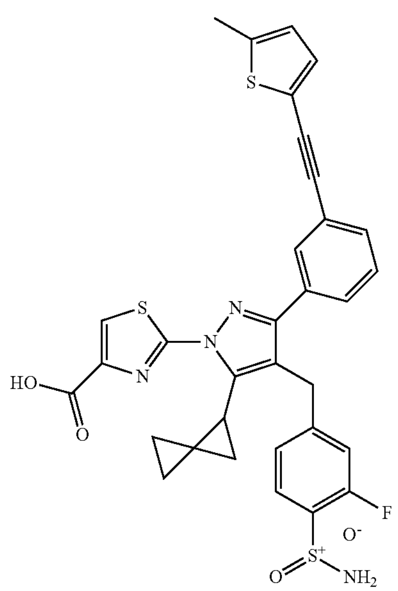 | 2-(4-(3-fluoro-4-sulfamoylbenzyl)-3-(3-((5-methylthiophen-2-yl)ethynyl)phenyl)-5-(spiro[2.2]pentan-1-yl)-1H-pyrazol-1-yl)thiazole-4-carboxylic acid, 1H NMR (400 MHz, DMSO-d6) δ 13.16 (s, 1H), 8.30 (d, J = 4.1 Hz, 1H), 7.71-7.59 (m, 2H), 7.59-7.37 (m, 5H), 7.21 (ddd, J = 3.6, 2.7, 0.5 Hz, 1H), 7.13 (ddd, J = 11.4, 8.2, 1.6 Hz, 1H), 7.03 (dd, J = 8.1, 3.1, 1.6 Hz, 1H), 6.81 (dq, J = 3.3, 1.1 Hz, 1H), 4.21 (t, J = 8.9 Hz, 2H), 3.73 (s, 1H), 3.57 (s, 1H), 2.70-2.59 (m, 1H), 2.45 (p, J = 0.5 Hz, 3H), 1.50 (ddd, J = 8.8, 5.4, 3.4 Hz, 1H), 1.39 (dd, J = 7.8, 4.5 Hz, 1H), 1.18 (t, J = 4.9 Hz, 1H), 0.67 (ddd, J = 8.7, 5.2, 3.5 Hz, 1H), 0.52 (dt, J = 9.0, 4.4 Hz, 1H), 0.48-0.41 (m, 1H), 0.18 (dt, J = 9.2, 4.5 Hz, 1H); MS [M + H]$^+$ = 645 | +++ |

TABLE 7-continued

| Cmpd ID | Structure | Compound name and physical data | Inhibitory activity IC$_{50}$ (μM) |
|---------|-----------|----------------------------------|-----------------------------------|
| 132 | 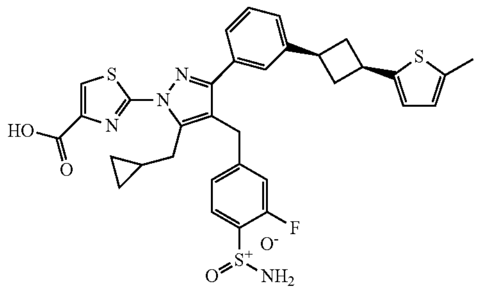 | 2-(5-(cyclopropylmethyl)-4-(3-fluoro-4-sulfamoylbenzyl)-3-(3-((cis)-3-(5-methylthiophen-2-yl)cyclobutyl)phenyl)-1H-pyrazol-1-yl)thiazole-4-carboxylic acid, 1H NMR (400 MHz, Methanol-d4) δ 13.14 (s, 1H), 8.29 (s, 1H), 7.65 (t, J = 7.9 Hz, 1H), 7.56 (s, 2H), 7.45-7.31 (m, 3H), 7.27 (dtd, J = 7.1, 1.7, 0.6 Hz, 1H), 7.13 (dd, J = 11.3, 1.6 Hz, 1H), 7.06 (dd, J = 8.1, 1.6 Hz, 1H), 6.69-6.54 (m, 2H), 4.15 (s, 2H), 3.65-3.51 (m, 1H), 3.42 (tt, J = 10.1, 7.8 Hz, 1H), 3.16 (d, J = 6.9 Hz, 2H), 2.80-2.64 (m, 2H), 2.39 (d, J = 1.1 Hz, 3H), 2.05 (tdd, J = 10.2, 8.3, 2.7 Hz, 2H), 1.25-1.03 (m, 1H), 0.39-0.30 (m, 2H), 0.26-0.19 (m, 2H); MS [M + H]$^+$ = 663 | +++ |
| 133 | 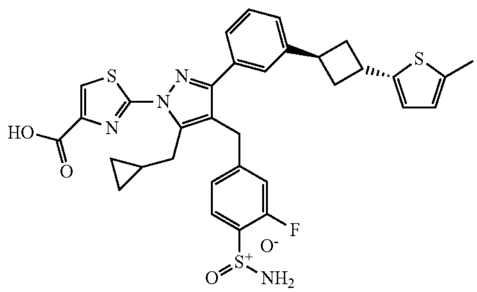 | 2-(5-(cyclopropylmethyl)-4-(3-fluoro-4-sulfamoylbenzyl)-3-(3-(3-(5-methylthiophen-2-yl)cyclobutyl)phenyl)-1H-pyrazol-1-yl)thiazole-4-carboxylic acid, 1H NMR (400 MHz, Methanol-d4) δ 13.14 (s, 1H), 8.28 (s, 1H), 7.66 (t, J = 7.9 Hz, 1H), 7.57 (s, 2H), 7.46-7.38 (m, 2H), 7.39-7.29 (m, 2H), 7.16 (dd, J = 11.4, 1.6 Hz, 1H), 7.07 (dd, J = 8.2, 1.6 Hz, 1H), 6.76 (dd, J = 3.3, 1.1 Hz, 1H), 6.64 (dq, J = 3.4, 1.1 Hz, 1H), 4.16 (s, 2H), 3.64 (qt, J = 13.7, 7.2 Hz, 2H), 3.18 (d, J = 6.9 Hz, 2H), 2.49-2.30 (m, 6H), 1.26-1.08 (m, 1H), 0.42-0.30 (m, 2H), 0.29-0.19 (m, 2H); MS [M + H]$^+$ = 663 | +++ |
| 134 | 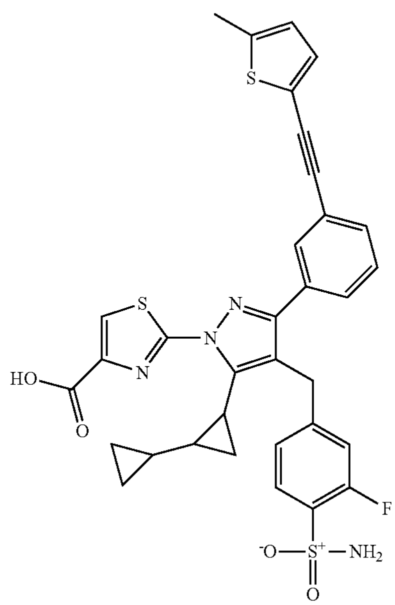 | 2-(5-([1,1'-bi(cyclopropan)]-2-yl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.10 (s, 1H), 8.28 (s, 1H), 7.70-7.61 (m, 2H), 7.60-7.48 (m, 4H), 7.44 (td, J = 7.7, 0.6 Hz, 1H), 7.22 (d, J = 3.6, 0.5 Hz, 1H), 7.17 (dd, J = 11.3, 1.6 Hz, 1H), 7.06 (dd, J = 8.2, 1.6 Hz, 1H), 6.81 (dt, J = 3.5, 1.1 Hz, 1H), 4.12 (s, 2H), 3.19 (q, J = 8.6, 7.9 Hz, 2H), 2.75-2.61 (m, 1H), 2.45 (d, J = 1.1 Hz, 3H), 1.77 (ddq, J = 75.7, 14.6, 7.6 Hz, 2H), 0.75 (ddt, J = 13.1, 8.2, 4.2 Hz, 1H), 0.44 (dq, J = 12.3, 4.3, 3.7 Hz, 1H), 0.36-0.20 (m, 2H), 0.03--0.06 (m, 1H). MS [M + H]$^+$ = 649 | ++ |
| 136 | 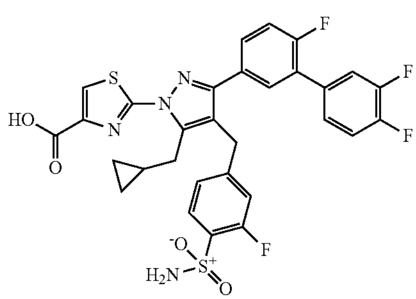 | 2-(5-(cyclopropylmethyl)-4-(3-fluoro-4-sulfamoylbenzyl)-3-(3',4',6-trifluoro-[1,1'-biphenyl]-3-yl)-1H-pyrazol-1-yl)thiazole-4-carboxylic acid. $^1$H NMR (MeOD) δ 8.19 (s, 1H), 7.75 (t, 8.01 Hz, 1H), 7.65-7.61 (m, 1H), 7.54 (dd, J = 2.11, 7.59 Hz, 1H), 7.42-7.37 (m, 1H), 7.35-7.30 (m, 1H), 7.23 (dd, J = 8.43, 10.54 Hz, 1H), 7.12-7.06 (m, 3H), 4.18 (s, 2H), 3.27 (d, J = 6.89 Hz, 2H), 1.18-1.08 (m, 1H), 0.42-0.38 (m, 1H), 0.27-0.23 (m, 1H); MS (ES) m/z 642.9 [M + H]$^+$; LCMS RT = 1.256 min. | +++ |

TABLE 7-continued

| Cmpd ID | Structure | Compound name and physical data | Inhibitory activity IC$_{50}$ (μM) |
|---|---|---|---|
| 137 | 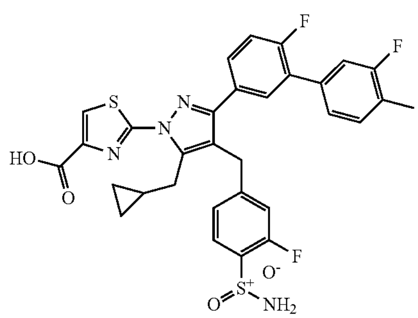 | 2-(5-(cyclopropylmethyl)-3-(3',6-difluoro-4'-methyl-[1,1'-biphenyl]-3-yl)-4-(3-fluoro-4-sulfamoylbenzyl)-1H-pyrazol-1-yl)thiazole-4-carboxylic acid $^1$H NMR (MeOD) δ 8.18 (s, 1H), 7.77-7.73 (m, 1H), 7.61-7.57 (m, 1H), 7.54 (dd, J = 2.15, 7.45 Hz, 1H), 7.28 (t, J = 8.11, 1H), 7.22-7.17 (m, 1H), 7.14 (d, J = 10.91 Hz, 1H), 7.10-7.06 (m, 2H), 7.02 (d, J = 7.83 Hz, 1H), 4.17 (s, 2H), 3.26 (d, J = 6.72 Hz, 2H), 2.30 (d, J = 0.83 Hz, 3H), 1.14-1.09 (m, 1H), 0.41-0.37 (m, 2H), 0.26-0.26 (m, 2H); MS (ES) m/z 639.0 [M + H]$^+$; LCMS RT = 1.287 min. | +++ |
| 138 | 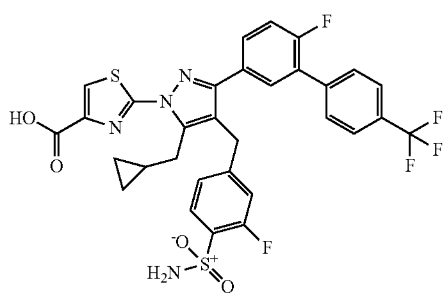 | 2-(5-(cyclopropylmethyl)-3-(6-fluoro-4'-(trifluoromethyl)-[1,1'-biphenyl]-3-yl)-4-(3-fluoro-4-sulfamoylbenzyl)-1H-pyrazol-1-yl)thiazole-4-carboxylic acid. $^1$H NMR (MeOD) δ 8.19 (s 1H) 7.77-7.73 (m, 3H) 7.69-7.65 (m, 2H) 7.59-7.55 (m, 3H), 7.22 (dd, J = 8.66, 10.43 Hz, 1H), 7.09 (s, 1H), 7.07 (d, 2.75 Hz, 1H), 4.18 (s, 2H), 3.27 (d, J = 6.29 Hz, 2H), 1.19-1.09 (m, 1H), 0.42-0.37 (m, 2H), 0.27-0.23 (m, 2H); MS (ES) m/z 674.9 [M + H]$^+$; LCMS RT = 1.316 min. | +++ |
| 139 | 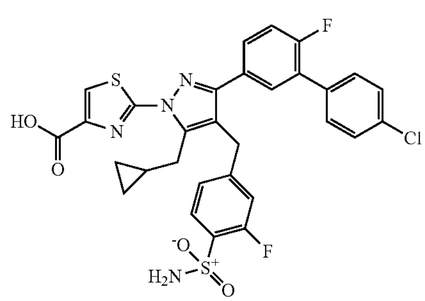 | 2-(3-(4'-chloro-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. MS (ES) m/z 640.9 [M + H]$^+$; LCMS RT = 1.299 min. | +++ |
| 140 | 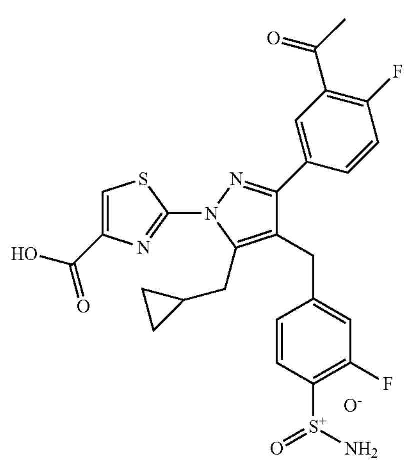 | 2-(3-(3-acetyl-4-fluorophenyl)-5-(cyclopropylmethyl)-4-(3-fluoro-4-sulfamoylbenzyl)-1H-pyrazol-1-yl)thiazole-4-carboxylic acid. MS (ES) m/z 573.0 [M + H]$^+$; LCMS RT = 1.07 min. | +++ |

TABLE 7-continued

| Cmpd ID | Structure | Compound name and physical data | Inhibitory activity IC$_{50}$ (μM) |
|---|---|---|---|
| 141 | 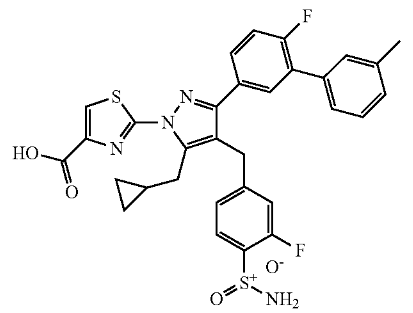 | 2-(5-(cyclopropylmethyl)-3-(6-fluoro-3'-methyl-[1,1'-biphenyl]-3-yl)-4-(3-fluoro-4-sulfamoylbenzyl)-1H-pyrazol-1-yl)thiazole-4-carboxylic acid. $^1$H NMR (MeOD) δ 8.17 (s, 1H), 7.77 (t, J = 15.8 Hz, 1H), 7.59-7.63 (m, 1H), 7.54-7.56 (m, 1H) 7.31 (t, J = 16 Hz, 1H), 7.08-7.23 (m, 7H), 4.19 (s, 2H), 3.32 (d, J = 4 Hz, 2H), 2.35 (s, 3H), 1.11-1.14 (m, 1H), 0.39-0.41 (m, 2H), 0.24-0.25 (m, 2H); MS (ES) m/z 621 [M + H]$^+$; LCMS RT = 1.38 min. | +++ |
| 142 | 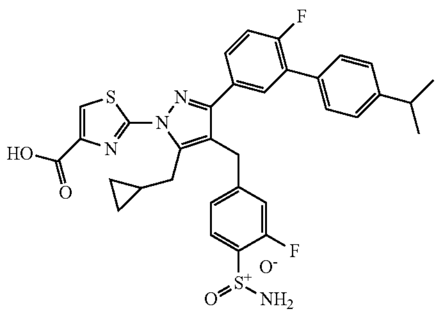 | 2-(5-(cyclopropylmethyl)-3-(6-fluoro-4'-isopropyl-[1,1'-biphenyl]-3-yl)-4-(3-fluoro-4-sulfamoylbenzyl)-1H-pyrazol-1-yl)thiazole-4-carboxylic acid. $^1$H NMR (CDCl$_3$) δ 8.12 (s, 1H), 7.81 (t, J = 16 Hz, 1H), 7.54-7.5 (m, 1H), 7.42-7.46 (m, 1H), 7.38 (d, J = 8 Hz, 2H), 7.31 (d, J = 8 Hz, 2H) 7.13-7.18 (m, 1H), 7.08 (d, J = 8 Hz, 1H), 7.00 (d, J = 8 Hz, 1H), 5.14 (s, 2H), 4.10 (s, 2H), 3.21 (d, J = 8 Hz, 2H), 2.94-3.01 (m, 1H), 1.31 (d, J = 8 Hz, 6H), 1.15-1.18 (m, 1H), 0.46-0.48 (m, 2H), 0.25-0.26 (m, 2H); MS (ES) m/z 649 [M + H]$^+$; LCMS RT = 1.48 min. | ++ |
| 143 | 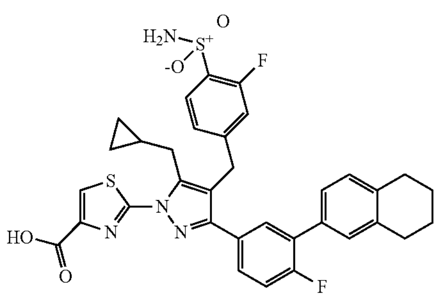 | 2-(5-(cyclopropylmethyl)-3-(4-fluoro-3-(5,6,7,8-tetrahydronaphthalen-2-yl)phenyl)-4-(3-fluoro-4-sulfamoylbenzyl)-1H-pyrazol-1-yl)thiazole-4-carboxylic acid. $^1$H NMR (d$^6$-DMSO) δ 8.29 (s, 1H), 7.81 (t, 1H, J = 4 Hz), 7.62 (s, 2H), 7.51 (d, 1H, J = 2 Hz), 7.35 (t, 1H, J = 8 Hz), 7.21 (d, 1H, J = 12 Hz), 7.13-7.07 (m, 5H), 4.18 (s, 2H), 3.16 (m, 2H), 2.74 (m, 4H), 1.76 (m, 4H), 1.42 (m, 1H), 0.35 (m, 2H), 0.22 (m, 2H); MS (ES) m/z 661 [M + H]$^+$; LCMS RT = 1.39 min. | +++ |
| 144 | 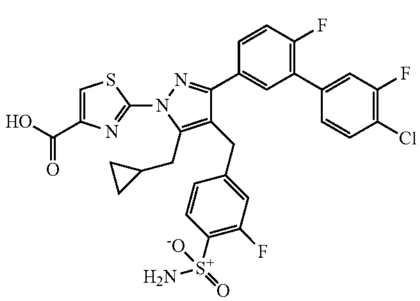 | 2-(3-(4'-chloro-3',6-difluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (CDCl$_3$) δ: 7.99 (s, 1H), 7.74 (t, J = 8.0 Hz, 1H), 7.50 (dd, J = 2.0, 7.6 Hz, 1H), 7.45-7.38 (m, 2H), 7.20 (d, J = 10.0 Hz, 1H), 7.13-7.09 (m, 2H), 7.00 (d, J = 8.1 Hz, 1H), 6.93 (d, J = 11.0 Hz, 1H), 4.03 (s, 2H), 3.15 (d, J = 6.8 Hz, 2H), 1.06-1.03 (m, 1H), 0.39-0.34 (m, 2H), 0.19-0.15 (m, 2H); MS (ES) m/z 659.0 [M + H]$^+$; LCMS RT = 1.298 min. | +++ |
| 145 | 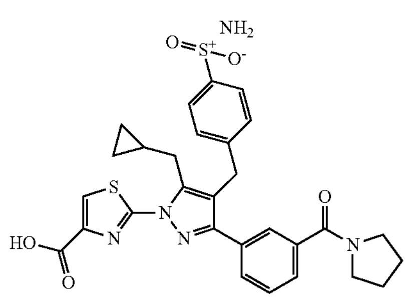 | 2-(5-(cyclopropylmethyl)-3-(3-(pyrrolidine-1-carbonyl)phenyl)-4-(4-sulfamoylbenzyl)-1H-pyrazol-1-yl)thiazole-4-carboxylic acid MS (ES) 628.0 (M + H)+, LCMS RT = 0.968 min. | +++ |

TABLE 7-continued

| Cmpd ID | Structure | Compound name and physical data | Inhibitory activity IC$_{50}$ (μM) |
|---|---|---|---|
| 146 | 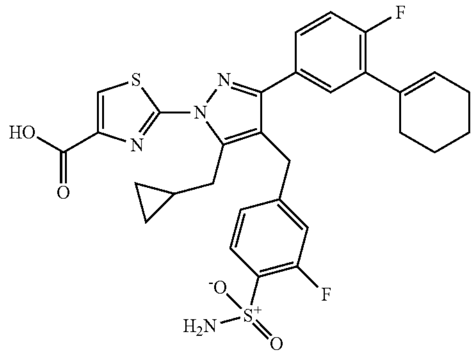 | 2-(5-(cyclopropylmethyl)-3-(6-fluoro-2',3',4',5'-tetrahydro-[1,1'-biphenyl]-3-yl)-4-(3-fluoro-4-sulfamoylbenzyl)-1H-pyrazol-1-yl)thiazole-4-carboxylic acid. $^1$H NMR (d$^6$-DMSO) δ 8.28 (s, 1H), 7.68 (tr, 1H, J = 8 Hz), 7.65 (s, 2H), 7.48-7.46 (m, 1H), 7.29-7.27 (m, 1H), 7.23-7.16 (m, 2H, J = 8 Hz), 5.82 (m, 1H), 4.13 (s, 2H), 3.18-3.16 (m, 2H), 2.16-2.14 (m, 4H), 1.67-1.65 (m, 2H), 1.60-1.57( m, 2H), 1.17-1.15 (m, 1H), 0.37-0.33 (m, 2H), 0.25-0.23 (m, 2H); MS (ES) m/z 611.0 [M + H]$^+$; LCMS RT = 1.30 min. | +++ |
| 147 | 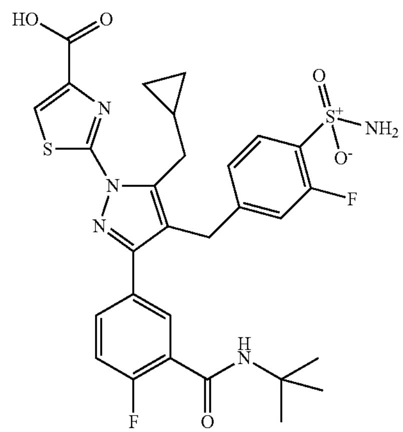 [SMILES: CC(C)(C)NC(=O)c1cc(-c2nn(-c3nc(C(=O)O)cs3)c(CC3CC3)c2Cc2ccc([S+](N)(=O)[O-])c(F)c2)ccc1F] | 2-(3-(3-(tert-butylcarbamoyl)-4-fluorophenyl)-5-(cyclopropylmethyl)-4-(3-fluoro-4-sulfamoylbenzyl)-1H-pyrazol-1-yl)thiazole-4-carboxylic acid: $^1$H-NMR (MeOD) δ: 8.21 (s, 1H), 7.79-7.69 (m, 3H), 7.19 (dd, J = 8.6, 10.0 Hz, 1H), 7.11-7.05 (m, 2H), 4.21 (s, 2H), 3.28 (d, J = 6.8 Hz, 2H), 1.44 (s, 9H), 1.18-1.10 (m, 1H), 0.43-0.39 (m, 2H), 0.28-0.24 (m, 2H); MS (ES) 630.1 [M + H]$^+$, LCMS RT = 1.048 min. | +++ |
| 148 | 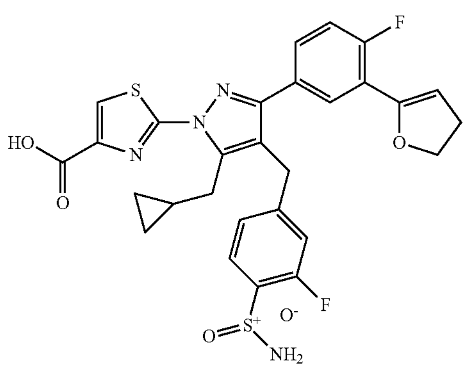 | 2-(5-(cyclopropylmethyl)-3-(3-(4,5-dihydrofuran-2-yl)-4-fluorophenyl)-4-(3-fluoro-4-sulfamoylbenzyl)-1H-pyrazol-1-yl)thiazole-4-carboxylic acid | +++ |
| 149 | 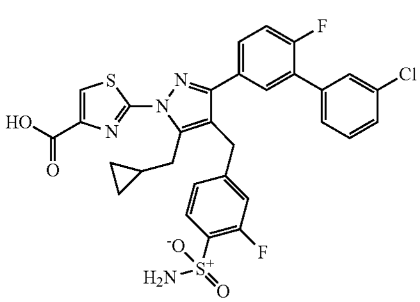 | 2-(3-(3'-chloro-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (CDCl$_3$) δ: 7.97 (s, 1H), 7.63 (t, J = 7.6 Hz, 1H), 7.37-7.31 (m, 2H), 7.20-7.12 (m, 4H), 6.99 (dd, J = 9.2, 10.0 Hz, 1H,), 6.90 (d, J = 8.0 Hz, 1H), 6.81 (d, J = 10.8 Hz, 1H), 3.92 (s, 2H), 3.29 (s, 3H), 3.04 (d, J = 6.7 Hz, 2H), 0.95-0.92 (m, 1H), 0.28-0.23 (m, 2H), 0.07-0.04 (m, 2H). MS (ES) m/z 641.0 [M + H]$^+$; LCMS RT = 1.293 min. | +++ |

TABLE 7-continued

| Cmpd ID | Structure | Compound name and physical data | Inhibitory activity IC$_{50}$ (μM) |
|---|---|---|---|
| 150 | 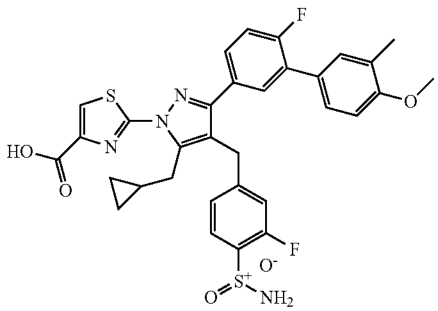 | 2-(5-(cyclopropylmethyl)-3-(6-fluoro-4'-methoxy-3'-methyl-[1,1'-biphenyl]-3-yl)-4-(3-fluoro-4-sulfamoylbenzyl)-1H-pyrazol-1-yl)thiazole-4-carboxylic acid. $^1$H NMR (CDCl$_3$) δ: 8.09 (s, 1H), 7.78 (t, J = 7.6 Hz, 1H), 7.48 (d, J = 7.3 Hz, 1H), 7.26 (bs, 1H), 7.25 (d, J = 6.6 Hz, 2H), 7.17 (d, J = 8.3 Hz, 1H), 7.12 (t, J = 9.4 Hz, 1H), 7.05 (d, J = 8.0 Hz, 1H), 6.98 (d, J = 11.0 Hz, 1H), 6.87 (d, J = 8.4 Hz, 1H), 4.07 (s, 2H), 3.86 (s, 3H), 3.17 (d, J = 6.4 Hz, 2H), 2.24 (s, 3H), 1.13 (bs, 1H), 0.45-0.43 (m, 2H), 0.23-0.22 (m, 2H); MS (ES) m/z 651.0 [M + H]$^+$; LCMS RT = 1.277 min. | +++ |
| 151 | 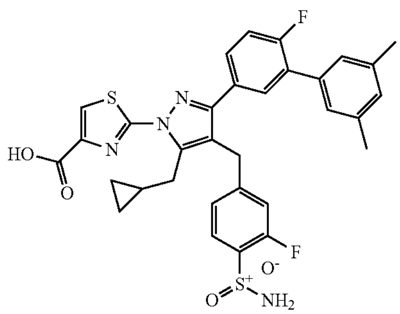 | 2-(5-(cyclopropylmethyl)-3-(6-fluoro-3',5'-dimethyl-[1,1'-biphenyl]-3-yl)-4-(3-fluoro-4-sulfamoylbenzyl)-1H-pyrazol-1-yl)thiazole-4-carboxylic acid. MS (ES) m/z 634.0 [M + H]$^+$; LCMS RT = 1.313 min. | ++ |
| 152 | 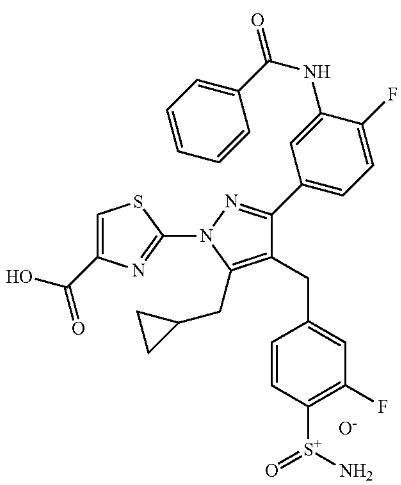 | 2-(3-(3-benzamido-4-fluorophenyl)-5-(cyclopropylmethyl)-4-(3-fluoro-4-sulfamoylbenzyl)-1H-pyrazol-1-yl)thiazole-4-carboxylic acid. MS (ES) m/z 650.0 [M + H]$^+$; LCMS RT = 1.100 min. | +++ |
| 153 | 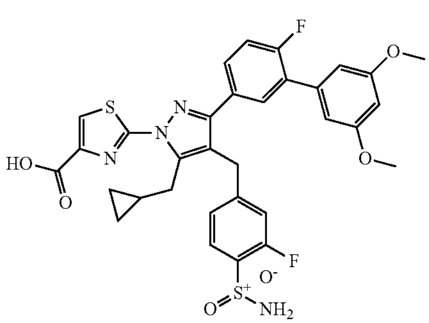 | 2-(5-(cyclopropylmethyl)-3-(6-fluoro-3',5'-dimethoxy-[1,1'-biphenyl]-3-yl)-4-(3-fluoro-4-sulfamoylbenzyl)-1H-pyrazol-1-yl)thiazole-4-carboxylic acid. MS (ES) m/z 666.0 [M + H]$^+$; LCMS RT = 1.223 min. | +++ |

TABLE 7-continued

| Cmpd ID | Structure | Compound name and physical data | Inhibitory activity IC$_{50}$ (μM) |
|---|---|---|---|
| 154 | 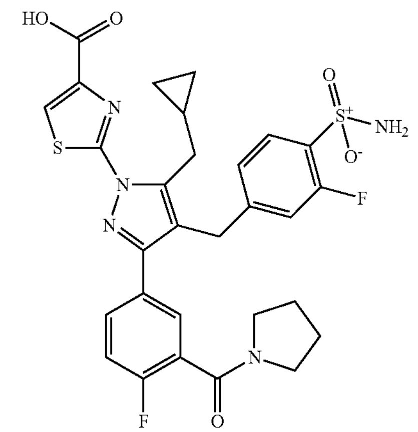 [SMILES: N[S+](=O)([O-])c1ccc(Cc2c(-c3ccc(F)c(C(=O)N4CCCC4)c3)nn(-c3nc(C(=O)O)cs3)c2CC2CC2)cc1F] | 2-(5-(cyclopropylmethyl)-3-(4-fluoro-3-(2-oxopyrrolidin-1-yl)phenyl)-4-(3-fluoro-4-sulfamoylbenzyl)-1H-pyrazol-1-yl)thiazole-4-carboxylic acid. $^1$H NMR (MeOD) δ 8.22 (s, 1H), 7.75-7.71 (m, 2H), 7.54 (dd, J = 2.2, 6.4 Hz, 1H), 7.24 (t, J = 8.8 Hz, 1H), 7.07 (t, J = 7.4 Hz, 2H), 4.20 (s, 2H), 3.59 (t, J = 7.1 Hz, 2H), 3.30 (d, J = 6.9 Hz, 2H), 3.19 (t, J = 2H), 2.03-1.91 (m, 4H), 0.95-0.86 (m, 1H), 0.45-0.40 (m, 2H), 0.29-0.25 (m, 2H); MS (ES) m/z 628.0 [M + H]$^+$; LCMS RT = 0.968 min. | +++ |
| 155 | 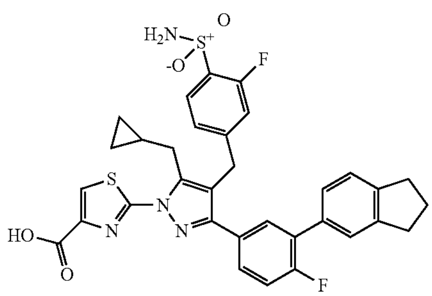 | 2-(5-(cyclopropylmethyl)-3-(3-(2,3-dihydro-1H-inden-5-yl)-4-fluorophenyl)-4-(3-fluoro-4-sulfamoylbenzyl)-1H-pyrazol-1-yl)thiazole-4-carboxylic acid. MS (ES) m/z 647.0 [M + H]$^+$; LCMS RT = 1.34 min. | +++ |
| 156 | 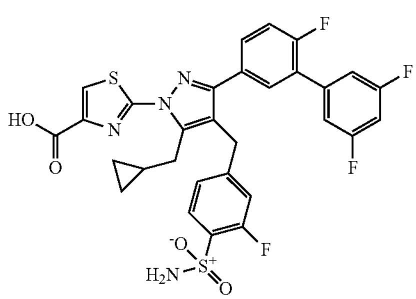 | 2-(5-(cyclopropylmethyl)-4-(3-fluoro-4-sulfamoylbenzyl)-3-(3',5',6-trifluoro-[1,1'-biphenyl]-3-yl)-1H-pyrazol-1-yl)thiazole-4-carboxylic acid. MS (ES) m/z 642.0 [M + H]$^+$; LCMS RT = 1.260 min. | +++ |
| 157 | 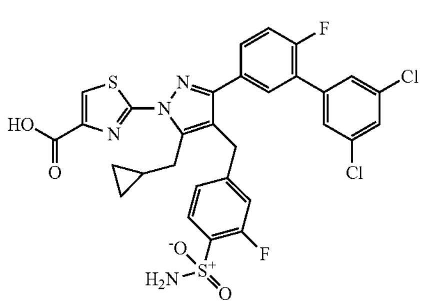 | 2-(5-(cyclopropylmethyl)-3-(3',5'-dichloro-6-fluoro-[1,1'-biphenyl]-3-yl)-4-(3-fluoro-4-sulfamoylbenzyl)-1H-pyrazol-1-yl)thiazole-4-carboxylic acid. MS (ES) m/z 674.0 [M + H]$^+$; LCMS RT = 1.365 min. | ++ |

TABLE 7-continued

| Cmpd ID | Structure | Compound name and physical data | Inhibitory activity IC$_{50}$ (μM) |
|---|---|---|---|
| 158 | 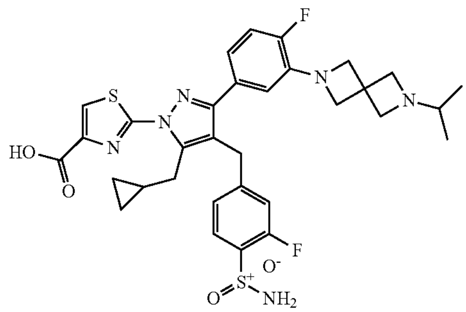 | 2-(5-(cyclopropylmethyl)-3-(4-fluoro-3-(6-isopropyl-2,6-diazaspiro[3.3]heptan-2-yl)phenyl)-4-(3-fluoro-4-sulfamoylbenzyl)-1H-pyrazol-1-yl)thiazole-4-carboxylic acid; $^1$H-NMR (MeOD) δ acid,: 8.19 (s, 1H), 7.79 (t, J = 8.1 Hz, 1H), 7.10 (s, 1H), 7.08 (d, J = 4.8 Hz, 1H), 7.00 (d, J = 8.9 Hz, 2H), 6.28 (d, J = 8.5 Hz, 1H), 4.35 (d, J = 11.7 Hz, 2H), 4.28 (d, J = 11.6 Hz, 2H), 3.70 (s, 2H), 3.45 (p, J = 6.5, 12.8 Hz, 1H), 3.28 (d, J = 6.9 Hz, 2H), 2.66 (s, 2H), 1.24 (d, J = 6.48 Hz, 6H), 1.17-1.12 (m, 1H), 0.34-0.32 (m, 2H), 0.22-0.21 (m, 2H). MS (ES) 669.0 [M + H]$^+$, LCMS RT = 0.970 min. | +++ |
| 159 | 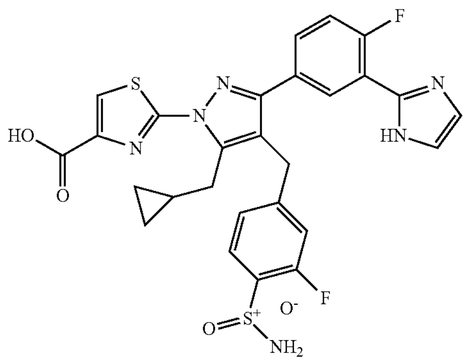 | 2-(5-(cyclopropylmethyl)-3-(4-fluoro-3-(1H-imidazol-2-yl)phenyl)-4-(3-fluoro-4-sulfamoylbenzyl)-1H-pyrazol-1-yl)thiazole-4-carboxylic acid. MS (ES) m/z 597.1 [M + H]$^+$; LCMS RT = 0.863 min. | +++ |
| 160 | 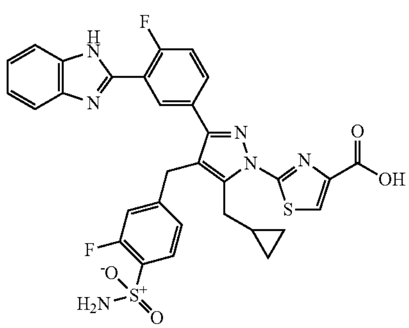 | 2-(3-(3-(1H-benzo[d]imidazol-2-yl)-4-fluorophenyl)-5-(cyclopropylmethyl)-4-(3-fluoro-4-sulfamoylbenzyl)-1H-pyrazol-1-yl)thiazole-4-carboxylic acid. MS (ES) m/z 647.1.0 [M + H]$^+$; LCMS RT = 0.987 min. | +++ |
| 161 | 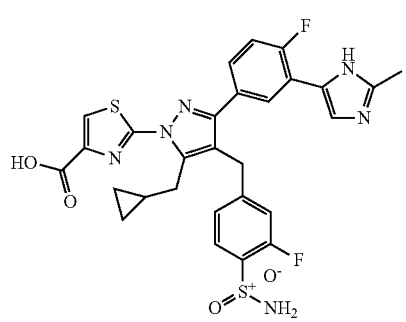 | 2-(5-(cyclopropylmethyl)-3-(4-fluoro-3-(2-methyl-1H-imidazol-5-yl)phenyl)-4-(3-fluoro-4-sulfamoylbenzyl)-1H-pyrazol-1-yl)thiazole-4-carboxylic acid. $^1$H NMR (MeOD) δ: 8.19 (s, 1H), 7.84 (t, J = 6.0 Hz, 1H), 7.68 (t, J = 7.6 Hz, 1H), 7.64 (s, 1H), 7.59 (bs, 1H), 7.31 (t, J = 10.4 Hz, 1H), 7.02 (t, J = 9.6 Hz, 2H), 4.17 (s, 2H), 2.70 (s, 3H), 1.14 (bs, 1H), 0.43-0.41 (m, 2H), 0.27-0.25 (m, 2H). MS (ES) m/z 611.0 [M + H]$^+$; LCMS RT = 0.912 min. | +++ |

TABLE 7-continued

| Cmpd ID | Structure | Compound name and physical data | Inhibitory activity IC$_{50}$ (μM) |
|---|---|---|---|
| 162 | 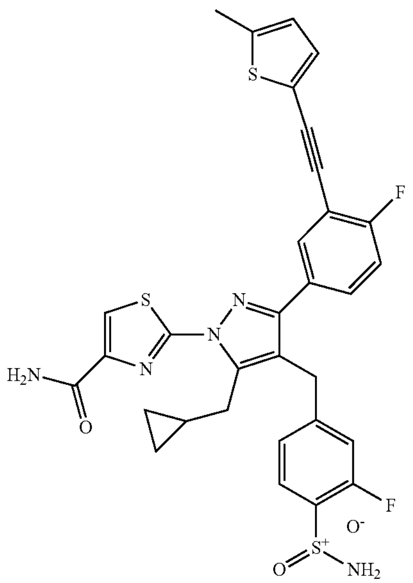 | 2-(5-(cyclopropylmethyl)-3-(4-fluoro-3-((5-methylthiophen-2-yl)ethynyl)phenyl)-4-(3-fluoro-4-sulfamoylbenzyl)-1H-pyrazol-1-yl)thiazole-4-carboxamide; $^{1}$H-NMR (d$_{6}$-DMSO) δ 8.13 (s, 1H), 7.75-7.54 (m, 3H), 7.62 (s, 2H), 7.38 (tr, 1H, J = 16 Hz), 7.36 (d, 1H, J = 4 Hz), 7.15 (d, 1H, J = 12 Hz), 7.06 (d, 1H, J = 8 Hz), 6.85 (d, 1H, J = 4 Hz), 4.18 (s, 2H), 3.18-315 (m, 2H), 2.5 (s, 3H), 1.18-1.15 (m, 1H), 0.34-0.32 (m, 2H), 0.19-0.17 (m, 2H); MS (ES) 651.1 [M + H]$^{+}$, LCMS RT = 0.78 min. | +++ |
| 164 | 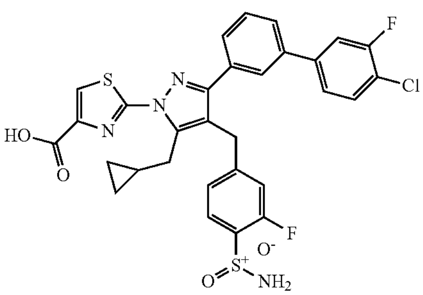 | 2-(3-(4'-chloro-3'-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^{1}$H NMR (MeOD) δ 8.20 (s, 1H), 7.76 (t, J = 7.76 Hz, 1H), 7.70 (t, J = 1.63 Hz, 1H), 7.62 (dd, J = 1.63, 7.76 Hz, 2H), 7.52 (t, J = 8.17 Hz, 1H), 7.48 (t, J = 7.84 Hz, 1H), 7.43 (dd, J = 2.05, 10.59 Hz, 1H), 7.21 (dd, J = 1.71, 8.41 Hz, 1H), 7.12-7.07 (m, 2H), 4.20 (s, 2H), 3.28 (d, J = 6.39 Hz, 2H), 1.19-1.09 (m, 1H), 0.43-0.38 (m, 2H), 0.27-0.23 (m, 2H); MS (ES) m/z 640.9 [M + H]$^{+}$, LCMS RT = 1.432 min. | +++ |
| 165 | 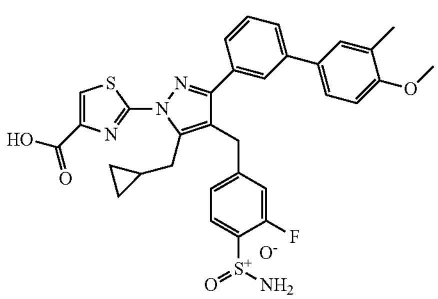 | 2-(5-(cyclopropylmethyl)-4-(3-fluoro-4-sulfamoylbenzyl)-3-(4'-methoxy-3'-methyl-[1,1'-biphenyl]-3-yl)-1H-pyrazol-1-yl)thiazole-4-carboxylic acid. $^{1}$H NMR (MeOD) δ 8.19 (s, 1H), 7.79-7.76 (m, 1H), 7.58-7.51 (m, 3H), 7.40 (t, J = 7.69 Hz, 1H), 7.25 (d, J = 1.81 Hz, 1H), 7.14-7.09 (m, 3H), 6.93 (d, J = 8.50 Hz, 1H), 4.17 (s, 2H), 3.85 (s, 3H), 3.26 (d, J = 6.65 Hz, 2H), 2.22 (s, 3H), 1.18-1.08 (m, 1H), 0.42-0.37 (m, 2H), 0.26-0.22 (m, 2H); MS (ES) m/z 633.0 [M + H]$^{+}$, LCMS RT = 1.412 min. | +++ |
| 166 | 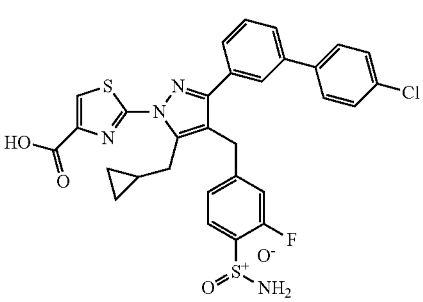 | 2-(3-(4'-chloro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^{1}$H NMR (MeOD) δ 8.20 (s, 1H), 7.77 (t, J = 8.02 Hz, 1H), 7.63 (dd, J = 1.50, 12.98 Hz, 2H), 7.59 (d, J = 1.43 Hz, 1H), 7.46 (t, J = 7.72 Hz, 1H), 7.41 (s, 4H), 7.11-7.08 (m, 2H), 4.19 (s, 2H), 3.27 (d, J = 6.85 Hz, 2H), 1.19-1.09 (m, 1H), 0.42-0.38 (m, 2H), 0.27-0.23 (m, 2H); MS (ES) m/z 622.9 [M + H]$^{+}$, RT = 1.261 min. | +++ |

TABLE 7-continued

| Cmpd ID | Structure | Compound name and physical data | Inhibitory activity IC$_{50}$ (μM) |
|---|---|---|---|
| 167 | 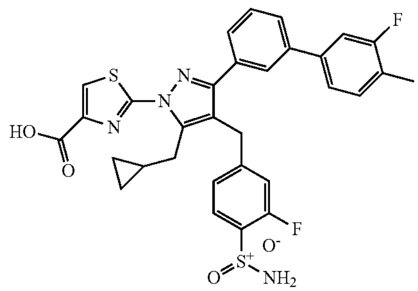 | 2-(5-(cyclopropylmethyl)-3-(3'-fluoro-4'-methyl-[1,1'-biphenyl]-3-yl)-4-(3-fluoro-4-sulfamoylbenzyl)-1H-pyrazol-1-yl)thiazole-4-carboxylic acid. $^1$H NMR (MeOD) δ 8.19 (s, 1H), 7.78-7.74 (m, 1H), 7.67 (t, J = 1.52, 1H), 7.60-7.56 (m, 2H), 7.44 (t, J = 7.82 Hz, 1H), 7.27 (t, J = 8.04 Hz, 1H), 7.19 (dd, J = 1.70, 11.21 Hz, 1H), 7.12-7.08 (m, 3H), 4.19 (s, 2H), 3.27 (d, J = 6.83 Hz, 2H), 2.28 (d, J = 1.42 Hz, 3H), 1.18-1.08 (m, 1H), 0.42-0.37 (m, 2H), 0.27-0.23 (m, 2H); MS (ES) m/z 621.0 [M + H]$^+$, LCMS RT = 1.256 min | +++ |
| 168 | 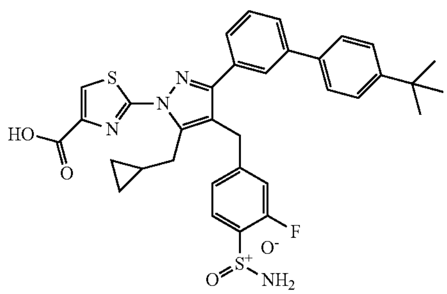 | 2-(3-(4'-(tert-butyl)-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (MeOD) δ 8.17 (s, 1H), 7.79-7.75 (m, 1H), 7.63-7.62 (m, 1H), 7.59 (d, J = 7.82 Hz, 1H), 7.53 (d, J = 7.82 Hz, 1H), 7.45-7.39 (m, 3H), 7.32 (d, J = 8.50 Hz, 2H), 7.10 (s, 1H), 7.08 (d, J = 3.84 Hz, 1H), 4.15 (s, 2H), 3.25 (d, J = 6.72 Hz, 2H), 1.34 (s, 9H), 1.18-1.08 (m, 1H), 0.41-0.36 (m, 2H), 0.26-0.22 (m, 2H); MS (ES) m/z 645.0 [M + H]$^+$; LCMS RT = 1.348 min. | ++ |
| 169 | 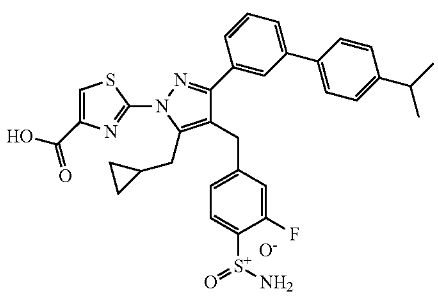 | 2-(5-(cyclopropylmethyl)-4-(3-fluoro-4-sulfamoylbenzyl)-3-(4'-isopropyl-[1,1'-biphenyl]-3-yl)-1H-pyrazol-1-yl)thiazole-4-carboxylic acid. $^1$H NMR (MeOD) δ 8.18 (s, 1H), 7.79-7.75 (m, 1H), 7.64 (t, J = 1.49 Hz, 1H), 7.57 (dd, J = 7.75, 19.38 Hz, 2H), 7.42 (t, J = 7.75 Hz, 1H), 7.33 (d, J = 8.35 Hz, 2H), 7.28 (d, J = 8.35 Hz, 2H), 7.11-7.08 (m, 2H), 4.17 (s, 2H), 3.21 (d, J = 6.71 Hz, 2H), 2.97-2.87 (m, 1H), 1.27 (d, J = 6.86 Hz, 6H), 1.18-1.08 (m, 1H), 0.41-0.37 (m, 2H), 0.26-0.22 (m, 2H); MS (ES) m/z 631.0 [M + H]$^+$; LCMS RT = 1.313 min. | +++ |
| 172 | 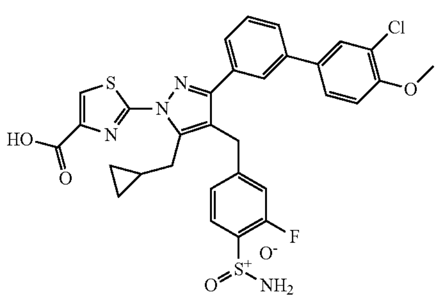 | 2-(3-(3'-chloro-4'-methoxy-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (MeOD) δ: 8.14 (s, 1H), 7.60 (t, J = 7.72 Hz, 1H), 7.12 (t, J = 8.4 Hz, 2H), 7.03-6.79 (m, 6H), 6.77 (d, J = 1.9 Hz, 1H), 4.09 (s, 2H), 3.78 (s, 3H), 3.15 (d, J = 6.1 Hz, 2H), 0.99 (bs, 1H), 0.28-0.25 (m, 2H), 0.10-0.09 (m, 2H). | ++ |
| 173 | 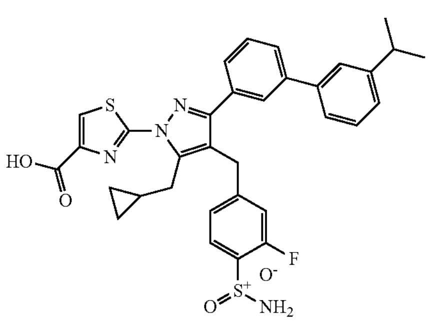 | 2-(5-(cyclopropylmethyl)-4-(3-fluoro-4-sulfamoylbenzyl)-3-(3'-isopropyl-[1,1'-biphenyl]-3-yl)-1H-pyrazol-1-yl)thiazole-4-carboxylic acid. $^1$H NMR (CDCl$_3$) δ 8.11 (s, 1H), 7.80 (t, J = 7.71 Hz, 1H), 7.67 (s, 1H), 7.61 (d, J = 6.72 Hz, 1H), 7.48-7.42 (m, 1H), 7.37-7.34 (m, 2H), 7.28-7.22 (m, 2H), 7.08 (d, J = 7.96 Hz, 1H), 7.00 (d, J = 10.95 Hz, 1H), 4.11 (s, 2H), 3.17 (d, J = 6.47 Hz, 2H), 3.00-2.90 (m, 1H), 1.29 (d, J = 6.97 Hz, 6H), 1.22-1.12 (m, 1H), 0.50-0.46 (m, 2H), 0.25-0.22 (m, 2H); MS (ES) m/z 631.0 [M + H]$^+$; LCMS RT = 1.359 min. | +++ |

TABLE 7-continued

| Cmpd ID | Structure | Compound name and physical data | Inhibitory activity IC$_{50}$ (μM) |
|---|---|---|---|
| 174 | 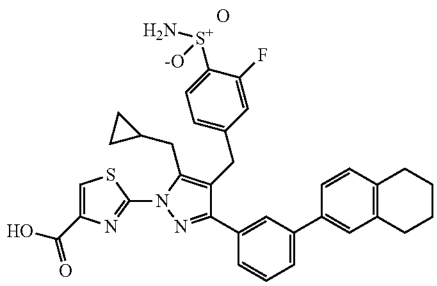 | 2-(5-(cyclopropylmethyl)-4-(3-fluoro-4-sulfamoylbenzyl)-3-(3-(5,6,7,8-tetrahydronaphthalen-2-yl)phenyl)-1H-pyrazol-1-yl)thiazole-4-carboxylic acid. $^1$H NMR (CDCl$_3$) δ 8.10 (s, 1H), 7.79 (t, J = 7.85 Hz, 1H), 7.61 (s, 1H), 7.58 (d, J = 6.90 Hz, 1H), 7.46-7.40 (m, 2H), 7.18 (s, 2H), 7.13-7.11 (m, 1H), 7.07 (d, J = 8.08 Hz, 1H), 6.98 (d, J = 10.94 Hz, 1H), 4.10 (s, 2H), 3.17 (d, J = 6.56 Hz, 2H), 2.80 (s, 4H), 1.83 (s, 4H), 1.23-1.13 (m, 1H), 0.51-0.46 (m, 2H), 0.25-0.21 (m, 2H); MS (ES) m/z 643.0 [M + H]$^+$; LCMS RT = 1.377 min. | ++ |
| 175 | 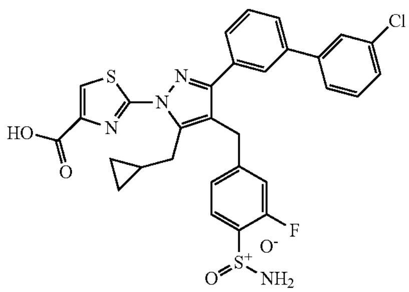 | 2-(3-(3'-chloro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (MeOD) δ 8.21 (s, 1H), 7.77 (t, J = 7.84 Hz, 1H), 7.69 (t, J = 1.63 Hz, 1H), 7.65-7.59 (m, 3H), 7.53 (t, J = 1.81, 1H), 7.48 (t, J = 7.72 Hz, 1H), 7.45-7.39 (m, 2H), 7.37-7.34 (m, 2H), 7.34-7.32 (m, 1H), 7.14-7.08 (m, 2H), 4.22 (s, 2H), 3.28 (d, J = 6.85 Hz, 2H), 1.19-1.09 (m, 1H), 0.43-0.38 (m, 2H), 0.27-0.24 (m, 2H); MS (ES) m/z 623.0 [M + H]$^+$; LCMS RT = 1.364 min. | +++ |
| 176 | 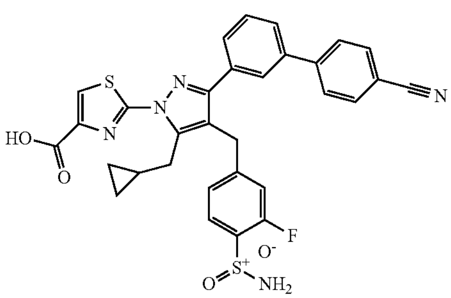 | 2-(3-(4'-cyano-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (CDCl$_3$) δ 8.11 (s, 1H), 7.82 (t, J = 7.60 Hz, 1H), 7.74-7.72 (m, 3H), 7.61-7.60 (m, 1H), 7.57 (d, J = 8.54 Hz, 2H), 7.53-7.50 (m,. 1H), 7.49 (d, J = 7.46 Hz, 1H), 7.07 (d, J = 8.21 Hz, 1H), 7.01 (d, 11.07 Hz, 1H), 4.11 (s, 2H), 3.18 (d, J = 6.87 Hz, 2H), 1.22-1.12 (m, 1H), 0.51-0.47 (m, 2H), 0.25-0.21 (m, 2H); MS (ES) m/z 631.0 [M + H]$^+$: LCMS RT = 1.167 min. | +++ |
| 177 | 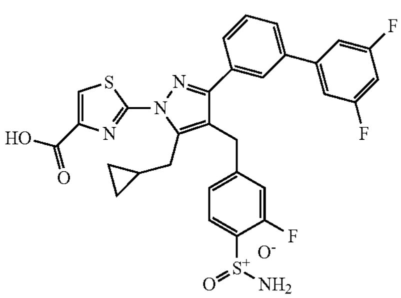 | 2-(5-(cyclopropylmethyl)-3-(3',5-difluoro-[1,1'-biphenyl]-3-yl)-4-(3-fluoro-4-sulfamoylbenzyl)-1H-pyrazol-1-yl)thiazole-4-carboxylic acid. $^1$H NMR (CDCl$_3$) δ 8.20 (s, 1H), 7.77-7.73 (m, 2H), 7.64-7.61 (m, 2H), 7.48 (t, J = 7.74 Hz, 1H), 7.16-7.12 (m, 2H), 7.11-7.06 (m, 2H), 6.93 (tt, J = 2.26, 9.05 Hz, 1H), 4.22 (s, 2H), 3.27 (d, J = 6.79 Hz, 2H), 1.18-1.08 (m, 1H), 0.42-0.38 (m, 2H), 0.27-0.23 (m, 2H); MS (ES) m/z 614.2 [M + H]$^+$; LCMS RT = 0.954 min. | +++ |
| 178 | 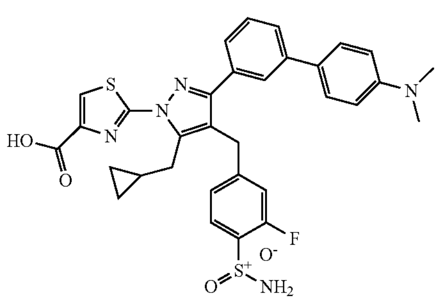 | 2-(5-(cyclopropylmethyl)-3-(4'-(dimethylamino)-[1,1'-biphenyl]-3-yl)-4-(3-fluoro-4-sulfamoylbenzyl)-1H-pyrazol-1-yl)thiazole-4-carboxylic acid. $^1$H NMR (MeOD) δ: 8.21 (s, 1H), 7.79 (t, J = 7.5 Hz, 1H), 7.59 (t, J = 9.0 Hz, 2H), 7.49-7.44 (m, 2H), 7.17-7.15 (m, 2H), 7.12 (d, J = 2.42 Hz, 1H), 4.18 (s, 2H), 3.13 (s, 6H), 1.19-1.12 (m, 1H), 0.44-0.40 (m, 2H), 0.28-0.25 (m, 2H); MS (ES) m/z 632.0 [M + H]$^+$; LCMS RT 0.943 min. | +++ |

TABLE 7-continued

| Cmpd ID | Structure | Compound name and physical data | Inhibitory activity IC$_{50}$ (μM) |
|---|---|---|---|
| 182 | 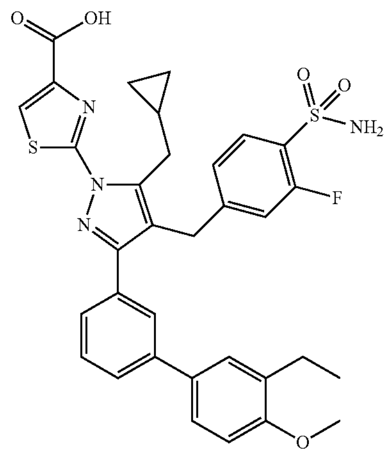 [SMILES: CCc1cc(-c2cccc(-c3nn(-c4nc(C(=O)O)cs4)c(CC4CC4)c3Cc3ccc(S(N)(=O)=O)c(F)c3)c2)ccc1OC] | 2-(5-(cyclopropylmethyl)-3-(3'-ethyl-4'-methoxy-[1,1'-biphenyl]-3-yl)-4-(3-fluoro-4-sulfamoylbenzyl)-1H-pyrazol-1-yl)thiazole-4-carboxylic acid: $^1$H NMR (MeOD) δ: 8.18 (s, 1H), 7.78 (t, J = 7.9 Hz, 1H), 7.62 (s, 1H), 7.59-7.52 (m, 2H), 7.43 (t, J = 7.7, 1H), 7.28 (d, J = 2.4 Hz, 2H), 7.16-7.10 (m, 3H), 6.96-(d, J = 8.55 Hz, 1H), 4.20 (s, 2H), 3.86 (s, 3H), 2.65 (q, J = 7.55, 15.09 Hz, 2H), 1.19 (t, J = 7.55 Hz), 1.15-1.10 (m, 1H), 0.42-0.38 (m, 2H), 0.26-0.23 (m, 2H); MS (ES) m/z 647.0 [M + H]$^+$; LCMS RT = 1.296 min. | ++ |
| 183 | 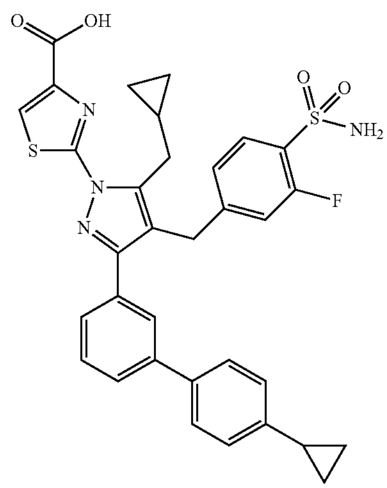 [SMILES: NS(=O)(=O)c1ccc(Cc2c(-c3cccc(-c4ccc(C5CC5)cc4)c3)nn(-c3nc(C(=O)O)cs3)c2CC2CC2)cc1F] | 2-(3-(4'-cyclopropyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (MeOD) δ: 8.19 (s, 1H), 7.77 (t, J = 7.6 Hz, 1H), 7.61 (t, J = 1.6 Hz, 1H), 7.59-7.53 (m, 2H), 7.42 (t, J = 7.71, 1H), 7.29-7.27 (m, 2H), 7.12-7.08 (m, 4H), 4.17 (s, 2H), 3.26 (d, J = 6.73 Hz, 2H), 1.95-1.88 (m, 1H), 1.16-1.11 (m, 1H), 1.00-0.95 (m, 2H), 0.74-0.70 (m, 2H), 0.42-0.38 (m, 2H), 0.27-0.23 (m, 2H); MS (ES) m/z 629.0 [M + H]$^+$; LCMS RT = 1.301 min. | +++ |
| 184 | 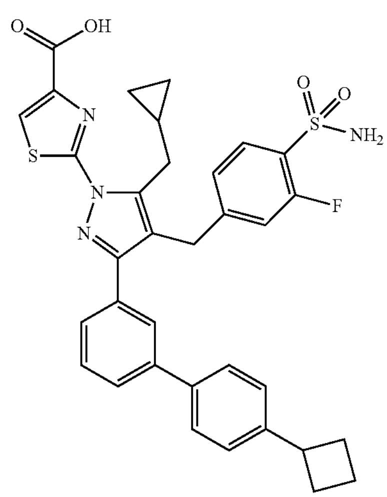 [SMILES: NS(=O)(=O)c1ccc(Cc2c(-c3cccc(-c4ccc(C5CCC5)cc4)c3)nn(-c3nc(C(=O)O)cs3)c2CC2CC2)cc1F] | 2-(3-(4'-cyclobutyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (MeOD) δ: 8.19 (s, 1H), 7.78 (t, J = 7.8 Hz, 1H), 7.65 (s, 1H), 7.61-7.55 (m, 2H), 7.44 (t, J = 7.7, 1H), 7.35 (d, J = 8.1 Hz, 2H), 7.29-7.27 (m, 2H), 7.13-7.09 (m, 2H), 4.20 (s, 2H), 3.60-3.54 (m, 1H), 3.28 (d, J = 7.32 Hz, 2H), 2.40-2.33 (m, 2H), 2.21-2.14 (m, 2H), 2.09-2.02 (m, 1H), 1.93-1.88 (m, 1H), 1.16-1.11 (m, 1H), 0.41-0.38 (m, 2H), 0.27-0.23 (m, 2H); MS (ES) m/z 643.0 [M + H]$^+$; LCMS RT = 1.380 min. | ++ |

TABLE 7-continued

| Cmpd ID | Structure | Compound name and physical data | Inhibitory activity IC$_{50}$ (μM) |
|---|---|---|---|
| 185 | 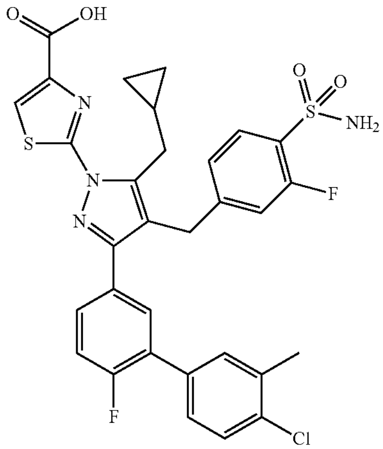 | 2-(3-(4'-chloro-6-fluoro-3'-methyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid: - $^1$H NMR (MeOD) δ: 8.19 (s, 1H), 7.75 (t, J = 7.9 Hz, 1H), 7.65-7.61 (m, 1H), 7.54 (dd, J – 2.19, 7.37 Hz, 1H), 7.34 (bs, 1H), 7.22 (dd, J = 8.63, 10.59 Hz, 1H), 7.18 (d, = 9.55 Hz, 1H), 7.10 (bs, 1H), 7.08 (d, J = 4.03 Hz, 1H), 4.19 (s, 2H), 3.27 (d, J = 6.85 Hz, 2H), 2.41 (s, 3H), 1.16-1.10 (m, 1H), 0.42-0.37 (m, 2H), 0.26-0.23 (m, 2H); MS (ES) m/z 665.0 [M + H]$^+$; LCMS RT = 1.307 min. | ++ |
| 186 | 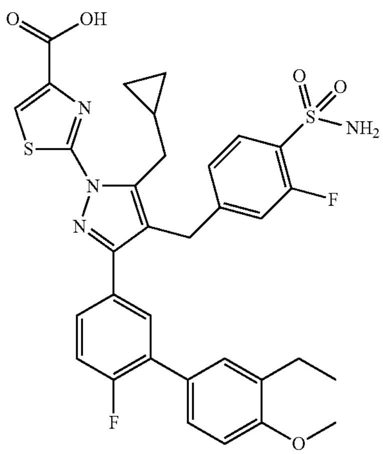 | 2-(5-(cyclopropylmethyl)-3-(3'-ethyl-6-fluoro-4'-methoxy-[1,1'-biphenyl]-3-yl)-4-(3-fluoro-4-sulfamoylbenzyl)-1H-pyrazol-1-yl)thiazole-4-carboxylic acid: MS (ES) m/z 654.9 [M + H]$^+$; LCMS RT = 1.322 min. | ++ |
| 187 | 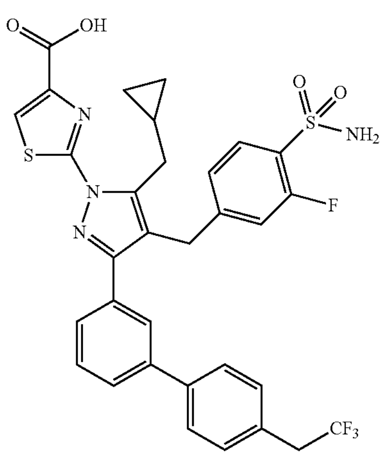 [SMILES: NS(=O)(=O)c1ccc(Cc2c(-c3cccc(-c4ccc(CC(F)(F)F)cc4)c3)nn(-c3nc(C(=O)O)cs3)c2CC2CC2)cc1F] | 2-(5-(cyclopropylmethyl)-4-(3-fluoro-4-sulfamoylbenzyl)-3-(4'-(2,2,2-trifluoroethyl)-[1,1'-biphenyl]-3-yl)-1H-pyrazol-1-yl)thiazole-4-carboxylic acid: $^1$H NMR (MeOD) δ: 8.20 (s, 1H), 7.77 (t, J = 8.0 Hz, 1H), 7.69 (bs, 1H), 7.64-7.59 (m, 2H), 7.46 (dd, J – 8.4, 10.5 Hz, 1H), 7.43 (bs, 1H), 7.40-7.39 (m, 2H), 7.13-7.09 (m, 2H), 4.20 (s, 2H), 3.51 (1, J – 11.1, 22.2 Hz, 2H) 3.28 (d, J = 7.0 Hz, 2H), 1.17-1.11 (m, 1H), 0.43-0.38 (m, 2H), 0.27-0.24 (m, 2H); MS (ES) m/z 671.0 [M + H]$^+$; LCMS RT = 1.252 min. | ++ |

TABLE 7-continued

| Cmpd ID | Structure | Compound name and physical data | Inhibitory activity IC$_{50}$ (µM) |
|---|---|---|---|
| 188 | 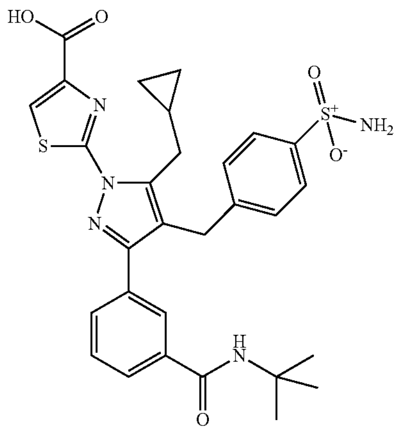 [SMILES: CC(C)(C)NC(=O)c1cccc(-c2nn(-c3nc(C(=O)O)cs3)c(CC3CC3)c2Cc2ccc([S+](N)(=O)[O-])cc2)c1] | 2-(3-(3-(tert-butylcarbamoyl)phenyl)-5-(cyclopropylmethyl)-4-(4-sulfamoylbenzyl)-1H-pyrazol-1-yl)thiazole-4-carboxylic acid: MS (ES) 594.0 [M + H]$^+$, LCMS RT = 1.062 min. | +++ |
| 189 | 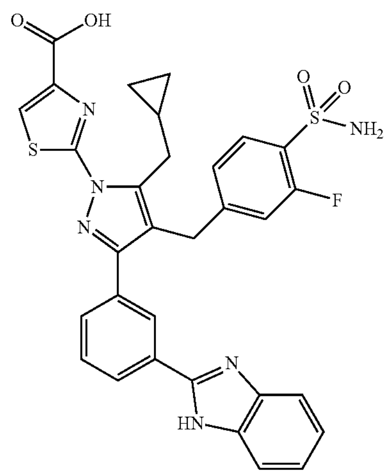 [SMILES: NS(=O)(=O)c1ccc(Cc2c(-c3cccc(-c4nc5ccccc5[nH]4)c3)nn(-c3nc(C(=O)O)cs3)c2CC2CC2)cc1F] | 2-(3-(3-(1H-benzo[d]imidazol-2-yl)phenyl)-5-(cyclopropylmethyl)-4-(3-fluoro-4-sulfamoylbenzyl)-1H-pyrazol-1-yl)thiazole-4-carboxylic acid: MS (ES) m/z 629.0 [M + H]$^+$; LCMS RT = 0.875 min. | +++ |
| 190 | 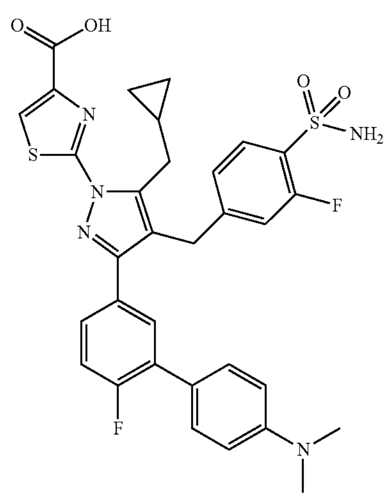 [SMILES: CN(C)c1ccc(-c2cc(-c3nn(-c4nc(C(=O)O)cs4)c(CC4CC4)c3Cc3ccc(S(N)(=O)=O)c(F)c3)ccc2F)cc1] | 2-(5-(cyclopropylmethyl)-3-(4'-(dimethylamino)-6-fluoro-[1,1'-biphenyl]-3-yl)-4-(3-fluoro-4-sulfamoylbenzyl)-1H-pyrazol-1-yl)thiazole-4-carboxylic acid: MS (ES) m/z 649.0 [M + H]$^+$; LCMS RT = 1.065 min. | +++ |

TABLE 7-continued

| Cmpd ID | Structure | Compound name and physical data | Inhibitory activity IC$_{50}$ (μM) |
|---|---|---|---|
| 191 | 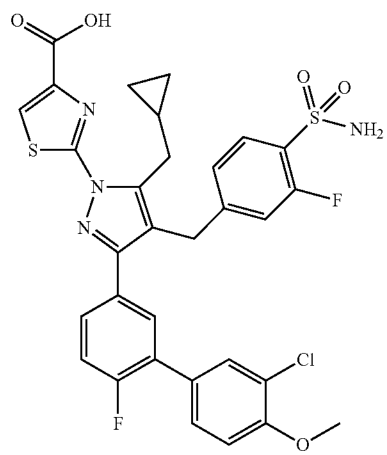 [SMILES: COc1ccc(-c2cc(-c3nn(-c4nc(C(=O)O)cs4)c(CC4CC4)c3Cc3ccc(S(N)(=O)=O)c(F)c3)ccc2F)cc1Cl] | 2-(3-(3'-chloro-6-fluoro-4'-methoxy-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (400 MHz, CDCl3): δ 8.14 (s, 1H), 7.86 (t, J = 16 Hz, 1H), 7.42-7.53 (m, 3H), 7.24-7.27 (m, 1H), 7.18 (t, J = 16 Hz, 1H), 7.10 (d, J = 8 Hz, 1H), 6.99-7.05 (m, 2H), 5.02 (s, 2H), 4.10 (s, 2H), 4.00 (s, 3H), 3.185 (d, J = 4 Hz, 2H), 1.15-1.18 (m, 1H), 0.47-0.51 (m, 2H), 0.24-0.26 (m, 2H); MS (ES) m/z 671 [M + H]$^+$; LCMS RT = 1.38 min. | +++ |
| 192 | 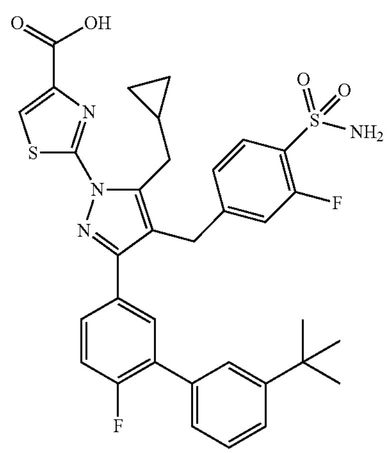 [SMILES: CC(C)(C)c1cccc(-c2cc(-c3nn(-c4nc(C(=O)O)cs4)c(CC4CC4)c3Cc3ccc(S(N)(=O)=O)c(F)c3)ccc2F)c1] | 2-(3-(3'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (MeOD) δ 8.20 (s, 1 H), 7.77 (t, J = 7.90 Hz, 1H), 7.62-7.59 (m, 2H), 7.52 (d, J = 1.65 Hz, 1H), 7.45-7.42 (m, 1H), 7.37 (t, J = 7.90 Hz, 1H), 7.24-1.19 (m, 1H), 7.15 (dd, J = 1.32, 7.57 Hz, 1H), 7.12-7.08 (m, 2H), 4.20 (s, 2H), 3.26 (d, J = 6.90 Hz, 2H), 1.35 (s, 9H) 1.18-1.08 (m, 1H), 0.42-0.37 (m, 2H), 0.26-0.22 (m, 2H); MS (ES) m/z 663.0 [M + H]$^+$; LCMS RT = 0.890 min. | ++ |
| 193 | 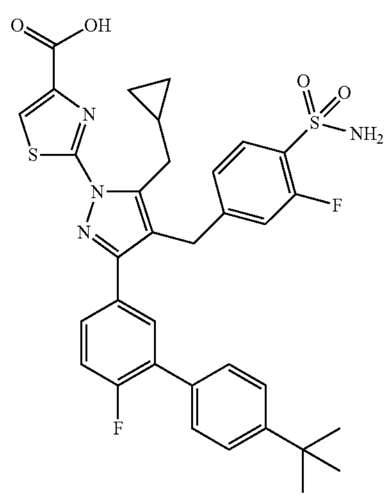 [SMILES: CC(C)(C)c1ccc(-c2cc(-c3nn(-c4nc(C(=O)O)cs4)c(CC4CC4)c3Cc3ccc(S(N)(=O)=O)c(F)c3)ccc2F)cc1] | 2-(3-(4'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (MeOD) δ 8.20 (s, 1H), 7.79 (t, J = 7.88 Hz, 1H), 7.63-7.59 (m, 1H), 7.53 (dd, J = 2.22, 7.50 Hz, 1H), 7.49-7.48 (m, 2H), 7.30 (dd, J = 1.58, 8.43 Hz, 2H), 7.23-7.18 (m, 1H), 7.12 (s, 1H), 7.10 (d, 2.11 Hz, 1H), 4.19 (s, 2H), 3.29 (d, 6.41 Hz, 2H), 1.38 (s, 9H), 1.19-1.11 (m, 1H), 0.44-0.40 (m, 2H), 0.29-0.25 (m, 2H); MS (ES) m/z 663.0 [M + H]$^+$; LCMS M/Z = 1.406 min. | ++ |

TABLE 7-continued

| Cmpd ID | Structure | Compound name and physical data | Inhibitory activity IC$_{50}$ (μM) |
|---|---|---|---|
| 194 | 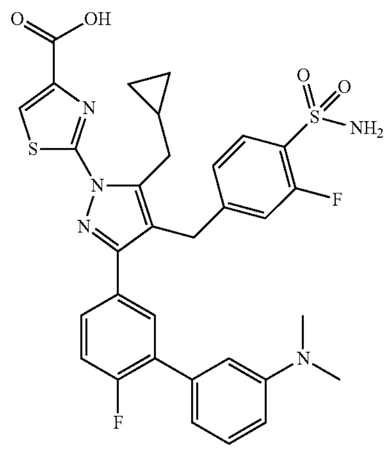 [SMILES: CN(C)c1cccc(-c2cc(-c3nn(-c4nc(C(=O)O)cs4)c(CC4CC4)c3Cc3ccc(S(N)(=O)=O)c(F)c3)ccc2F)c1] | 2-(5-(cyclopropylmethyl)-3-(3'-(dimethylamino)-6-fluoro-[1,1'-biphenyl]-3-yl)-4-(3-fluoro-4-sulfamoylbenzyl)-1H-pyrazol-1-yl)thiazole-4-carboxylic acid: $^1$H NMR (DMSO) δ: 8.30 (s, 1H), 7.68-7.58 (m, 5H), 7.35 (t, J = 8.6 Hz, 1H), 7.29 (t, J = 7.7 Hz, 1H), 7.18 (d, J = 11.3 Hz, 1H), 7.07 (d, J = 8.0 Hz, 1H), 6.84 (s, 2H), 6.71 (s, J = 7.3 Hz, 1H), 4.18 (s, 2H), 3.15 (s, 2H), 2.92 (2, 6H), 1.14-1.13 (m, 1H), 0.34-0.32 (m, 2H), 0.22-0.21 (m, 2H). MS (ES) m/z 650.0 [M + H]$^+$; LCMS RT = 1.022 min. | +++ |
| 195 | 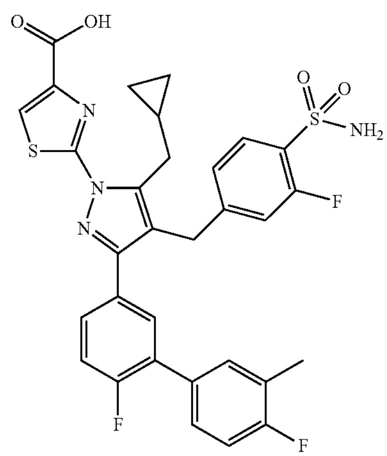 [SMILES: Cc1cc(-c2cc(-c3nn(-c4nc(C(=O)O)cs4)c(CC4CC4)c3Cc3ccc(S(N)(=O)=O)c(F)c3)ccc2F)ccc1F] | 2-(5-(cyclopropylmethyl)-3-(4',6-difluoro-3'-methyl-[1,1'-biphenyl]-3-yl)-4-(3-fluoro-4-sulfamoylbenzyl)-1H-pyrazol-1-yl)thiazole-4-carboxylic acid: $^1$H NMR (DMSO) δ: 8.31 (s, 1H), 7.69-7.60 (m, 4H), 7.51 (dd, J = 2.0, 7.5 Hz, 1H), 7.39-7.35 (m, 2H), 7.22-7.18 (m, 3H), 7.07 (d, J = 7.8 Hz, 2H), 4.18 (s, 2H), 3.18 (s, 3H), 2.28 (s, 3H), 0.16-0.12 (m, 1H), 0.37-0.32 (m, 2H), 0.23-0.22 (m, 2H). MS (ES) m/z 639.0 [M + H]$^+$; LCMS RT = 1.292 min. | +++ |
| 196 | 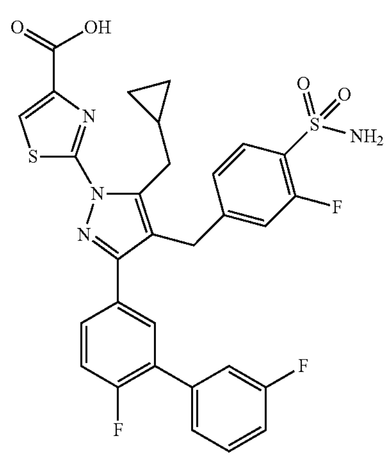 [SMILES: NS(=O)(=O)c1ccc(Cc2c(-c3ccc(F)c(-c4cccc(F)c4)c3)nn(-c3nc(C(=O)O)cs3)c2CC2CC2)cc1F] | 2-(5-(cyclopropylmethyl)-3-(3',6-difluoro-[1,1'-biphenyl]-3-yl)-4-(3-fluoro-4-sulfamoylbenzyl)-1H-pyrazol-1-yl)thiazole-4-carboxylic acid: $^1$H NMR (CDCl$_3$) δ 8.14 (s, 1H), 7.87 (d, J = 8 Hz, 2H), 7.51-7.55 (m, 1H), 7.47-7.49 (m, 1H), 7.36-7.42 (m, 1H), 7.28 (d, J = 8 Hz, 2H), 7.16-7.21 (m, 2H), 7.04-7.09 (m, 2H), 4.92 (s, 2H), 4.18 (s, 2H), 2.21-2.28 (m, 1H), 1.10-1.12 (m, 2H), 0.72-0.73 (m, 2H); MS (ES) 593 [M + H]$^+$; LCMS RT = 1.27 min. | +++ |

TABLE 7-continued

| Cmpd ID | Structure | Compound name and physical data | Inhibitory activity IC$_{50}$ (μM) |
|---|---|---|---|
| 197 | 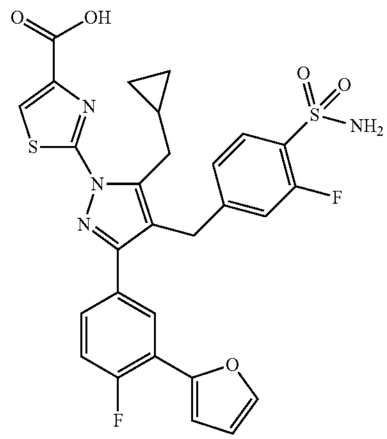 [SMILES: NS(=O)(=O)c1ccc(Cc2c(-c3ccc(F)c(-c4ccco4)c3)nn(-c3nc(C(=O)O)cs3)c2CC2CC2)cc1F] | 2-(5-(cyclopropylmethyl)-3-(3-(4,5-dihydrofuran-2-yl)-4-fluorophenyl)-4-(3-fluoro-4-sulfamoylbenzyl)-1H-pyrazol-1-yl)thiazole-4-carboxylic acid - MS (ES) m/z 599.0 [M + H]$^+$; LCMS RT = 1.06 min. | +++ |
| 198 | 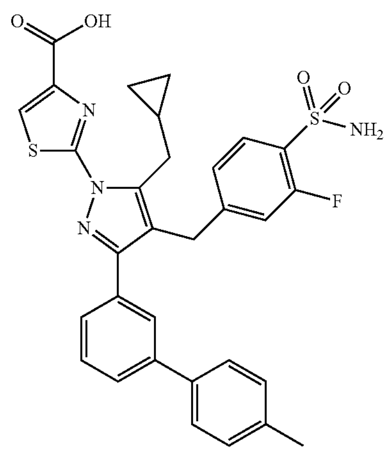 [SMILES: Cc1ccc(-c2cccc(-c3nn(-c4nc(C(=O)O)cs4)c(CC4CC4)c3Cc3ccc(S(N)(=O)=O)c(F)c3)c2)cc1] | 2-(5-(cyclopropylmethyl)-4-(3-fluoro-4-sulfamoylbenzyl)-3-(4'-methyl-[1,1'-biphenyl]-3-yl)-1H-pyrazol-1-yl)thiazole-4-carboxylic acid: $^1$H NMR (CDCl$_3$) δ: 8.13 (s, 1H), 7.82 (t, J = 7.6 Hz, 1H), 7.64 (s, 1H), 7.61 (dt, J = 2.0, 6.8 Hz, 1H), 7.49-7.44 (m, 2H), 7.38 (d, J = 8.4 Hz, 2H), 7.26 (d, J = 8.0 Hz, 2H), 7.10 (d, J = 8.4 Hz, 1H), 7.01 (d, J = 10.8 Hz, 1H), 4.12 (s, 2H), 3.20 (d, J = 6.6 Hz, 2H), 2.42 (s, 3H), 1.22-1.18 (m, 1H), 0.53-0.49 (m, 2H), 0.27-0.24 (m, 2H); MS (ES) m/z 603.0 [M + H]$^+$; LCMS RT = 1.298 min. | +++ |
| 199 | 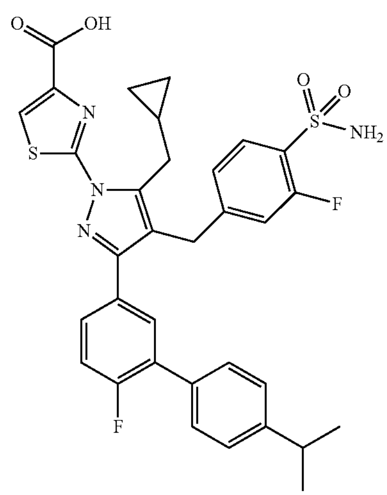 [SMILES: CC(C)c1ccc(-c2cc(-c3nn(-c4nc(C(=O)O)cs4)c(CC4CC4)c3Cc3ccc(S(N)(=O)=O)c(F)c3)ccc2F)cc1] | 2-(5-(cyclopropylmethyl)-3-(6-fluoro-3'-isopropyl-[1,1'-biphenyl]-3-yl)-4-(3-fluoro-4-sulfamoylbenzyl)-1H-pyrazol-1-yl)thiazole-4-carboxylic acid: MS (ES) m/z 648.0 [M + H]$^+$; LCMS RT = 1.358 min. | +++ |

TABLE 7-continued

| Cmpd ID | Structure | Compound name and physical data | Inhibitory activity IC$_{50}$ (μM) |
|---|---|---|---|
| 200 | 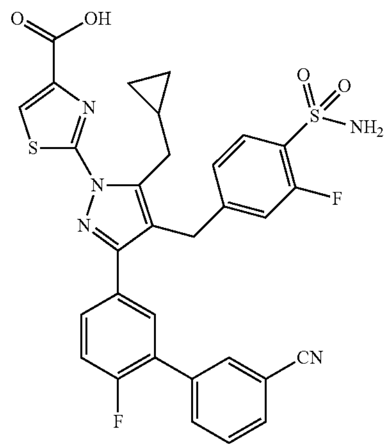 [SMILES: N#Cc1cccc(-c2cc(-c3nn(-c4nc(C(=O)O)cs4)c(CC4CC4)c3Cc3ccc(S(N)(=O)=O)c(F)c3)ccc2F)c1] | 2-(3-(3'-cyano-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid - $^1$H NMR (d$^6$-DMSO) δ: 8.31 (s, 1H), 8.03 (s, 1H), 7.89 (d, J = 7.4 Hz, 1H), 7.73-7.63 (m, 5H), 7.57 (s, 2H), 7.42 (d, J = 10.3 Hz, 1H), 7.16 (d, J = 11.2 Hz, 1H), 7.07 (d, J = 8.1 Hz, 1H), 4.21 (s, 2H), 3.18 (d, J = 6.8 Hz, 2H), 1.50 (bs, 1H), 0.36-0.34 (m, 2H), 0.24-0.23 (m, 2H); MS (ES) m/z 632.0 [M + H]$^+$; LCMS RT = 1.197 min. | +++ |
| 201 | 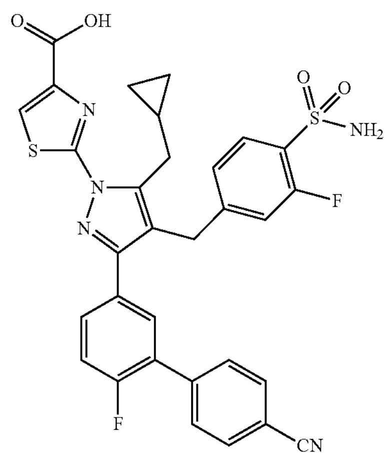 [SMILES: N#Cc1ccc(-c2cc(-c3nn(-c4nc(C(=O)O)cs4)c(CC4CC4)c3Cc3ccc(S(N)(=O)=O)c(F)c3)ccc2F)cc1] | 2-(3-(4'-cyano-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (400 MHz, CDCl3): δ 8.14 (s, 1H), 7.84 (t, J = 8 Hz, 1H), 7.75 (d, J = 8 Hz, 2H), 7.56-7.60 (m, 3H), 7.50-7.54 (m, 1H), 7.21 (t, J = 16 Hz, 1H), 7.08 (d, J = 8 Hz, 1H), 7.01 (d, J = 8 Hz, 1H), 5.12 (s, 2H), 4.11 (s, 2H), 3.20 (d, J = 8 Hz, 2H), 1.15-1.18 (m, 1H), 0.47-0.50 (m, 2H), 0.24-0.27 (m, 2H); MS (ES) m/z 632.0 [M + H]$^+$; LCMS RT = 1.22 min. | +++ |
| 202 | 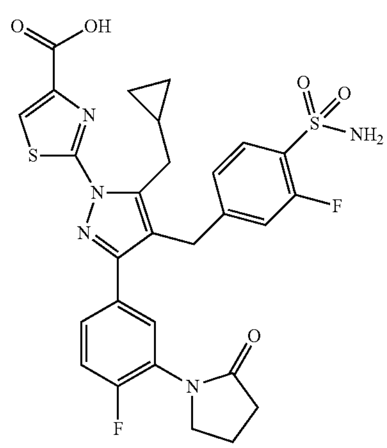 [SMILES: NS(=O)(=O)c1ccc(Cc2c(-c3ccc(F)c(N4CCCC4=O)c3)nn(-c3nc(C(=O)O)cs3)c2CC2CC2)cc1F] | 2-(5-(cyclopropylmethyl)-3-(4-fluoro-3-(2-oxopyrrolidin-1-yl)phenyl)-4-(3-fluoro-4-sulfamoylbenzyl)-1H-pyrazol-1-yl)thiazole-4-carboxylic acid: MS (ES) m/z 614.0 [M + H]$^+$; LCMS RT = 1.005 min. | +++ |

TABLE 7-continued

| Cmpd ID | Structure | Compound name and physical data | Inhibitory activity IC$_{50}$ (μM) |
|---|---|---|---|
| 203 | 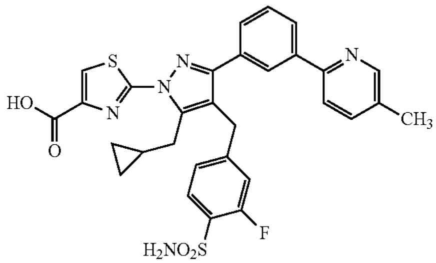 [SMILES: Cc1ccc(-c2cccc(-c3nn(-c4nc(C(=O)O)cs4)c(CC4CC4)c3Cc3ccc(S(N)(=O)=O)c(F)c3)c2)nc1] | 2-(5-(cyclopropylmethyl)-4-(3-fluoro-4-sulfamoylbenzyl)-3-(3-(5-methylpyridin-2-yl)phenyl)-1H-pyrazol-1-yl)thiazole-4-carboxylic acid: MS [M + H]$^+$ 604.0. | +++ |
| 204 | 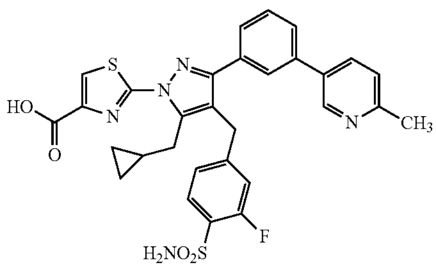 [SMILES: Cc1ccc(-c2cccc(-c3nn(-c4nc(C(=O)O)cs4)c(CC4CC4)c3Cc3ccc(S(N)(=O)=O)c(F)c3)c2)cn1] | 2-(5-(cyclopropylmethyl)-4-(3-fluoro-4-sulfamoylbenzyl)-3-(3-(6-methylpyridin-3-yl)phenyl)-1H-pyrazol-1-yl)thiazole-4-carboxylic acid: MS [M + H]$^+$ 604.0. | +++ |
| 205 | 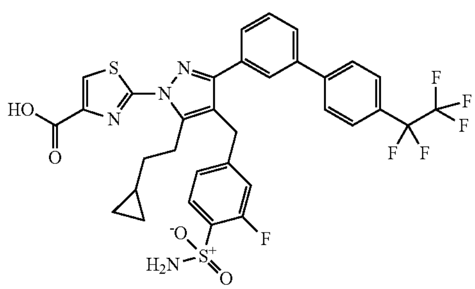 | 2-(5-(2-cyclopropylethyl)-4-(3-fluoro-4-sulfamoylbenzyl)-3-(4'-(perfluoroethyl)-[1,1'-biphenyl]-3-yl)-1H-pyrazol-1-yl)thiazole-4-carboxylic acid: $^1$H NMR (400 MHz, MeOD) δ 8.06 (s, 1H), 7.67-7.52 (m, 8H), 7.40 (dd, J = 7.3, 7.7 Hz, 1H), 6.99 (s, 1H), 6.97 (d, J = 3.82 Hz, 1H), 4.09 (s, 2H), 3.25 (dd, J = 7.5, 9.6 Hz, 2H), 1.44-1.39 (m, 2H), 0.68-0.60 (m, 1H), 0.27-0.22 (m, 2H), 0.01--0.02 (m, 2H); MS ([M + H]$^+$ 721.0. | ++ |
| 206 | 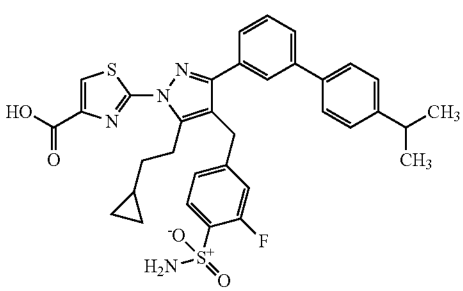 | 2-(5-(2-cyclopropylethyl)-4-(3-fluoro-4-sulfamoylbenzyl)-3-(4'-isopropyl-[1,1'-biphenyl]-3-yl)-1H-pyrazol-1-yl)thiazole-4-carboxylic acid: $^1$H NMR (400 MHz, MeOD) δ 8.03 (s, 1H), 7.66 (t, J = 7.6 Hz, 1H), 7.53 (s, 1H), 7.47 (d, J = 7.92 Hz, 1H), 7.42 (d, J = 7.92 Hz, 1H), 7.30 (t, J = 7.66 Hz, 1H), 7.23 (d, J = 8.2 Hz, 2H), 7.16 (d, J = 8.2 Hz, 2H), 6.96 (d, J = 9.5 Hz, 2H), 4.02 (s, 2H), 3.23-3.19 (m, 2H), 2.81 (septet, J = 6.87 Hz, 1H), 1.42-1.36 (m, 2H), 1.16 (d, J = 6.9 Hz, 6H), 0.67-0.59 (m, 1H), 0.26-0.22 (m, 2H), 0.01--0.02 (m, 2H); [M + H]$^+$ 645.0. | ++ |
| 207 | 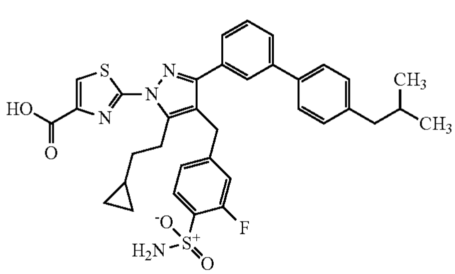 | 2-(5-(2-cyclopropylethyl)-4-(3-fluoro-4-sulfamoylbenzyl)-3-(4'-isobutyl-[1,1'-biphenyl]-3-yl)-1H-pyrazol-1-yl)thiazole-4-carboxylic acid: $^1$H NMR (400 MHz, MeOD) δ 8.04 (s, 1H), 7.66 (t, J = 8.03 Hz, 1H), 7.55 (s, 1H), 7.48 (d, J = 7.7 Hz, 1H), 7.42 (d, J = 7.7 Hz, 1H), 7.31 (t, J = 7.7 Hz, 1H), 7.23 (d, J = 8.2 Hz, 2H), 7.08 (d, J = 8.2 Hz, 1H), 6.98 (s, 1H), 6.96 (d, J = 2.4 Hz, 1H), 4.04 (s, 2H), 3.25-3.20 (m, 2H), 2.39 (d, J = 7.0 Hz, 2H), 1.78 (septet, J = 6.7 Hz, 1H), 1.43-1.37 (m, 2H), 0.81 (d, J = 6.7 Hz, 6H), 0.67-0.58 (m, 1H), 0.27-0.22 (m, 2H), 0.01-0.02 (m, 2H)); MS [M + H]$^+$ 659.0. | ++ |

TABLE 7-continued

| Cmpd ID | Structure | Compound name and physical data | Inhibitory activity IC$_{50}$ (μM) |
|---|---|---|---|
| 208 | 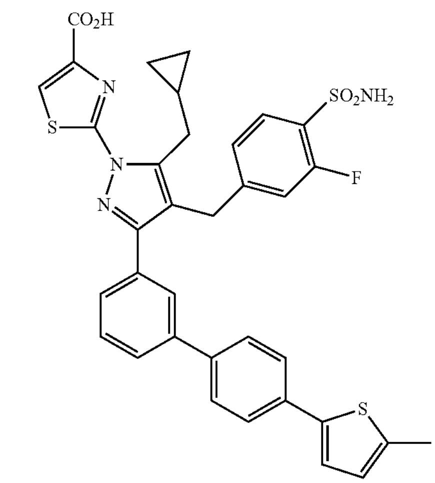 [SMILES: Cc1ccc(-c2ccc(-c3cccc(-c4nn(-c5nc(C(=O)O)cs5)c(CC5CC5)c4Cc4ccc(S(N)(=O)=O)c(F)c4)c3)cc2)s1] | 2-(5-(cyclopropylmethyl)-4-(3-fluoro-4-sulfamoylbenzyl)-3-(4'-(5-methylthiophen-2-yl)-[1,1'-biphenyl]-3-yl)-1H-pyrazol-1-yl)thiazole-4-carboxylic acid: $^1$H NMR (400 MHz, MeOD) δ 8.15 (s, 1H), 7.77 (t, J = 8.0 Hz, 1H), 7.70-7.67 (m, 1H), 7.62-7.53 (m, 1H), 7.58 (d, J = 8.4 Hz, 2H), 7.54 (d, J = 7.6 Hz, 1H), 7.43 (d, J = 7.6 Hz, 1H), 7.39 (d, J = 8.4 Hz, 2H), 7.18 (d, J = 3.6 Hz, 1H), 7.08 (dd, J = 10.4, 8.4 Hz, 2H), 6.74 (dd, J = 3.6, 1.2 Hz, 1H), 4.14 (s, 2H), 3.25 (d, J = 6.4 Hz, 2H), 2.49 (s, 3H), 1.14-1.09 (m, 1H), 0.44-0.38 (m, 2H), 0.27-0.22 (m, 2H); MS [M + H]$^+$ 685.3. | ++ |
| 209 | 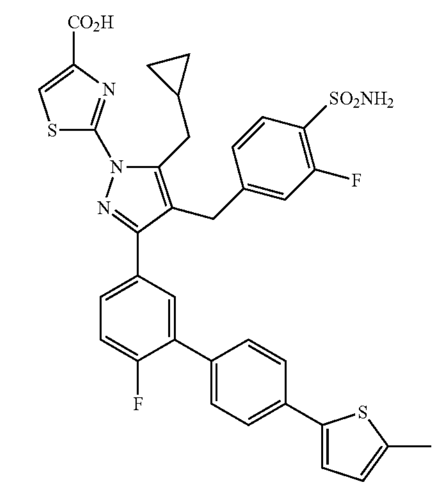 [SMILES: Cc1ccc(-c2ccc(-c3cc(-c4nn(-c5nc(C(=O)O)cs5)c(CC5CC5)c4Cc4ccc(S(N)(=O)=O)c(F)c4)ccc3F)cc2)s1] | 2-(5-(cyclopropylmethyl)-3-(6-fluoro-4'-(5-methylthiophen-2-yl)-[1,1'-biphenyl]-3-yl)-4-(3-fluoro-4-sulfamoylbenzyl)-1H-pyrazol-1-yl)thiazole-4-carboxylic acid: $^1$H NMR (400 MHz, MeOD) δ 8.17 (s, 1H), 7.79 (t, J = 8.0 Hz, 1H), 7.62 (d, J = 8.4 Hz, 2H), 7.59 (dd, J = 8.0, 6.0 Hz, 2H), 7.38 (dd, J = 8.4, 1.6 Hz, 2H), 7.24 (d, J = 3.6 Hz, 1H), 7.19 (d, J = 8.8 Hz, 1H), 7.12-7.07 (m, 2H), 6.77 (dd, J = 3.6, 1.2 Hz, 1H), 4.18 (s, 2H), 3.28 (d, J = 6.8 Hz, 2H), 2.52 (s, 3H), 1.16-1.09 (m, 1H), 0.44-0.39 (m, 2H), 0.28-0.23 (m, 2H); MS [M + H]$^+$ 703.1. | ++ |
| 210 | 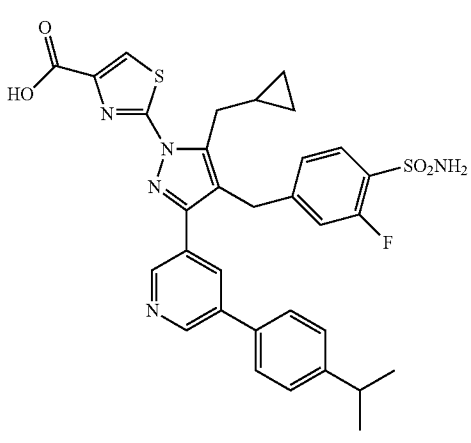 [SMILES: CC(C)c1ccc(-c2cncc(-c3nn(-c4nc(C(=O)O)cs4)c(CC4CC4)c3Cc3ccc(S(N)(=O)=O)c(F)c3)c2)cc1] | 2-[5-(cyclopropylmethyl)-4-[(3-fluoro-4-sulfamoylphenyl)methyl]-3-[5-(4-isopropylphenyl)pyridin-3-yl]pyrazol-1-yl]-1,3-thiazole-4-carboxylic acid, $^1$H NMR (400 MHz, MeOD-d$_3$) δ 8.85 (d, J = 21.0 Hz, 2H), 8.34 (bs, 1H), 8.25 (s, 1H), 7.78 (t, J = 7.8 Hz, 1H), 7.46 (d, J = 8.0 Hz, 2H), 7.04 (d, J = 7.6 Hz, 2H), 7.17-7.13 (m, 2H), 4.28 (2, 2H), 3.01-2.94 (m, 1H), 0.86 (s, 2H), 1.29 (d, J = 6.9 Hz, 2H), 1.20-1.14 (m, 1H), 0.44-0.41 (m, 2H), 0.30-0.28 (m, 2H). | +++ |

TABLE 7-continued

| Cmpd ID | Structure | Compound name and physical data | Inhibitory activity IC$_{50}$ (μM) |
|---|---|---|---|
| 211 | 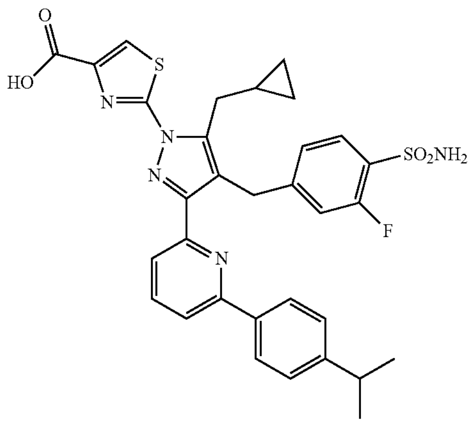 | 2-[5-(cyclopropylmethyl)-4-[(3-fluoro-4-sulfamoylphenyl)methyl]-3-[6-(4-isopropylphenyl)pyridin-2-yl]pyrazol-1-yl]-1,3-thiazole-4-carboxylic acid, $^1$H NMR (400 MHz, MeOD-d$_3$) δ 8.20 (s, 1H), 8.03 (d, J = 7.8 Hz, 1H), 7.87 (t, J = 8.1 Hz, 1H), 7.76 (d, J = 7.8 Hz, 1H), 7.70 (t, J = 8.0 Hz, 1H), 7.62 (d, J = 8.3 Hz, 2H), 7.22 (d, J = 14.1 Hz, 2H), 7.14-7.10 (M, 2H), 4.59 (s, 2H), 3.27 (d, J = 6.9 Hz, 2H), 2.92 (t, J = 6.8 Hz, 1H), 1.27 (d, J = 6.9 Hz, 2H), 1.11-1.07 (m, 1H), .037-.032 (m, 2H), 0.23-0.19 (m, 2H); MS [M + H]$^+$ = 660.0 | ++ |
| 212 | 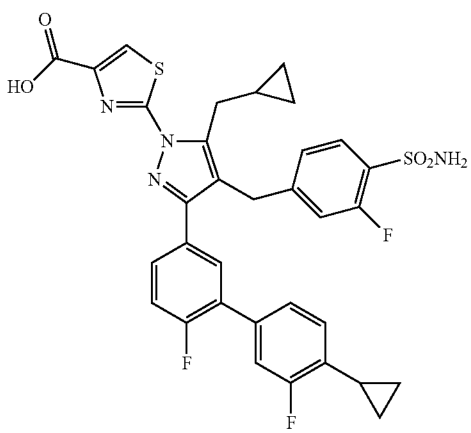 [SMILES: NS(=O)(=O)c1ccc(Cc2c(-c3ccc(F)c(-c4ccc(C5CC5)c(F)c4)c3)nn(-c3nc(C(=O)O)cs3)c2CC2CC2)cc1F] | 2-{3-[3-(4-cyclopropyl-3-fluorophenyl)-4-fluorophenyl]-5-(cyclopropylmethyl)-4-[(3-fluoro-4-sulfamoylphenyl)methyl]pyrazol-1-yl}-1,3-thiazole-4-carboxylic acid, $^1$H NMR (400 MHz, MeOD-d$_3$) δ 8.09 (1H, s), 7.76 (t, 1H, J = 8.0 Hz), 7.62-7.58 (m, 1H), 7.52 (dd, J = 7.5, 2.0 Hz, 1H), 7.22-7.17 (m, 2H), 7.02 (d, J = 12.0 Hz, 1H), 7.04 (d, J = 16.0 Hz, 2H), 7.02-6.95 (m, 2H), 4.17 (s, 2H), 3.28 (d, J = 6.5 Hz, 2H), 2.14-1.99 (m, 1H), 1.31-1.08 (m, 1H), 1.04-0.99 (m, 2H), 0.82-0.77 (m, 2H), 0.41-0.36 (m, 2H), 0.25-.021 (m, 2H); MS [M + H]$^+$ = 665.0 | ++ |
| 213 | 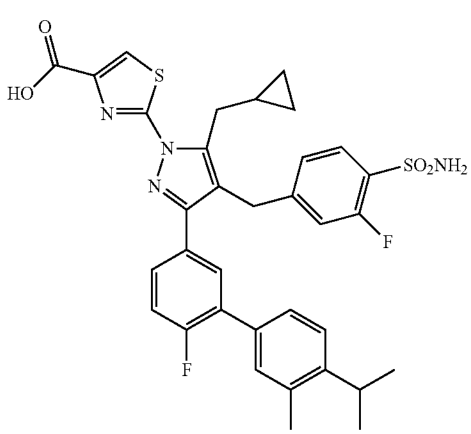 [SMILES: Cc1cc(-c2cc(-c3nn(-c4nc(C(=O)O)cs4)c(CC4CC4)c3Cc3ccc(S(N)(=O)=O)c(F)c3)ccc2F)ccc1C(C)C] | 2-[5-(cyclopropylmethyl)-3-[4-fluoro-3-(4-isopropyl-3-methylphenyl)phenyl]-4-[(3-fluoro-4-sulfamoylphenyl)methyl]pyrazol-1-yl]-1,3-thiazole-4-carboxylic acid, $^1$H NMR (400 MHz, MeOD-d$_3$) δ 8.17 (s, 1H), 7.73 (t, J = 7.8 Hz, 1H), 7.59-7.54 (m, 2H), 7.43-7.34 (m, 1H), 7.12-7.01 (m, 4H), 4.86 (s, 6H), 4.13 (s, 2H), 3.23 (d, J = 6.8 Hz, 2H), 2.01 (s, 2H), 1.20 (s, 3H), 1.13-1.06 (m, 1H), 0.39-0.35 (m, 2H), 0.28-0.21 (m, 2H). | +++ |

TABLE 7-continued

| Cmpd ID | Structure | Compound name and physical data | Inhibitory activity IC$_{50}$ (μM) |
|---|---|---|---|
| 214 | 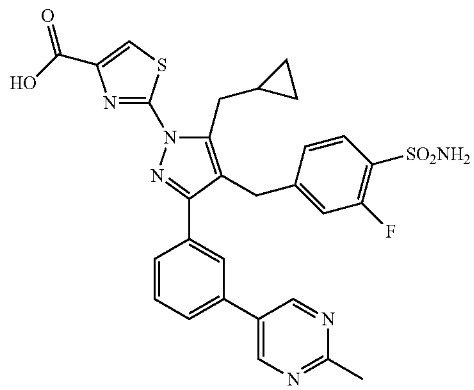 [SMILES: Cc1ncc(-c2cccc(-c3nn(-c4nc(C(=O)O)cs4)c(CC4CC4)c3Cc3ccc(S(N)(=O)=O)c(F)c3)c2)cn1] | 2-[5-(cyclopropylmethyl)-4-[(3-fluoro-4-sulfamoylphenyl)methyl]-3-[3-(2-methylpyrimidin-5-yl)phenyl]pyrazol-1-yl]-1,3-thiazole-4-carboxylic acid, $^1$H NMR (400 MHz, DMSO-d$_6$) δ 8.95 (s, 2H), 8.27 (s, 1H), 7.87 (s, 1H), 7.78 (d, J = 7.9 Hz, 1H), 7.65-7.61 (m, 2H), 7.58-7.54 (m, 2H), 7.14 (d, J = 11.6 Hz, 1H), 7.07 (d, J = 8.2 Hz, 1H), 4.22 (s, 2H), 3.19 (d, J = 6.7 Hz, 2H), 2.67 (s, 3H), 1.15 (bs, 1H), 0.38-0.33 (m, 2H), 0.24-0.23 (m, 2H); MS [M + H]$^+$ = 605.0 | +++ |
| 215 | 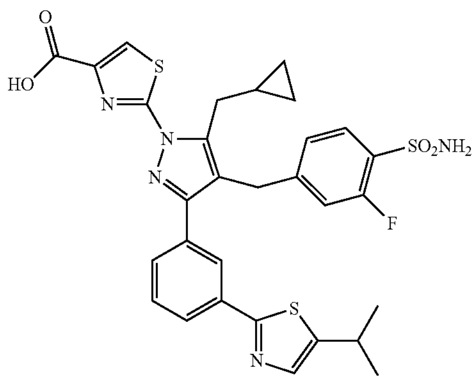 [SMILES: CC(C)c1cnc(-c2cccc(-c3nn(-c4nc(C(=O)O)cs4)c(CC4CC4)c3Cc3ccc(S(N)(=O)=O)c(F)c3)c2)s1] | 2-[5-(cyclopropylmethyl)-4-[(3-fluoro-4-sulfamoylphenyl)methyl]-3-[3-(5-isopropyl-1,3-thiazol-2-yl)phenyl]pyrazol-1-yl]-1,3-thiazole-4-carboxylic acid, $^1$H NMR (400 MHz, DMSO-d$_6$) δ 8.32 (s, 1H), 7.94 (s, 1H), 7.90 (d, J = 8.3 Hz, 1H), 7.69-7.66 (m, 2H), 7.65 (s, 1H), 7.57 (s, 1H), 7.53 (t, J = 11.4 Hz, 1H), 7.23 (d, J = 11.7 Hz, 1H), 7.09 (d, J = 7.8 Hz, 1H), 4.19 (s, 2H), 3.28-3.24 (m, 1H), 3.20 (d, J = 7.2 Hz, 2H), 1.32 (d, J = 6.8 Hz, 6H), 1.63-1.46 (m, 1H), 0.36-0.34 (m, 2H), 0.25-0.24 (m, 2H); MS [M + H]$^+$ = 638.0 | +++ |
| 216 | 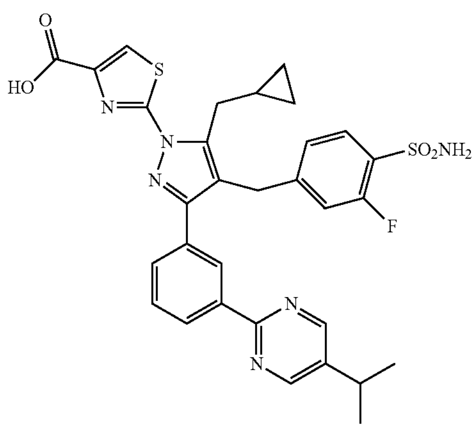 | 2-[5-(cyclopropylmethyl)-4-[(3-fluoro-4-sulfamoylphenyl)methyl]-3-[3-(5-isopropylpyrimidin-2-yl)phenyl]pyrazol-1-yl]-1,3-thiazole-4-carboxylic acid, $^1$H NMR (400 MHz, DMSO-d$_6$) δ 8.80 (s, 2H), 8.50 (s, 1H), 8.36 (d, J = 7.8 Hz, 1H), 8.30 (2, 1H), 7.73-7.65 (m, 2H), 7.60-7.54 (m, 4H), 7.21 (d, J = 10.8 Hz, 1H), 7.09 (d, J = 7.9 Hz, 1H), 4.18 (s, 2H), 3.21 (d, J = 7.0 Hz, 2H), 2.99 (m, 1H), 1.29 (d, J = 7.0 Hz, 6H), 1.18-1.41 (m 1H), 0.39-0.35 (m, 2H), 0.26-0.24 (m, 2H); MS [M + H]$^+$ = 661.0 | +++ |
| 217 | 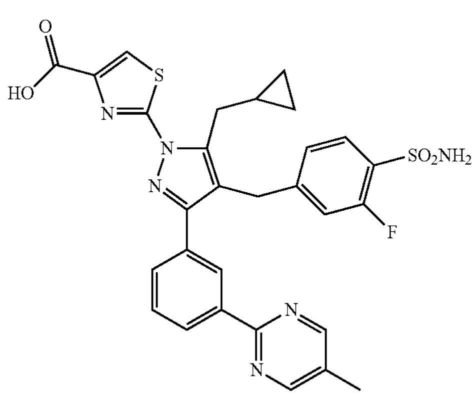 [SMILES: Cc1cnc(-c2cccc(-c3nn(-c4nc(C(=O)O)cs4)c(CC4CC4)c3Cc3ccc(S(N)(=O)=O)c(F)c3)c2)nc1] | 2-[5-(cyclopropylmethyl)-4-[(3-fluoro-4-sulfamoylphenyl)methyl]-3-[3-(5-methylpyrimidin-2-yl)phenyl]pyrazol-1-yl]-1,3-thiazole-4-carboxylic acid, $^1$H NMR (400 MHz, CDCl3-d$_3$) δ 8.62 (s, 2H), 8..40 (s, 1H), 8.33 (d, J = 8.3 Hz, 1H), 8.01 (s, 1H), 7.71-7.67 (m, 2H), 7.48 (t, J = 7.8 Hz, 1H), 7.05 (d, J = 8.5 Hz, 1H), 6.99 (d, J = 3.1 Hz, 1H), 4.11 (s, 2H), 3.41 (t, J = 1.6 Hz, 1H), 3.46 (d, J = 6.6 Hz, 2H), 2.35 (s, 3H), 1.24-1.14 (m, 1H), 0.45-0.42 (m, 2H), 0.26-0.24 (m, 2H); MS [M + H]$^+$ = 605.0c | +++ |

TABLE 7-continued

| Cmpd ID | Structure | Compound name and physical data | Inhibitory activity IC$_{50}$ (μM) |
|---|---|---|---|
| 218 | 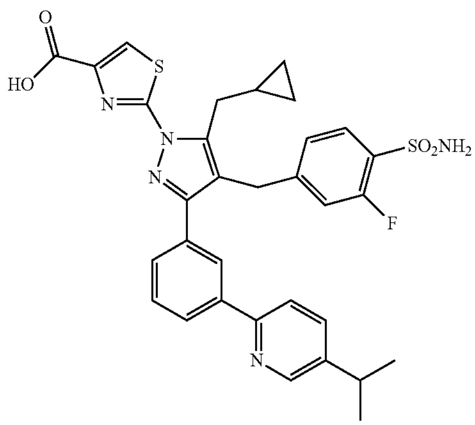 | 2-[5-(cyclopropylmethyl)-4-[(3-fluoro-4-sulfamoylphenyl)methyl]-3-[3-(5-isopropylpyridin-2-yl)phenyl]pyrazol-1-yl]-1,3-thiazole-4-carboxylic acid, $^1$H NMR (400 MHz, MeOD-d$_3$) δ 8.58 (d, J = 1.9 Hz, 1H), 8.25 (dd, J = 4.5, 8.4 Hz, 1H), 8.21 (s, 1H), 7.92 (bs, 1H), 7.89 (d, J = 7.8 Hz, 1H), 7.80 (t, J = 8.6 Hz, 2H), 7.72 (t, J = 8.1 Hz, 1H), 7.60 (t, J = 7.8 Hz, 1H), 710-7.07 (m, 2H), 4.20 (s, 2H), 3.19-3.12 (m, 1H), 1.38 (d, J = 7.0 Hz, 6H), 1.18-1.14 (m, 1H), 0.42-0.40 (m, 2H), 0.29-0.25 (m, 2H); MS [M + H]$^+$ = 660.0 | +++ |
| 219 | 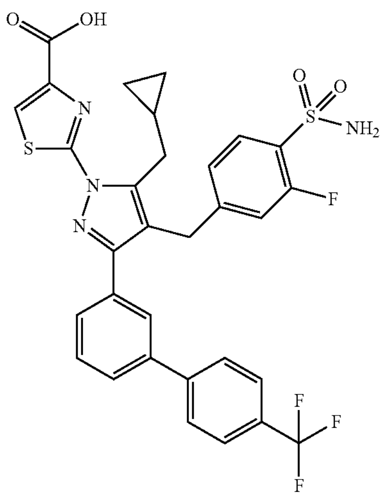 [SMILES: NS(=O)(=O)c1ccc(Cc2c(-c3cccc(-c4ccc(C(F)(F)F)cc4)c3)nn(-c3nc(C(=O)O)cs3)c2CC2CC2)cc1F] | 2-(5-(cyclopropylmethyl)-4-(3-fluoro-4-sulfamoylbenzyl)-3-(4'-(trifluoromethyl)-[1,1'-biphenyl]-3-yl)-1H-pyrazol-1-yl)thiazole-4-carboxylic acid, $^1$H NMR (400 MHz, MeOD-d$_3$) δ 8.20 (s, 1H), 7.79-7.76 (s, 1 H), 7.75-7.70 (m, 2H), 7.69-7.65 (m, 2H), 7.64-7.60 (m, 3H), 7.49 (t, J = 7.8 Hz, 1 H), 7.12-7.07 (m, 2H), 4.19 (s, 2H), 3.27 (d, J = 6.9 Hz, 2H), 1.20-1.09 (m, 1H), 0.43-0.37 (m, 2H), 0.28-0.23 (m, 2H); MS (ES) 657.0 [M + H]$^+$, LCMS RT = 1.273 min. | +++ |
| 220 | 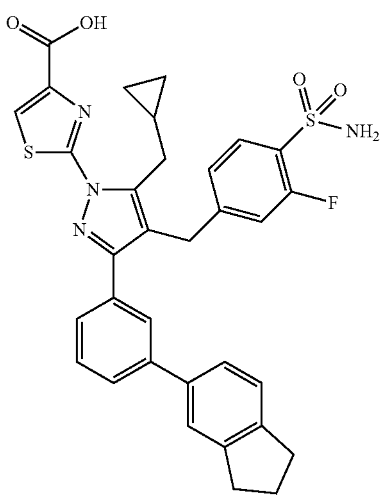 [SMILES: NS(=O)(=O)c1ccc(Cc2c(-c3cccc(-c4ccc5c(c4)CCC5)c3)nn(-c3nc(C(=O)O)cs3)c2CC2CC2)cc1F] | 2-(5-(cyclopropylmethyl)-3-(3-(2,3-dihydro-1H-inden-5-yl)phenyl)-4-(3-fluoro-4-sulfamoylbenzyl)-1H-pyrazol-1-yl)thiazole-4-carboxylic acid, $^1$H NMR (400 MHz, MeOD-d$_3$) δ 8.19 (s, 1H), 7.79-7.74 (M, 1H), 7.64-7.63 (m, 1H), 7.60-7.54 (m, 2H), 7.42 (t, J = 7.7 Hz, 1H), 7.29 (s, 1H), 7.23 (d, J = 7.7 Hz, 1H), 7.19-7.15 (m, 1H), 7.12-7.08 (m, 2H), 4.19 (s, 2H), 3.26 (d, J = 6.7 Hz, 2H), 2.96-2.89 (m, 4H), 2.09 (quintet, J = 7.4 Hz, 2H), 1.17-1.08 (m, 1H), 0.42-0.37 (m, 2H), 0.26-0.22 (m, 2H); MS (ES) 629.0 [M + H]$^+$, LCMS RT = 1.316 min. | +++ |

TABLE 7-continued

| Cmpd ID | Structure | Compound name and physical data | Inhibitory activity IC$_{50}$ (μM) |
|---|---|---|---|
| 221 | 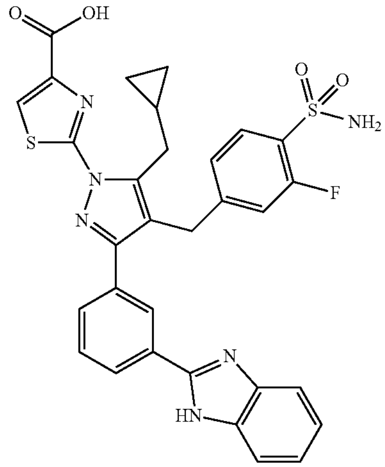 [SMILES: NS(=O)(=O)c1ccc(Cc2c(-c3cccc(-c4nc5ccccc5[nH]4)c3)nn(-c3nc(C(=O)O)cs3)c2CC2CC2)cc1F] | 2-(3-(3-(1H-benzo[d]imidazol-2-yl)phenyl)-5-(cyclopropylmethyl)-4-(3-fluoro-4-sulfamoylbenzyl)-1H-pyrazol-1-yl)thiazole-4-carboxylic acid, $^1$H NMR (400 MHz, MeOD-d$_3$) δ 8.41 (bs, 1H), 8.24 (s, 1 H), 8.11-8.08 (m, 1 H), 7.86-7.83 (m, 1H), 7.79 (q, J = 3.1 Hz, 2 H), 7.72-7.66 (m, 2H), 7.58-7.55 (m, 2H), 7.09-7.02 (m, 2H), 4.27 (s, 2H), 1.21-1.12 (m, 1H), 0.45-0.41 (m, 2H), 0.30-0.26 (m, 2H); MS (ES) 629.0 [M + H]$^+$, LCMS RT = 0.873 min. | +++ |
| 222 | 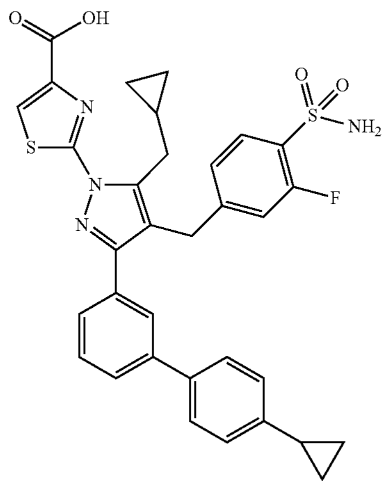 [SMILES: NS(=O)(=O)c1ccc(Cc2c(-c3cccc(-c4ccc(C5CC5)cc4)c3)nn(-c3nc(C(=O)O)cs3)c2CC2CC2)cc1F] | 2-(3-(4'-cyclopropyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid, $^1$H NMR (400 MHz, MeOD-d$_3$) δ 8.19 (s, 1H), 7.79-7.75 (m, 1H), 7.62-7.60 (m, 1H), 7.60-7.53 (m, 2H), 7.42 (t, J = 7.7 Hz, 1H), 7.30-7.26 (m, 2H), 7.13-7.07 (m, 4H), 4.17 (s, 2H), 3.26 (d, J = 6.9 Hz, 2H), 1.96-1.87 (m, 1H), 1.18-1.11 (m, 1H), 1.00-0.95 (m, 2H), 0.74-0.69 (m, 2H), 0.43-0.37 (m, 2H), 0.27-0.22 (m, 2H); MS (ES) 629.0 [M + H]$^+$, LCMS RT = 1.301 min. | ++ |
| 223 | 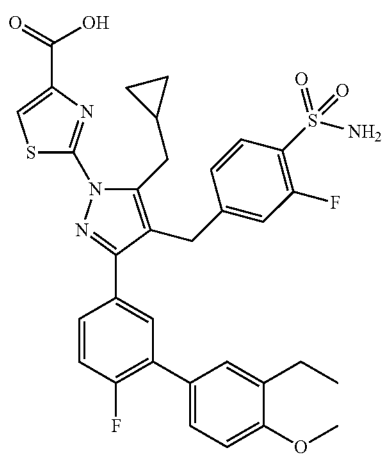 [SMILES: CCc1cc(-c2cc(-c3nn(-c4nc(C(=O)O)cs4)c(CC4CC4)c3Cc3ccc(S(N)(=O)=O)c(F)c3)ccc2F)ccc1OC] | 2-(5-(cyclopropylmethyl)-3-(3'-ethyl-6-fluoro-4'-methoxy-[1,1'-biphenyl]-3-yl)-4-(3-fluoro-4-sulfamoylbenzyl)-1H-pyrazol-1-yl)thiazole-4-carboxylic acid, $^1$H NMR (400 MHz, MeOD-d$_3$) δ 8.19 (s, 1H), 7.79-7.74 (m, 1H), 7.58-7.54 (m, 1H), 7.51-7.48 (m, 1H), 7.24 (s, 1H), 7.17 (dd, J = 8.5, 10.7 Hz, 1H), 7.11 (s, 1H), 7.10-7.05 (m, 2H), 6.96 (d, J = 8.5 Hz, 1H), 4.18 (s, 2H), 3.87 (s, 3H), 3.26 (d, J = 6.8 Hz, 2H), 2.64 (q, J = 7.5 Hz, 2H), 1.18 (t, J = 7.5 Hz, 3H), 1.15-1.10 (m, 1H), 0.42-0.37 (m, 2H), 0.26-0.22 (m, 2H); MS (ES) 665.0 [M + H]$^+$, LCMS RT = 1.307 min. | ++ |

TABLE 7-continued

| Cmpd ID | Structure | Compound name and physical data | Inhibitory activity IC$_{50}$ (μM) |
|---|---|---|---|
| 224 | 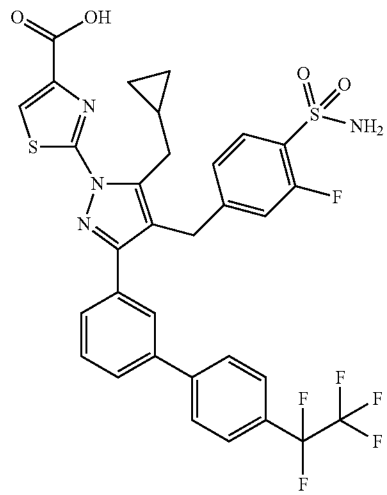 [SMILES: NS(=O)(=O)c1ccc(Cc2c(-c3cccc(-c4ccc(C(F)(F)C(F)(F)F)cc4)c3)nn(-c3nc(C(=O)O)cs3)c2CC2CC2)cc1F] | 2-(5-(cyclopropylmethyl)-4-(3-fluoro-4-sulfamoylbenzyl)-3-(4'-(perfluoroethyl)-[1,1'-biphenyl]-3-yl)-1H-pyrazol-1-yl)thiazole-4-carboxylic acid, $^1$H NMR (400 MHz, MeOD-d$_3$) δ 8.21 (s, 1H), 7.89-7.72 (m, 3H), 7.71 (s, 2H), 7.68 (s, 2H) 7.65 (bs, 1H), 7.51 (t, J = 7.8 Hz, 1H), 7.13-7.08 (m, 2H), 4.21 (s, 2H), 1.19-1.10 (m, 1H), 0.44-0.38 (m, 2H), 0.29-0.24 (m, 2H); MS (ES) 707.0 [M + H]$^+$, LCMS RT = 0.871 min. | ++ |
| 225 | 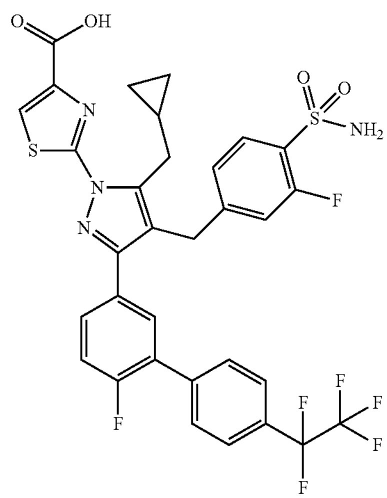 [SMILES: NS(=O)(=O)c1ccc(Cc2c(-c3ccc(F)c(-c4ccc(C(F)(F)C(F)(F)F)cc4)c3)nn(-c3nc(C(=O)O)cs3)c2CC2CC2)cc1F] | 2-(5-(cyclopropylmethyl)-3-(6-fluoro-4'-(perfluoroethyl)-[1,1'-biphenyl]-3-yl)-4-(3-fluoro-4-sulfamoylbenzyl)-1H-pyrazol-1-yl)thiazole-4-carboxylic acid, $^1$H NMR (400 MHz, MeOD-d$_3$) δ 8.20 (s, 1H), 7.77-7.71 (m, 3H), 7.70-7.66 (1H), 7.63-7.58 (m, 3H), 7.26 (dd, J = 8.7, 10.4 Hz, 1H), 7.09 (s, 1H), 7.08-7.06 (m, 1H), 4.19 (s, 2H), 3.28 (d, J = 6.80, 2H), 1.17-1.10 (m, 1H), 0.43-0.37 (m, 2H), 0.28-0.23 (m, 2H); MS (ES) 725.0 [M + H]$^+$, LCMS RT = 0.870 min. | ++ |
| 226 | 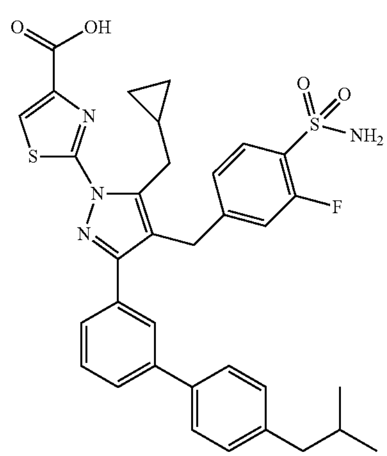 [SMILES: CC(C)Cc1ccc(-c2cccc(-c3nn(-c4nc(C(=O)O)cs4)c(CC4CC4)c3Cc3ccc(S(N)(=O)=O)c(F)c3)c2)cc1] | 2-(5-(cyclopropylmethyl)-4-(3-fluoro-4-sulfamoylbenzyl)-3-(4'-isobutyl-[1,1'-biphenyl]-3-yl)-1H-pyrazol-1-yl)thiazole-4-carboxylic acid, $^1$H NMR (400 MHz, MeOD-d$_3$) δ 8.19 (s, 1H), 7.79-7.74 (m, 1H), 7.67 (s, 1H), 7.58 (dd, J = 7.8, 21.1 Hz, 2H), 7.44 (t, J = 7.8 Hz, 2H), 7.35 (d, J = 8.1 Hz, 2H), 7.21 (d, J = 8.1 Hz, 2H), 7.14-7.08 (m, 2H), 4.20 (s, 2H), 3.28 (d, J = 6.8 Hz, 2H), 2.51 (d, J = 7.1 Hz, 2H), 1.95-1.86 (m, 1H), 1.19-1.10 (m, 1H), 0.93 (d, J = 6.6 Hz, 6H), 0.43-0.39 (m, 2H), 0.28-0.23 (m, 2H); MS (ES) 645.2 [M + H]$^+$, LCMS RT = 0.944 min. | ++ |

TABLE 7-continued

| Cmpd ID | Structure | Compound name and physical data | Inhibitory activity IC$_{50}$ (μM) |
|---|---|---|---|
| 227 | 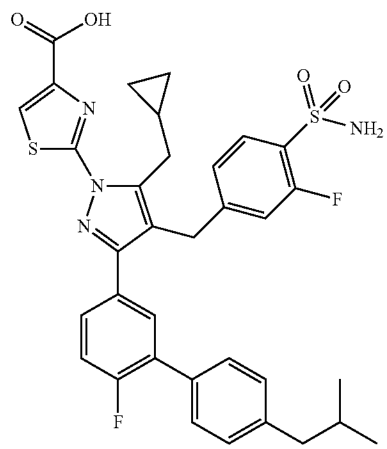 [SMILES: CC(C)Cc1ccc(-c2cc(-c3nn(-c4nc(C(=O)O)cs4)c(CC4CC4)c3Cc3ccc(S(N)(=O)=O)c(F)c3)ccc2F)cc1] | 2-(5-(cyclopropylmethyl)-3-(6-fluoro-4'-isobutyl-[1,1'-biphenyl]-3-yl)-4-(3-fluoro-4-sulfamoylbenzyl)-1H-pyrazol-1-yl)thiazole-4-carboxylic acid); MS (ES) 663.2 [M + H]$^+$, LCMS RT = 0.951 min. | ++ |
| 228 | 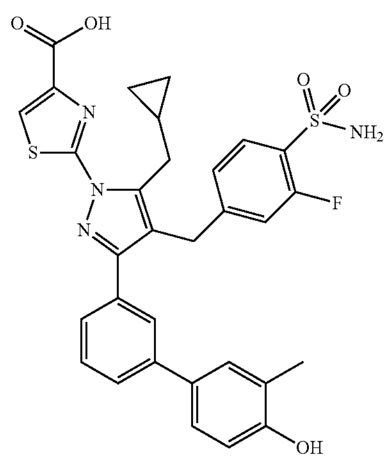 [SMILES: Cc1cc(-c2cccc(-c3nn(-c4nc(C(=O)O)cs4)c(CC4CC4)c3Cc3ccc(S(N)(=O)=O)c(F)c3)c2)ccc1O] | 2-(5-(cyclopropylmethyl)-4-(3-fluoro-4-sulfamoylbenzyl)-3-(4'-hydroxy-3'-methyl-[1,1'-biphenyl]-3-yl)-1H-pyrazol-1-yl)thiazole-4-carboxylic acid; MS (ES) 619.0 [M + H]$^+$, LCMS RT = 1.104 min. | +++ |
| 229 | 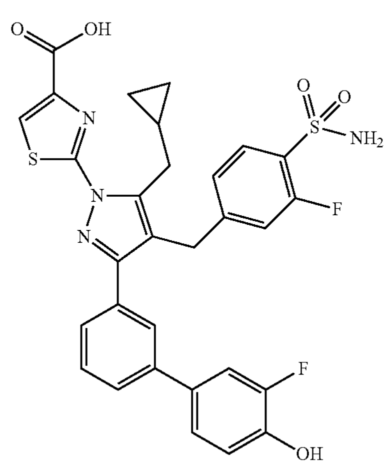 [SMILES: NS(=O)(=O)c1ccc(Cc2c(-c3cccc(-c4ccc(O)c(F)c4)c3)nn(-c3nc(C(=O)O)cs3)c2CC2CC2)cc1F] | 2-(5-(cyclopropylmethyl)-3-(3'-fluoro-4'-hydroxy-[1,1'-biphenyl]-3-yl)-4-(3-fluoro-4-sulfamoylbenzyl)-1H-pyrazol-1-yl)thiazole-4-carboxylic acid; MS (ES) 623.0 [M + H]$^+$, LCMS RT = 1.073 min. | +++ |

TABLE 7-continued

| Cmpd ID | Structure | Compound name and physical data | Inhibitory activity IC$_{50}$ (μM) |
|---|---|---|---|
| 230 | 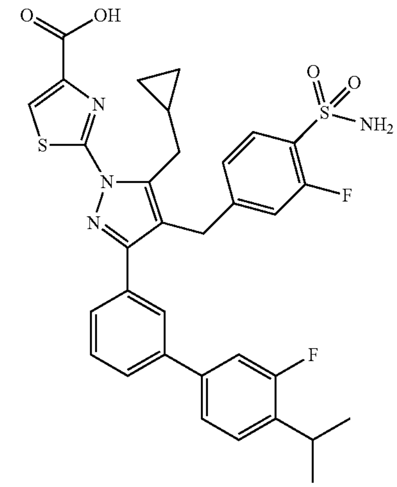 [SMILES: CC(C)c1ccc(-c2cccc(-c3nn(-c4nc(C(=O)O)cs4)c(CC4CC4)c3Cc3ccc(S(N)(=O)=O)c(F)c3)c2)cc1F] | 2-(5-(cyclopropylmethyl)-3-(3'-fluoro-4'-isopropyl-[1,1'-biphenyl]-3-yl)-4-(3-fluoro-4-sulfamoylbenzyl)-1H-pyrazol-1-yl)thiazole-4-carboxylic acid, $^1$H NMR (400 MHz, MeOD-d3) δ 8.15 (s, 1H), 7.80-7.74 (m, 1H), 7.68 (s, 1H), 7.63-7.56 (m, 2H), 7.48-7.43 (m, 1H), 7.38-7.33 (m, 1H), 7.21 (d, J = 11.7 Hz, 1H), 7.16-7.08 (m, 3H), 4.21 (s, 2H), 1.29 (d, J = 6.9 Hz, 6H), 1.20-1.11 (m, 1H), 0.43-0.37 (m, 2H), 0.27-0.22 (m, 2H); MS (ES) 649.0 [M + H]$^+$, LCMS RT = 1.346 min. | ++ |
| 231 | 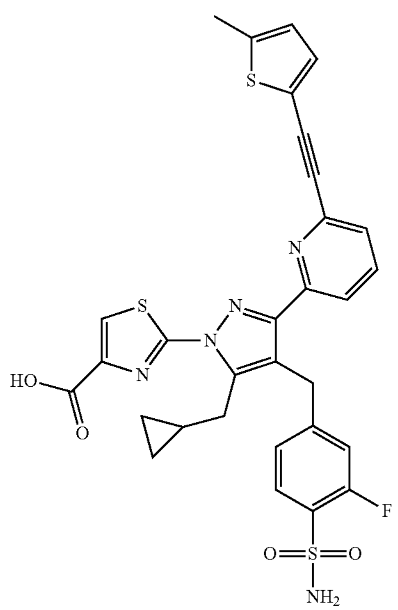 [SMILES: Cc1ccc(C#Cc2cccc(-c3nn(-c4nc(C(=O)O)cs4)c(CC4CC4)c3Cc3ccc(S(N)(=O)=O)c(F)c3)n2)s1] | 2-(5-(cyclopropylmethyl)-4-(3-fluoro-4-sulfamoylbenzyl)-3-(6-((5-methylthiophen-2-yl)ethynyl)pyridin-2-yl)-1H-pyrazol-1-yl)thiazole-4-carboxylic acid, $^1$H NMR (400 MHz, DMSO-d$_6$) δ 13.14 (s, 1H), 8.34 (s, 1H), 7.97 (dd, J = 8.0, 1.1 Hz, 1H), 7.90 (t, J = 7.8 Hz, 1H), 7.60 (t, J = 8.0 Hz, 1H), 7.56 (dd, J = 7.6, 1.1 Hz, 1H), 7.51 (s, 2H), 7.36 (d, J = 3.5 Hz, 1H), 7.26 (dd, J = 11.5, 1.5 Hz, 1H), 7.16 (dd, J = 8.2, 1.6 Hz, 1H), 6.89 (dt, J = 3.6, 1.2 Hz, 1H), 4.38 (s, 2H), 3.26 (d, J = 6.9 Hz, 2H), 1.26-1.15 (m, 1H), 0.43-0.30 (m, 2H), 0.34-0.20 (m, 2H); MS (ES) 634 [M + H]$^+$. | +++ |
| 232 | 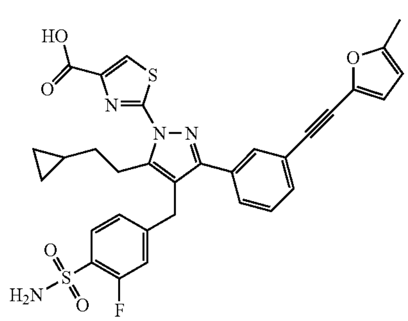 [SMILES: Cc1ccc(C#Cc2cccc(-c3nn(-c4nc(C(=O)O)cs4)c(CCC4CC4)c3Cc3ccc(S(N)(=O)=O)c(F)c3)c2)o1] | 2-(5-(2-cyclopropylethyl)-4-(3-fluoro-4-sulfamoylbenzyl)-3-(3-((5-methylfuran-2-yl)ethynyl)phenyl)-1H-pyrazol-1-yl)thiazole-4-carboxylic acid, $^1$H NMR (400 MHz, DMSO-d$_6$) δ 13.13 (s, 1H), 8.29 (s, 1H), 7.68 (d, J = 7.6 Hz, 2H), 7.58 (s, 3H), 7.58-7.43 (m, 2H), 7.18 (d, J = 11.2 Hz, 1H), 7.07 (d, J = 8.1 Hz, 1H), 6.81 (s, 1H), 6.22 (s, 1H), 4.17 (s, 2H), 3.25 (s, 2H), 2.31 (s, 3H), 1.48-1.38 (m, 2H), 0.74 (s, 1H), 0.31 (d, J = 8.0 Hz, 2H), 0.12 (s, 2H); MS (ES) 631 [M + H]$^+$. | +++ |

TABLE 7-continued

| Cmpd ID | Structure | Compound name and physical data | Inhibitory activity IC$_{50}$ (μM) |
|---|---|---|---|
| 233 | 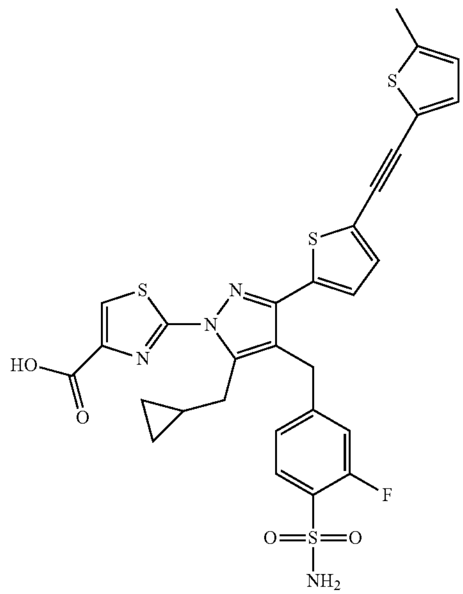 [SMILES: Cc1ccc(C#Cc2ccc(-c3nn(-c4nc(C(=O)O)cs4)c(CC4CC4)c3Cc3ccc(S(N)(=O)=O)c(F)c3)s2)s1] | 2-(5-(cyclopropylmethyl)-4-(3-fluoro-4-sulfamoylbenzyl)-3-(5-((5-methylthiophen-2-yl)ethynyl)thiophen-2-yl)-1H-pyrazol-1-yl)thiazole-4-carboxylic acid, $^1$H NMR (400 MHz, DMSO-d$_6$) δ 13.01 (s, 1H), 8.29 (s, 1H), 7.66 (t, J = 7.9 Hz, 1H), 7.55 (s, 2H), 7.31 (d, J = 3.9 Hz, 1H), 7.23 (dd, J = 3.6, 0.5 Hz, 1H), 7.18 (dd, J = 11.4, 1.6 Hz, 1H), 7.12 (d, J = 3.9 Hz, 1H), 7.07 (dd, J = 8.1, 1.6 Hz, 1H), 6.81 (dt, J = 3.6, 1.1 Hz, 1H), 4.21 (s, 2H), 3.14 (d, J = 6.9 Hz, 2H), 2.44 (d, J = 1.0 Hz, 3H), 1.18-1.02 (m, 0H), 0.36-0.24 (m, 2H), 0.24-0.13 (m, 2H); MS (ES) 639 [M + H]$^+$. | ++ |
| 234 | 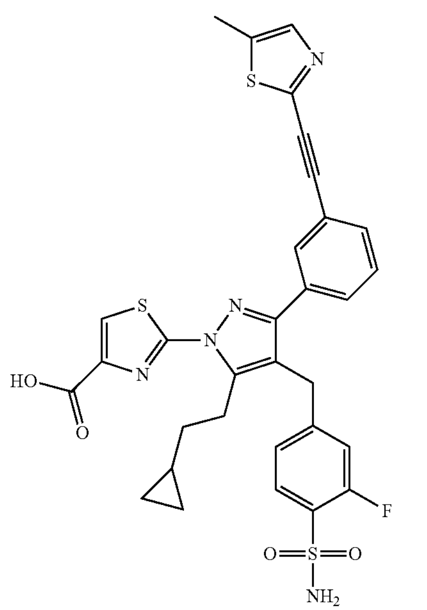 [SMILES: Cc1cnc(C#Cc2cccc(-c3nn(-c4nc(C(=O)O)cs4)c(CCC4CC4)c3Cc3ccc(S(N)(=O)=O)c(F)c3)c2)s1] | 2-(5-(2-cyclopropylethyl)-4-(3-fluoro-4-sulfamoylbenzyl)-3-(3-((5-methylthiazol-2-yl)ethynyl)phenyl)-1H-pyrazol-1-yl)thiazole-4-carboxylic acid, $^1$H NMR (400 MHz, DMSO-d$_6$) δ 13.10 (s, 1H), 8.25 (s, 1H), 7.77 (td, J = 1.7, 0.6 Hz, 1H), 7.68-7.58 (m, 4H), 7.57-7.44 (m, 3H), 7.15 (dd, J = 11.4, 1.5 Hz, 1H), 7.04 (dd, J = 8.2, 1.6 Hz, 1H), 4.16 (s, 2H), 3.26-3.17 (m, 2H), 2.48 (s, 2H), 1.40 (q, J = 7.4 Hz, 2H), 0.75-0.65 (m, 1H), 0.33-0.24 (m, 2H), 0.13-0.04 (m, 2H); MS (ES) 648 [M + H]$^+$. | +++ |

TABLE 7-continued

| Cmpd ID | Structure | Compound name and physical data | Inhibitory activity IC$_{50}$ (μM) |
|---|---|---|---|
| 235 | 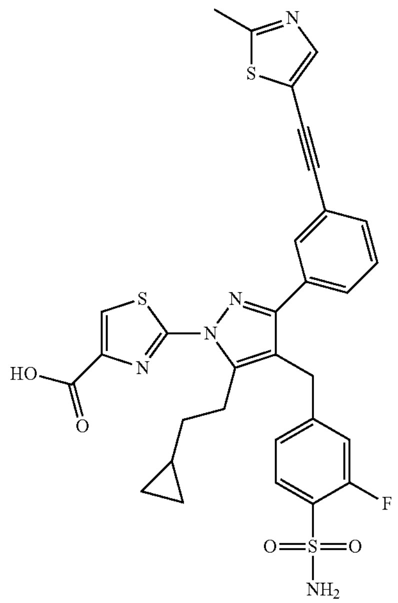 [SMILES: Cc1ncc(C#Cc2cccc(-c3nn(-c4nc(C(=O)O)cs4)c(CCC4CC4)c3Cc3ccc(S(N)(=O)=O)c(F)c3)c2)s1] | 2-(5-(2-cyclopropylethyl)-4-(3-fluoro-4-sulfamoylbenzyl)-3-(3-((2-methylthiazol-5-yl)ethynyl)phenyl)-1H-pyrazol-1-yl)thiazole-4-carboxylic acid, $^1$H NMR (400 MHz, DMSO-d$_6$) δ 13.13 (s, 1H), 8.28 (s, 1H), 7.96 (s, 1H), 7.74-7.62 (m, 2H), 7.65-7.53 (m, 4H), 7.48 (td, J = 7.7, 0.6 Hz, 1H), 7.19 (dd, J = 11.3, 1.5 Hz, 1H), 7.07 (dd, J = 8.1, 1.6 Hz, 1H), 4.18 (s, 2H), 3.24 (d, J = 8.3 Hz, 2H), 2.69 (s, 3H), 1.43 (q, J = 7.4 Hz, 2H), 0.74 (td, J = 7.5, 3.8 Hz, 0H), 0.36-0.27 (m, 2H), 0.16-0.08 (m, 2H); MS (ES) 648 [M + H]$^+$. | +++ |
| 236 | 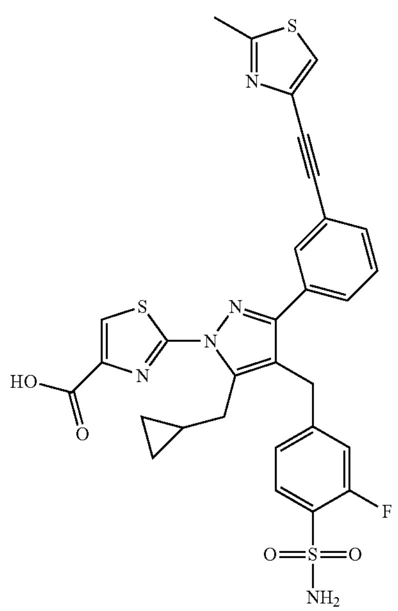 [SMILES: Cc1nc(C#Cc2cccc(-c3nn(-c4nc(C(=O)O)cs4)c(CC4CC4)c3Cc3ccc(S(N)(=O)=O)c(F)c3)c2)cs1] | 2-(5-(cyclopropylmethyl)-4-(3-fluoro-4-sulfamoylbenzyl)-3-(3-((2-methylthiazol-4-yl)ethynyl)phenyl)-1H-pyrazol-1-yl)thiazole-4-carboxylic acid, $^1$H NMR (400 MHz, DMSO-d$_6$) δ 13.16 (s, 1H), 8.32 (s, 1H), 7.91 (s, 1H), 7.79-7.52 (m, 7H), 7.47 (t, J = 7.8 Hz, 1H), 7.16 (dd, J = 11.3, 1.5 Hz, 1H), 7.07 (dd, J = 8.1, 1.6 Hz, 1H), 4.19 (s, 2H), 3.18 (d, J = 6.9 Hz, 2H), 2.68 (s, 3H), 1.21-1.08 (m, 1H), 0.40-0.26 (m, 2H), 0.30-0.19 (m, 2H); MS (ES) 634 [M + H]$^+$. | +++ |

TABLE 7-continued

| Cmpd ID | Structure | Compound name and physical data | Inhibitory activity IC$_{50}$ (μM) |
|---|---|---|---|
| 237 | 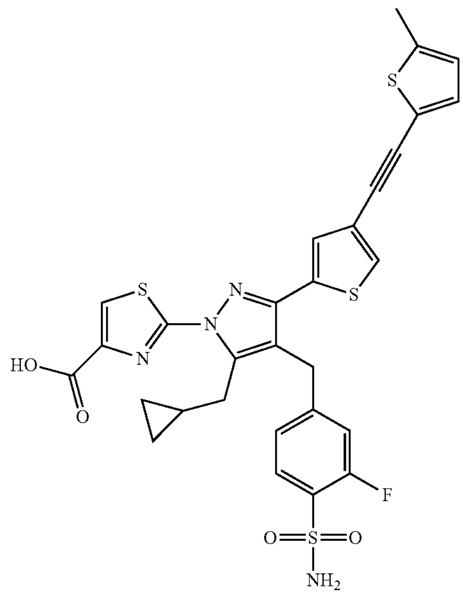 [SMILES: Cc1ccc(C#Cc2csc(-c3nn(-c4nc(C(=O)O)cs4)c(CC4CC4)c3Cc3ccc(S(N)(=O)=O)c(F)c3)c2)s1] | 2-(5-(cyclopropylmethyl)-4-(3-fluoro-4-sulfamoylbenzyl)-3-(4-((5-methylthiophen-2-yl)ethynyl)thiophen-2-yl)-1H-pyrazol-1-yl)thiazole-4-carboxylic acid, $^1$H NMR (400 MHz, DMSO-d$_6$) δ 13.15 (s, 1H), 8.30 (s, 1H), 7.91 (d, J = 1.3 Hz, 1H), 7.69 (t, J = 8.0 Hz, 1H), 7.58 (s, 2H), 7.33 (d, J = 1.3 Hz, 1H), 7.26-7.08 (m, 3H), 6.81 (dq, J = 3.4, 1.0 Hz, 1H), 4.25 (s, 2H), 3.16 (d, J = 6.9 Hz, 2H), 2.46 (d, J = 1.1 Hz, 3H), 1.22-1.04 (m, 1H), 0.36-0.28 (m, 2H), 0.23-0.15 (m, 2H); MS (ES) 639 [M + H]$^+$. | ++ |
| 238 | 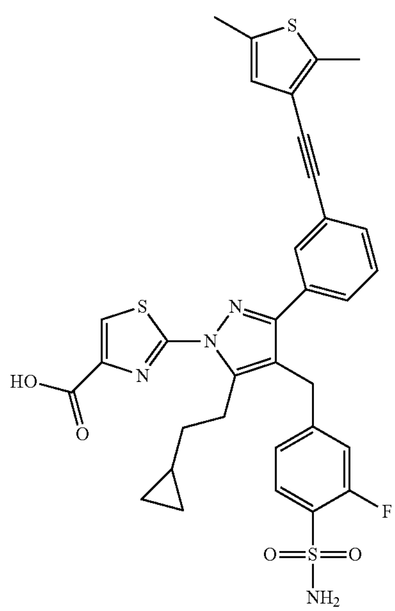 [SMILES: Cc1cc(C#Cc2cccc(-c3nn(-c4nc(C(=O)O)cs4)c(CCC4CC4)c3Cc3ccc(S(N)(=O)=O)c(F)c3)c2)c(C)s1] | 2-(5-(2-cyclopropylethyl)-3-(3-((2,5-dimethylthiophen-3-yl)ethynyl)phenyl)-4-(3-fluoro-4-sulfamoylbenzyl)-1H-pyrazol-1-yl)thiazole-4-carboxylic acid, $^1$H NMR (400 MHz, DMSO-d$_6$) δ 13.13 (s, 1H), 8.28 (s, 1H), 7.68 (t, J = 7.9 Hz, 1H), 7.63-7.56 (m, 4H), 7.52 (dt, J = 7.7, 1.5 Hz, 1H), 7.46 (td, J = 7.6, 0.7 Hz, 1H), 7.21 (dd, J = 11.4, 1.6 Hz, 1H), 7.09 (dd, J = 8.2, 1.6 Hz, 1H), 6.77 (q, J = 1.1 Hz, 1H), 4.17 (s, 2H), 3.29-3.20 (m, 2H), 2.44 (d, J = 0.7 Hz, 3H), 2.38 (t, J = 0.9 Hz, 3H), 1.44 (q, J = 7.2 Hz, 2H), 0.80-0.67 (m, 1H), 0.39-0.27 (m, 2H), 0.18-0.08 (m, 2H), MS (ES) 661 [M + H]$^+$. | ++ |

TABLE 7-continued

| Cmpd ID | Structure | Compound name and physical data | Inhibitory activity IC$_{50}$ (μM) |
|---|---|---|---|
| 239 | 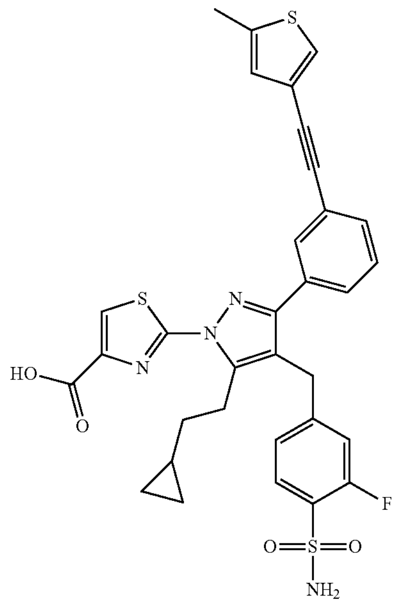 [SMILES: Cc1cc(C#Cc2cccc(-c3nn(-c4nc(C(=O)O)cs4)c(CCC4CC4)c3Cc3ccc(S(N)(=O)=O)c(F)c3)c2)cs1] | 2-(5-(2-cyclopropylethyl)-4-(3-fluoro-4-sulfamoylbenzyl)-3-(3-((5-methylthiophen-3-yl)ethynyl)phenyl)-1H-pyrazol-1-yl)thiazole-4-carboxylic acid, $^1$H NMR (400 MHz, DMSO-d$_6$) δ 13.13 (s, 1H), 8.29 (s, 1H), 7.73-7.41 (m, 7H), 7.20 (dd, J = 11.3, 1.6 Hz, 1H), 7.08 (dd, J = 8.1, 1.6 Hz, 1H), 6.95 (p, J = 1.1 Hz, 1H), 4.17 (s, 2H), 3.30-3.21 (m, 2H), 2.46 (d, J = 1.1 Hz, 3H), 1.44 (q, J = 7.2 Hz, 2H), 0.75 (tq, J = 8.0, 5.0, 3.9 Hz, 1H), 0.37-0.25 (m, 2H), 0.19-0.08 (m, 2H); MS (ES) 647 [M + H]$^+$. | ++ |
| 240 | 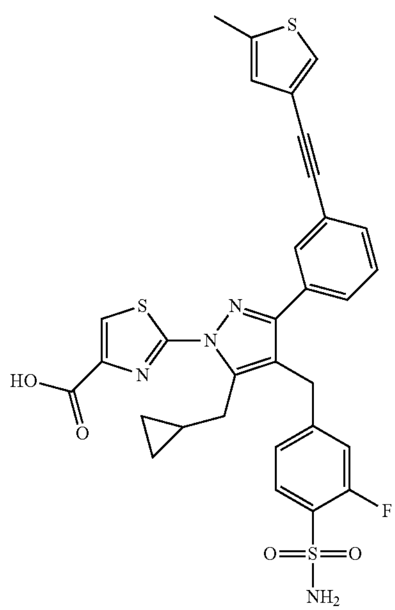 [SMILES: Cc1cc(C#Cc2cccc(-c3nn(-c4nc(C(=O)O)cs4)c(CC4CC4)c3Cc3ccc(S(N)(=O)=O)c(F)c3)c2)cs1] | 2-(5-(cyclopropylmethyl)-4-(3-fluoro-4-sulfamoylbenzyl)-3-(3-((5-methylthiophen-3-yl)ethynyl)phenyl)-1H-pyrazol-1-yl)thiazole-4-carboxylic acid, $^1$H NMR (400 MHz, DMSO-d$_6$) δ 13.16 (s, 1H), 8.31 (s, 1H), 7.71-7.40 (m, 7H), 7.18 (dd, J = 11.3, 1.6 Hz, 1H), 7.07 (dd, J = 8.2, 1.6 Hz, 1H), 6.95 (p, J = 1.1 Hz, 1H), 4.18 (s, 2H), 3.18 (d, J = 6.9 Hz, 2H), 2.46 (d, J = 1.1 Hz, 3H), 1.22-1.07 (m, 0H), 0.40-0.29 (m, 2H), 0.30-0.19 (m, 2H); MS (ES) 633 [M + H]$^+$. | +++ |

| Cmpd ID | Structure | Compound name and physical data | Inhibitory activity IC$_{50}$ (μM) |
|---|---|---|---|
| 241 | 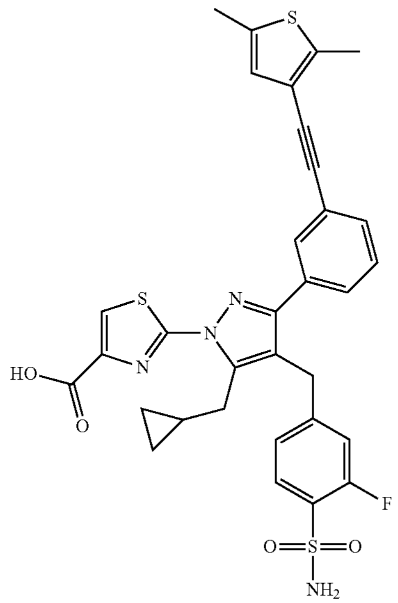 | 2-(5-(cyclopropylmethyl)-3-(3-((2,5-dimethylthiophen-3-yl)ethynyl)phenyl)-4-(3-fluoro-4-sulfamoylbenzyl)-1H-pyrazol-1-yl)thiazole-4-carboxylic acid, $^1$H NMR (400 MHz, DMSO-d$_6$) δ 13.16 (s, 1H), 8.31 (s, 1H), 7.67 (t, J = 8.0 Hz, 1H), 7.65-7.56 (m, 4H), 7.55-7.40 (m, 2H), 7.18 (dd, J = 11.3, 1.5 Hz, 1H), 7.08 (dd, J = 8.1, 1.6 Hz, 1H), 6.77 (q, J = 1.1 Hz, 1H), 4.18 (s, 2H), 3.17 (d, J = 6.9 Hz, 2H), 2.44 (d, J = 0.7 Hz, 3H), 2.38 (t, J = 0.9 Hz, 3H), 1.20-1.09 (m, 1H), 0.39-0.28 (m, 2H), 0.29-0.18 (m, 2H); MS (ES) 633 [M + H]$^+$. | ++ |
| 242 | 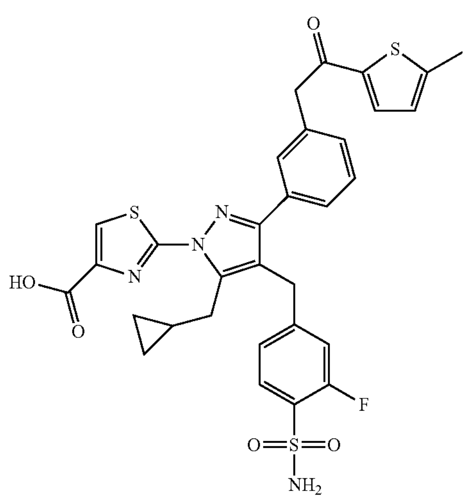 [SMILES: Cc1ccc(C(=O)Cc2cccc(-c3nn(-c4nc(C(=O)O)cs4)c(CC4CC4)c3Cc3ccc(S(N)(=O)=O)c(F)c3)c2)s1] | 2-(5-(cyclopropylmethyl)-4-(3-fluoro-4-sulfamoylbenzyl)-3-(3-(2-(5-methylthiophen-2-yl)-2-oxoethyl)phenyl)-1H-pyrazol-1-yl)thiazole-4-carboxylic acid, $^1$H NMR (400 MHz, DMSO-d$_6$) δ 13.14 (s, 1H), 8.29 (s, 1H), 7.91 (d, J = 3.7 Hz, 1H), 7.66-7.53 (m, 4H), 7.45-7.25 (m, 3H), 7.08 (dd, J = 11.4, 1.6 Hz, 1H), 7.08-6.94 (m, 2H), 4.26 (s, 2H), 4.13 (s, 2H), 3.16 (d, J = 6.9 Hz, 2H), 2.49 (s, 3H), 1.13 (ddtd, J = 13.0, 8.0, 6.9, 5.0 Hz, 1H), 0.39-0.27 (m, 2H), 0.30-0.17 (m, 2H); MS (ES) 651 [M + H]$^+$. | +++ |

TABLE 7-continued

| Cmpd ID | Structure | Compound name and physical data | Inhibitory activity IC$_{50}$ (µM) |
|---|---|---|---|
| 243 | 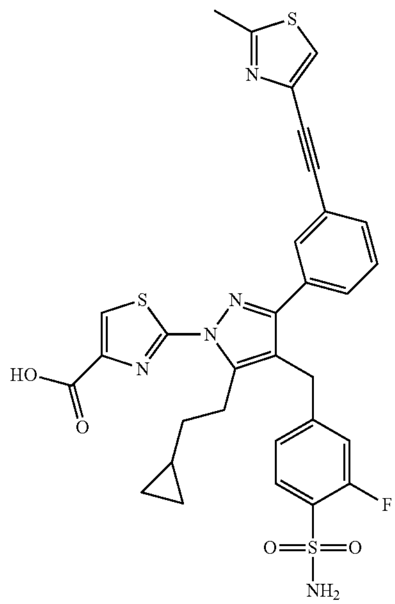 [SMILES: Cc1nc(C#Cc2cccc(-c3nn(-c4nc(C(=O)O)cs4)c(CCC4CC4)c3Cc3ccc(S(N)(=O)=O)c(F)c3)c2)cs1] | 2-(5-(2-cyclopropylethyl)-4-(3-fluoro-4-sulfamoylbenzyl)-3-(3-((2-methylthiazol-4-yl)ethynyl)phenyl)-1H-pyrazol-1-yl)thiazole-4-carboxylic acid, $^1$H NMR (400 MHz, DMSO-d$_6$) δ 13.13 (s, 1H), 8.30 (s, 1H), 7.92 (s, 1H), 7.76-7.63 (m, 2H), 7.59 (s, 2H), 7.64-7.54 (m, 2H), 7.53-7.44 (m, 1H), 7.19 (dd, J = 11.3, 1.6 Hz, 1H), 7.08 (dd, J = 8.1, 1.6 Hz, 1H), 4.18 (s, 2H), 3.29-3.20 (m, 2H), 2.68 (s, 3H), 1.43 (q, J = 7.3 Hz, 2H), 0.82-0.67 (m, 1H), 0.38-0.25 (m, 2H), 0.19-0.08 (m, 2H); MS (ES) 648 [M + H]$^+$. | +++ |
| 244 | 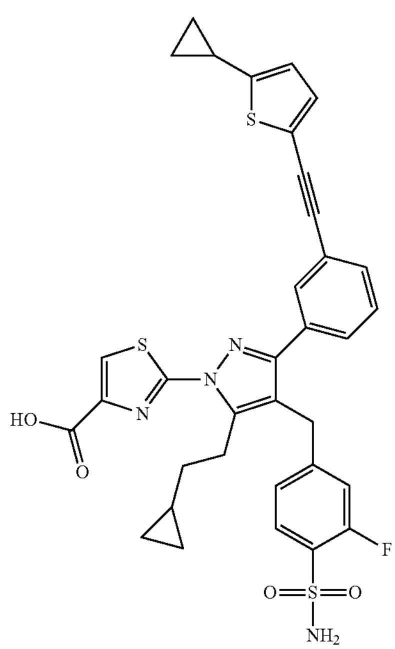 [SMILES: NS(=O)(=O)c1ccc(Cc2c(-c3cccc(C#Cc4ccc(C5CC5)s4)c3)nn(-c3nc(C(=O)O)cs3)c2CCC2CC2)cc1F] | 2-(5-(2-cyclopropylethyl)-3-(3-((5-cyclopropylthiophen-2-yl)ethynyl)phenyl)-4-(3-fluoro-4-sulfamoylbenzyl)-1H-pyrazol-1-yl)thiazole-4-carboxylic acid, $^1$H NMR (400 MHz, DMSO-d$_6$) δ 13.13 (s, 1H), 8.28 (s, 1H), 7.72-7.63 (m, 2H), 7.66-7.48 (m, 4H), 7.46 (t, J = 7.7 Hz, 1H), 7.25-7.14 (m, 2H), 7.07 (dd, J = 8.2, 1.6 Hz, 1H), 6.82 (dd, J = 3.7, 0.7 Hz, 1H), 4.17 (s, 2H), 3.29-3.20 (m, 2H), 2.17 (tt, J = 8.3, 5.1 Hz, 1H), 1.43 (q, J = 7.4 Hz, 2H), 1.11-0.98 (m, 2H), 0.81-0.67 (m, 3H), 0.36-0.25 (m, 2H), 0.19-0.08 (m, 2H); MS (ES) 673 [M + H]$^+$. | ++ |

| Cmpd ID | Structure | Compound name and physical data | Inhibitory activity IC$_{50}$ (μM) |
|---|---|---|---|
| 245 | 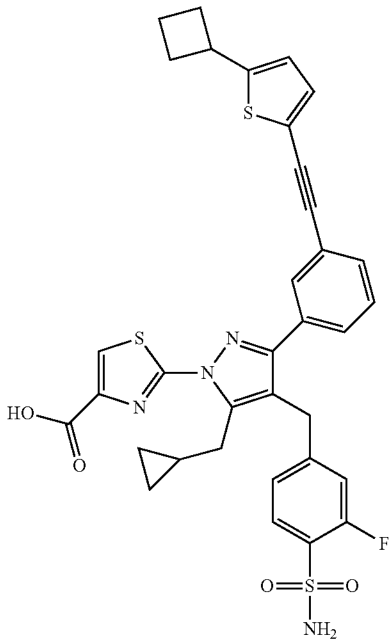 [SMILES: NS(=O)(=O)c1ccc(Cc2c(-c3cccc(C#Cc4ccc(C5CCC5)s4)c3)nn(-c3nc(C(=O)O)cs3)c2CC2CC2)cc1F] | 2-(3-(3-((5-cyclobutylthiophen-2-yl)ethynyl)phenyl)-5-(cyclopropylmethyl)-4-(3-fluoro-4-sulfamoylbenzyl)-1H-pyrazol-1-yl)thiazole-4-carboxylic acid, $^1$H NMR (400 MHz, DMSO-d$_6$) δ 13.16 (s, 1H), 8.31 (s, 1H), 7.71-7.62 (m, 2H), 7.66-7.54 (m, 3H), 7.52 (dt, J = 7.7, 1.4 Hz, 1H), 7.49-7.40 (m, 1H), 7.26 (d, J = 3.6 Hz, 1H), 7.16 (dd, J = 11.4, 1.6 Hz, 1H), 7.07 (dd, J = 8.1, 1.6 Hz, 1H), 6.88 (dd, J = 3.7, 0.9 Hz, 1H), 4.18 (s, 2H), 3.79-3.65 (m, 1H), 3.18 (d, J = 6.9 Hz, 2H), 2.45-2.32 (m, 2H), 2.19-2.04 (m, 2H), 2.05-1.88 (m, 1H), 1.91-1.78 (m, 1H), 1.21-1.08 (m, 1H), 0.41-0.27 (m, 2H), 0.31-0.16 (m, 2H), MS (ES) 673 [M + H]$^+$. | ++ |
| 246 | 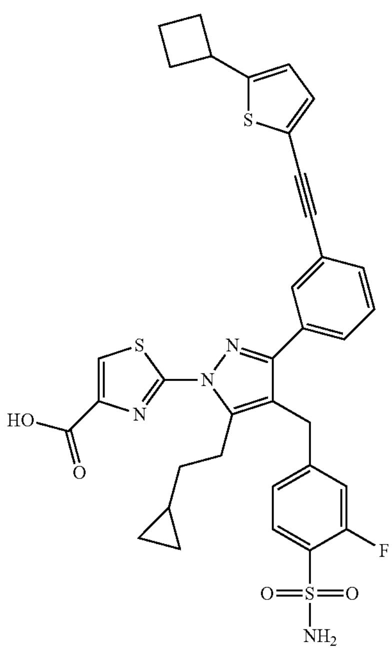 [SMILES: NS(=O)(=O)c1ccc(Cc2c(-c3cccc(C#Cc4ccc(C5CCC5)s4)c3)nn(-c3nc(C(=O)O)cs3)c2CCC2CC2)cc1F] | 2-(3-(3-((5-cyclobutylthiophen-2-yl)ethynyl)phenyl)-5-(2-cyclopropylethyl)-4-(3-fluoro-4-sulfamoylbenzyl)-1H-pyrazol-1-yl)thiazole-4-carboxylic acid, $^1$H NMR (400 MHz, DMSO-d$_6$) δ 13.13 (s, 1H), 8.28 (s, 1H), 7.72-7.61 (m, 2H), 7.62-7.49 (m, 4H), 7.46 (td, J = 7.7, 0.6 Hz, 1H), 7.26 (d, J = 3.7 Hz, 1H), 7.19 (dd, J = 11.4, 1.6 Hz, 1H), 7.08 (dd, J = 8.1, 1.6 Hz, 1H), 6.88 (dd, J = 3.7, 0.9 Hz, 1H), 4.17 (s, 2H), 3.79-3.65 (m, 1H), 3.29-3.21 (m, 2H), 2.47-2.36 (m, 1H), 2.40-2.32 (m, 1H), 2.19-2.04 (m, 2H), 2.09-1.88 (m, 1H), 1.91-1.78 (m, 1H), 1.43 (q, J = 7.4 Hz, 2H), 0.74 (td, J = 7.8, 4.8 Hz, 1H), 0.36-0.25 (m, 2H), 0.20-0.08 (m, 2H); MS (ES) 687 [M + H]$^+$. | ++ |

TABLE 7-continued

| Cmpd ID | Structure | Compound name and physical data | Inhibitory activity IC$_{50}$ (μM) |
|---|---|---|---|
| 247 | 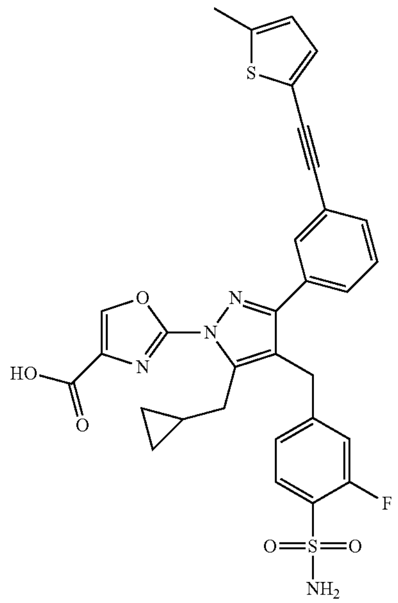 [SMILES: Cc1ccc(C#Cc2cccc(-c3nn(-c4nc(C(=O)O)co4)c(CC4CC4)c3Cc3ccc(S(N)(=O)=O)c(F)c3)c2)s1] | 2-(5-(cyclopropylmethyl)-4-(3-fluoro-4-sulfamoylbenzyl)-3-(3-((5-methylthiophen-2-yl)ethynyl)phenyl)-1H-pyrazol-1-yl)oxazole-4-carboxylic acid, MS (ES) 617 [M + H]⁺. | +++ |
| 248 | 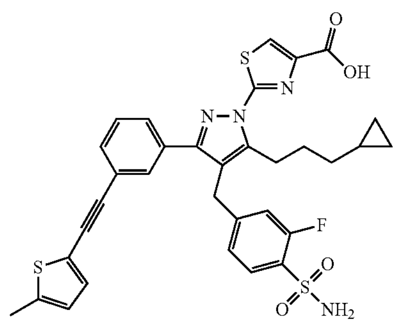 | 2-(5-(3-cyclopropylpropyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, MS (ES) 617 [M + H]⁺. | ++ |
| 249 | 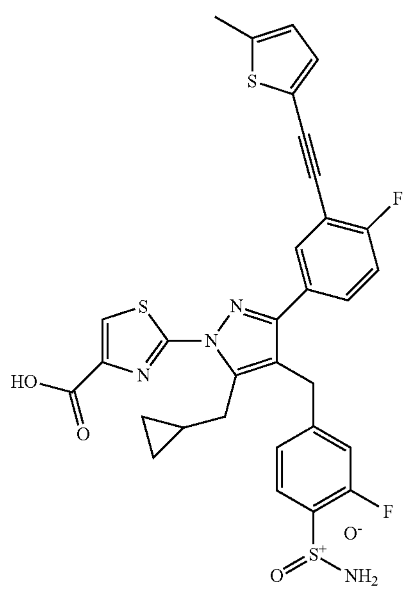 | 2-(5-(cyclopropylmethyl)-3-(4-fluoro-3-((5-methylthiophen-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.18 (s, 1H), 8.32 (s, 1H), 7.74 (dd, J = 6.9, 2.3 Hz, 1H), 7.66 (t, J = 7.9 Hz, 1H), 7.61 (ddd, J = 8.6, 5.0, 2.3 Hz, 1H), 7.59 (s, 2H), 7.37 (dd, J = 9.4, 8.7 Hz, 1H), 7.29 (dd, J = 3.6, 0.5 Hz, 1H), 7.17 (dd, J = 11.3, 1.6 Hz, 1H), 7.06 (dd, J = 8.1, 1.6 Hz, 1H), 6.86 (dt, J = 3.6, 1.1 Hz, 1H), 4.17 (s, 2H), 3.18 (d, J = 6.9 Hz, 2H), 2.48 (d, J = 1.1 Hz, 3H), 1.21-1.08 (m, 1H), 0.40-0.28 (m, 2H), 0.30-0.19 (m, 2H); MS [M + H]+ = 651 | +++ |

TABLE 7-continued

| Cmpd ID | Structure | Compound name and physical data | Inhibitory activity IC$_{50}$ (μM) |
|---|---|---|---|
| 250 | 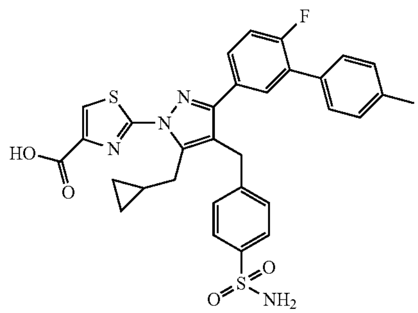 [SMILES: Cc1ccc(-c2cc(-c3nn(-c4nc(C(=O)O)cs4)c(CC4CC4)c3Cc3ccc(S(N)(=O)=O)cc3)ccc2F)cc1] | 2-(5-(cyclopropylmethyl)-3-(6-fluoro-4'-methyl-[1,1'-biphenyl]-3-yl)-4-(4-sulfamoylbenzyl)-1H-pyrazol-1-yl)thiazole-4-carboxylic acid | |
| 251 | 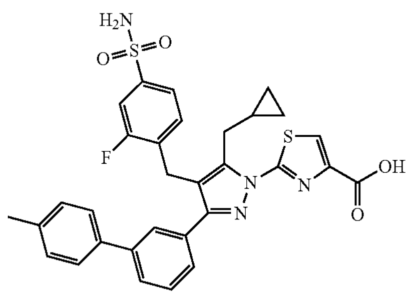 [SMILES: Cc1ccc(-c2cccc(-c3nn(-c4nc(C(=O)O)cs4)c(CC4CC4)c3Cc3ccc(S(N)(=O)=O)cc3F)c2)cc1] | 2-(5-(cyclopropylmethyl)-4-(2-fluoro-4-sulfamoylbenzyl)-3-(4'-methyl-[1,1'-biphenyl]-3-yl)-1H-pyrazol-1-yl)thiazole-4-carboxylic acid | |
| 252 | 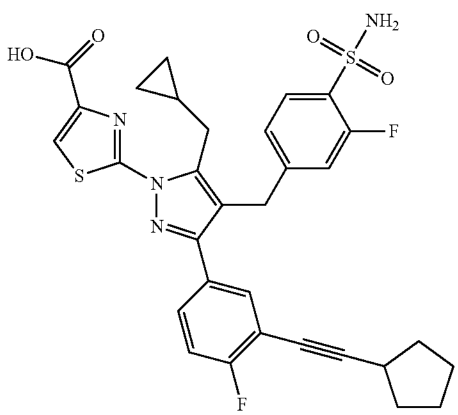 [SMILES: NS(=O)(=O)c1ccc(Cc2c(-c3ccc(F)c(C#CC4CCCC4)c3)nn(-c3nc(C(=O)O)cs3)c2CC2CC2)cc1F] | 2-(3-(3-(cyclopentylethynyl)-4-fluorophenyl)-5-(cyclopropylmethyl)-4-(3-fluoro-4-sulfamoylbenzyl)-1H-pyrazol-1-yl)thiazole-4-carboxylic acid | |

What is claimed is:

1. A method of treating a disease or disorder associated with elevated oxalate levels in a patient, the method comprising administering to the patient a therapeutically effective amount of a compound of Formula I, or a pharmaceutically acceptable salt thereof, wherein the compound of Formula I is 2-(5-(cyclopropylmethyl)-3-(6-fluoro-4'-methyl-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-4'-(trifluoromethyl)-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-2'-methyl-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-4'-methoxy-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(4-fluoro-3-(1H-inden-2-yl) phenyl)-4-(3-fluoro-4-sulfamoylbenzyl)-1H-pyrazol-1-yl) thiazole-4-carboxylic acid, 2-(5-(cyclopropylmethyl)-3-(6-fluoro-4',4'-dimethyl-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4',4',6-trifluoro-2',3',4',5'-tetrahydro-[1,1'-biphenyl]-3-yl)-1H-pyrazol-1-yl) thiazole-4-carboxylic acid, 2-(5-(cyclopropylmethyl)-3-(4-fluoro-3-(spiro[2.5] oct-5-en-6-yl) phenyl)-4-(3-fluoro-4-sulfamoylbenzyl)-1H-pyrazol-1-yl) thiazole-4-carboxylic acid, 2-(3-(3-(but-1-yn-1-yl)-4-fluorophenyl)-5-(cyclopropylmethyl)-4-(3-fluoro-4-sulfamoylbenzyl)-1H-pyrazol-1-yl) thiazole-4-carboxylic acid, 2-(3-(3-((5-(tert-butyl) thiophen-2-yl) ethynyl)-4-fluorophenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(4-fluoro-3-((2-methylthiazol-5-yl)ethynyl)phenyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 2-(5-(2-cyclopropylethyl)-3-(4-fluoro-3-((5-methylthiophen-2-yl) ethynyl) phenyl)-4-(3-fluoro-4-sulfamoylbenzyl)-1H-pyrazol-1-yl)thiazole-4-carboxylic acid, 2-(5-(cyclopropylmethyl)-3-(4-fluoro-3-((5-methylthiazol-2-yl)ethynyl)phenyl)-4-(3-fluoro-4-sulfamoylbenzyl)-1H-pyrazol-1-yl)thiazole-4-carboxylic acid, 2-(5-(2-cyclopropylethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 2-(5-(1-cyclopropylethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 2-(5-(cyclopropylmethyl)-3-(3-((5-cyclopropylthiophen-2-yl ethynyl)phenyl)-4-(3-fluoro-4-sulfamoylbenzyl)-1H-pyrazol-1-yl)thiazole-4-carboxylic acid, 2-(3-(3-((5-chlorothiophen-2-yl)ethynyl)phenyl)-5-(cyclopropylmethyl)-4-(3-fluoro-4-sulfamoylbenzyl)-1H-pyrazol-1-yl)thiazole-4-carboxylic, (E)-2-(5-(cyclopropylmethyl)-4-(3-fluoro-4-sulfamoylbenzyl)-3-(3-(2-(5-methylthiophen-2-yl)vinyl)phenyl)-1H-pyrazol-1-yl)thiazole-4-carboxylic acid, 2-(5-(cyclopropylmethyl)-4-(3-fluoro-4-sulfamoylbenzyl)-3-(3-((3-methylthiophen-2-yl)ethynyl)phenyl)-1H-pyrazol-1-yl)thiazole-4-carboxylic acid, 2-(5-(cyclopropylmethyl)-3-(3-((5-(difluoromethyl) thiophen-2-yl)ethynyl)phenyl)-4-(3-fluoro-4-sulfamoylbenzyl)-1H-pyrazol-1-yl)thiazole-4-carboxylic acid, 2-(5-(cyclopropylmethyl)-4-(3-fluoro-4-sulfamoylbenzyl)-3-(3-((5-methyloxazol-2-yl)ethynyl)phenyl)-1H-pyrazol-1-yl)thiazole-4-carboxylic acid, 2-(4-(3-fluoro-4-sulfamoylbenzyl)-5-((1-methylcyclopropyl) methyl)-3-(3-((5-methylthiophen-2-yl)ethynyl) phenyl)-1H-pyrazol-1-yl)thiazole-4-carboxylic acid, 2-(5-(cyclopropylmethyl)-4-(3-fluoro-4-sulfamoylbenzyl)-3-(3-((5-(trifluoromethyl)thiophen-2-yl)ethynyl) phenyl)-1H-pyrazol-1-yl)thiazole-4-carboxylic acid, 2-(5-(cyclopropylmethyl)-3-(3-((3,5-dimethylthiophen-2-yl)ethynyl)phenyl)-4-(3-fluoro-4-sulfamoylbenzyl)-1H-pyrazol-1-yl)thiazole-4-carboxylic, 2-(5-(cyclopropylmethyl)-4-(3-fluoro-4-sulfamoylbenzyl)-3-(3-((5-isopropylthiophen-2-yl)ethynyl)phenyl)-1H-pyrazol-1-yl)thiazole-4-carboxylic acid, 2-(5-(2-cyclopropylpropan-2-yl)-4-(3-fluoro-4-sulfamoylbenzyl)-3-(3-((5-methylthiophen-2-yl)ethynyl) phenyl)-1H-pyrazol-1-yl)thiazole-4-carboxylic acid, 2-(5-(cyclopropylmethyl)-4-(3-fluoro-4-sulfamoylbenzyl)-3-(3-((5-methylfuran-2-yl)ethynyl)phenyl)-1H-pyrazol-1-yl)thiazole-4-carboxylic acid, 2-(5-(cyclopropylmethyl)-4-(3-fluoro-4-sulfamoylbenzyl)-3-(3-(2-(5-methylthiophen-2-yl)cyclopropyl)phenyl)-1H-pyrazol-1-yl)thiazole-4-carboxylic acid, 2-(4-(3-fluoro-4-sulfamoylbenzyl)-3-(3-((5-methylthiophen-2-yl)ethynyl)phenyl)-5-(spiro[2.2] pentan-1-yl)-1H-pyrazol-1-yl)thiazole-4-carboxylic acid, 2-(5-(cyclopropylmethyl)-4-(3-fluoro-4-sulfamoylbenzyl)-3-(3-((cis)-3-(5-methylthiophen-2-yl)cyclobutyl) phenyl)-1H-pyrazol-1-yl)thiazole-4-carboxylic acid, 2-(5-(cyclopropylmethyl)-4-(3-fluoro-4-sulfamoylbenzyl)-3-(3-(3-(5-methylthiophen-2-yl)cyclobutyl)phenyl)-1H-pyrazol-1-yl)thiazole-4-carboxylic acid, 2-(5-([1, 1'-bi (cyclopropan)]-2-yl)-4-(3-fluoro-4-sulfamoylbenzyl)-3-(3-(((5-methylthiophen-2-yl)ethynyl) phenyl)-1H-pyrazol-1-yl)thiazole-4-carboxylic acid, 2-(5-(cyclopropylmethyl)-4-(3-fluoro-4-sulfamoylbenzyl)-3-(3',4',6-trifluoro-[1,1'-biphenyl]-3-yl)-1H-pyrazol-1-yl)thiazole-4-carboxylic acid, 2-(5-(cyclopropylmethyl)-3-(3',6-difluoro-4'-methyl-[1,1'-biphenyl]-3-yl)-4-(3-fluoro-4-sulfamoylbenzyl)-1H-pyrazol-1-yl)thiazole-4-carboxylic acid, 2-(5-(cyclopropylmethyl)-3-(6-fluoro-4'-(trifluoromethyl)-[1,1'-biphenyl]-3-yl)-4-(3-fluoro-4-sulfamoylbenzyl)-1H-pyrazol-1-yl)thiazole-4-carboxylic acid, 2-(3-(4-chloro-6-fluoro-[1, 1'-biphenyl]-3-yl)-5-(cyclopropylmethyl)-4-(3-fluoro-4-sulfamoylbenzyl)-1H-pyrazol-1-yl)thiazole-4-carboxylic acid, 2-(3-(3-acetyl-4-fluorophenyl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(6-fluoro-3'-methyl-[1,1'-biphenyl]-3-yl)-4-(3-fluoro-4-sulfamoylbenzyl)-1H-pyrazol-1-yl)thiazole-4-carboxylic acid, 2-(5-(cyclopropylmethyl)-3-(6-fluoro-4'-isopropyl-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(4-fluoro-3-(5,6,7,8-tetrahydronaphthalen-2-yl) phenyl)-4-(3-fluoro-4-sulfamoylbenzyl)-1H-pyrazol-1-yl)thiazole-4-carboxylic acid, 2-(3-(4'-chloro-3',6-difluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(3-(pyrrolidine-1-carbonyl) phenyl)-4-(4-sulfamoylbenzyl)-1H-pyrazol-1-yl)thiazole-4-carboxylic acid, 2-(5-(cyclopropylmethyl)-3-(6-fluoro-2',3',4',5'-tetrahydro-[1,1'-biphenyl]-3-yl)-4-(3-fluoro-4-sulfamoylbenzyl)-1H-pyrazol-1-yl)thiazole-4-carboxylic acid, 2-(3-(3-(tert-butylcarbamoyl)-4-fluorophenyl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(3-(4,5-dihydrofuran-2-yl)-4-fluorophenyl)-4-(3-fluoro-4-sulfamoylbenzyl)-1H-pyrazol-1-yl)thiazole-4-carboxylic acid, 2-(3-(3'-chloro-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(6-fluoro-4'-methoxy-3'-methyl-[1,1'-biphenyl]-3-yl)-4-(3-fluoro-4-sulfamoylbenzyl)-1H-pyrazol-1-yl)thiazole-4-carboxylic, 2-(5-(cyclopropylmethyl)-3-(6-fluoro-3',5'-dimethyl-[1,1'-biphenyl]-3-yl)-4-(3-fluoro-4-sulfamoylbenzyl)-1H-pyrazol-1-yl)thiazole-4-carboxylic acid, 2-(3-(3-benzamido-4-fluorophenyl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(6-fluoro-3',5'-dimethoxy-[1,1'-biphenyl]-3-yl)-4-(3-fluoro-4-sulfamoylbenzyl)-1H-pyrazol-1-yl)thiazole-4-carboxylic acid, 2-(5-(cyclopropylmethyl)-3-(4-fluoro-3-(2-oxopyrrolidin-1-yl) phenyl)-4-(3-fluoro-4-sulfamoylbenzyl)-1H-pyrazol-1-yl)thiazole-4-carboxylic acid, 2-(5-(cyclopropylmethyl)-3-(3-(2,3-dihydro-1H-inden-5-yl)-4-fluorophenyl)-4-(3-fluoro-4-sulfamoylbenzyl)-1H-pyrazol-1-yl)thiazole-4-carboxylic acid, 2-(5-(cyclopropylmethyl)-4-(3-fluoro-4-sulfamoylbenzyl)-3-(3',5',6-trifluoro-[1,1'-biphenyl]-3-yl)-1H-pyrazol-1-yl)thiazole-4-carboxylic acid, 2-(5-(cyclopropylmethyl)-3-(3',5'-dichloro-6-fluoro-[1,1'-biphenyl]-3-yl)-4-(3-fluoro-4-sulfamoylbenzyl)-1H-pyrazol-1-yl)thiazole-4-carboxylic acid, 2-(5-(cyclopropylmethyl)-3-(4-fluoro-3-(6-isopropyl-2,6-diazaspiro[3.3] heptan-2-yl)phenyl)-4-(3-fluoro-4-sulfamoylbenzyl)-1H-pyrazol-1-yl) thiazole-4-carboxylic acid, 2-(5-(cyclopropylmethyl)-3-(4-fluoro-3-(1H-imidazol-2-yl) phenyl)-4-(3-fluoro-4-sulfamoylbenzyl)-1H-pyrazol-1-yl)thiazole-4-carboxylic acid, 2-(3-(3-(1H-benzo[d] imidazol-2-yl)-4-fluorophenyl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(4-fluoro-3-(2-methyl-1H-imidazol-5-yl) phenyl)-4-(3-fluoro-4-sulfamoylbenzyl)-1H-pyrazol-1-yl)thiazole-4-carboxylic acid, 2-(5-(cyclopropylmethyl)-3-(4-fluoro-3-((5-methylthiophen-2-yl) ethynyl) phenyl)-4-(3-fluoro-4-sulfamoylbenzyl)-1H-pyrazol-1-yl)thiazole-4-carboxamide, 2-(3-(4'-chloro-3'-fluoro-[1,r-biphenyl]-3-yl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-4-(3-fluoro-4-sulfamoylbenzyl)-3-(4'-methoxy-3 '-methyl-[1,1'-biphenyl]-3-yl)-1H-pyrazol-1-yl)thiazole-4-carboxylic acid, 2-(3-(4'-chloro-[1,1'-biphenyl]-3-yl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(3'-fluoro-4'-methyl-[1,l'-biphenyl]-3-yl)-4-(3-fluoro-4-sulfamoylbenzyl)-1H-pyrazol-1-yl)thiazole-4-carboxylic acid, 2-(3-(4'-(tert-butyl)-[1,1'-biphenyl]-3-yl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-4-(3-fluoro-4-sulfamoylbenzyl)-3-(4'-isopropyl-[11,1'-biphenyl]-3-yl)-1H-pyrazol-1-yl)thiazole-4-carboxylic acid, 2-(3-(3'-chloro-4'-methoxy-[1,l'-biphenyl]-3-yl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-4-(3-fluoro-4-sulfamoylbenzyl)-3-(3 '-isopropyl-[1,1'-biphenyl]-3-yl)-1H-pyrazol-1-yl)thiazole-4-carboxylic acid, 2-(5-(cyclopropylmethyl)-4-(3-fluoro-4-sulfamoylbenzyl)-3-(3-(5,6,7,8-tetrahydronaphthalen-2-yl) phenyl)-1H-pyrazol-1-yl)thiazole-4-carboxylic acid, 2-(3-(3'-chloro-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(3-(4'-cyano-[1, l'-biphenyl]-3-yl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(3',5-difluoro-[1,1'-biphenyl]-3-yl)-4-(3-fluoro-4-sulfamoylbenzyl)-1H-pyrazol-1-yl)thiazole-4-carboxylic acid, 2-(5-(cyclopropylmethyl)-3-(4'-(dimethylamino)-[1,1'-biphenyl]-3-yl)-4-(3-fluoro-4-sulfamoylbenzyl)-1H-pyrazol-1-yl)thiazole-4-carboxylic acid, 2-(5-(cyclopropylmethyl)-3-(3'-ethyl-4'-methoxy-[1,l'-biphenyl]-3-yl)-4-(3-fluoro-4-sulfamoylbenzyl)-1H-pyrazol-1-yl)thiazole-4-carboxylic acid, 2-(3-(4'-cyclopropyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid, 2-(3-(4'-cyclobutyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid, 2-(3-(4'-chloro-6-fluoro-3'-methyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(3'-ethyl-6-fluoro-4'-methoxy-[1,l'-biphenyl]-3-yl)-4-(3-fluoro-4-sulfamoylbenzyl)-1H-pyrazol-1-yl)thiazole-4-carboxylic acid, 2-(5-(cyclopropylmethyl)-4-(3-fluoro-4-sulfamoylbenzyl)-3-(4-(2,2,2-trifluoroethyl)-[1, 1'-biphenyl]-3-yl)-1H-pyrazol-1-yl)thiazole-4-carboxylic acid, 2-(3-(3-(tert-butylcarbamoyl) phenyl)-5-(cyclopropylmethyl)-4-(4-sulfamoylbenzyl)-1H-pyrazol-1-yl)thiazole-4-carboxylic acid, 2-(3-(3-(1H-benzo[d] imidazol-2-yl) phenyl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(4'-(dimethylamino)-6-fluoro-[1,1'-biphenyl]-3-yl)-4-(3-fluoro-4-sulfamoylbenzyl)-1H-pyrazol-1-yl)thiazole-4-carboxylic acid, 2-(3-(3'-chloro-6-fluoro-4'-methoxy-[1,l'-biphenyl]-3-yl)-5-(cyclopropylmethyl)-4-(3-fluoro-4-sulfamoylbenzyl)-1H-pyrazol-1-yl)thiazole-4-carboxylic acid, 2-(3-(3'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid, 2-(3-(4'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(3'-(dimethylamino)-6-fluoro-[1,1'-biphenyl]-3-yl)-4-(3-fluoro-4-sulfamoylbenzyl)-1H-pyrazol-1-yl)thiazole-4-carboxylic acid, 2-(5-(cyclopropylmethyl)-3-(4', 6-difluoro-3'-methyl-[1, l'-biphenyl]-3-yl)-4-(3-fluoro-4-sulfamoylbenzyl)-1H-pyrazol-1-yl)thiazole-4-carboxylic acid, 2-(5-(cyclopropylmethyl)-3-(3',6-difluoro-[1,1'-biphenyl]-3-yl)-4-(3-fluoro-4-sulfamoylbenzyl)-1H-pyrazol-1-yl)thiazole-4-carboxylic acid, 2-(5-(cyclopropylmethyl)-3-(3-(4,5-dihydrofuran-2-yl)-4-fluorophenyl)-4-(3-fluoro-4-sulfamoylbenzyl)-1H-pyrazol-1-yl)thiazole-4-carboxylic acid, 2-(5-(cyclopropylmethyl)-4-(3-fluoro-4-sulfamoylbenzyl)-3-(4'-methyl-[1,1'-biphenyl]-3-yl)-1H-pyrazol-1-yl)thiazole-4-carboxylic acid, 2-(5-(cyclopropylmethyl)-3-(6-fluoro-3'-isopropyl-[1, l'-biphenyl]-3-yl)-4-(3-fluoro-4-sulfamoylbenzyl)-1H-pyrazol-1-yl)thiazole-4-carboxylic acid, 2-(3-(3'-cyano-6-fluoro-[1,l'-biphenyl]-3-yl)-5-(cyclopropylmethyl)-4-(3-fluoro-4-sulfamoylbenzyl)-1H-pyrazol-1-yl)thiazole-4-carboxylic acid, 2-(3-(4'-cyano-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid, 2-(5-(cyclopropylmethyl)-3-(4-fluoro-3-(2-oxopyrrolidin-1-yl) phenyl)-4-(3-fluoro-4-sulfamoylbenzyl)-1H-pyrazol-1-yl)thiazole-4-carboxylic acid, 2-(5-(cyclopropylmethyl)-4-(3-fluoro-4-sulfamoylbenzyl)-3-(3-(5-methylpyridin-2-yl) phenyl)-1H-pyrazol-1-yl)thiazole-4-carboxylic acid, 2-(5-(cyclopropylmethyl)-4-(3-fluoro-4-sulfamoylbenzyl)-3-(3-(6-methylpyridin-3-yl) phenyl)-1H-pyrazol-1-yl)thiazole-4-carboxylic acid, 2-(5-(2-cyclopropylethyl)-4-(3-fluoro-4-sulfamoylbenzyl)-3-(4'-(perfluoroethyl)-[1,1'-biphenyl]-3-yl)-1H-pyrazol-1-yl)thiazole-4-carboxylic acid, 2-(5-(2-cyclopropylethyl)-4-(3-fluoro-4-sulfamoylbenzyl)-3-(4'-isopropyl-[1,1'-biphenyl]-3-yl)-1H-pyrazol-1-yl)thiazole-4-carboxylic acid,
2-(5-(2-cyclopropylethyl)-4-(3-fluoro-4-sulfamoylbenzyl)-3-(4'-isobutyl-[1, l'-biphenyl]-3-yl)-1H-pyrazol-1-yl)thiazole-4-carboxylic acid,
2-(5-(cyclopropylmethyl)-4-(3-fluoro-4-sulfamoylbenzyl)-3-(4'-(5-methylthiophen-2-yl)-[1,1'-biphenyl]-3-yl)-1H-pyrazol-1-yl)thiazole-4-carboxylic acid,
2-(5-(cyclopropylmethyl)-3-(6-fluoro-4'-(5-methylthiophen-2-yl)-[1,1'-biphenyl]-3-yl)-4-(3-fluoro-4-sulfamoylbenzyl)-1H-pyrazol-1-yl)thiazole-4-carboxylic acid,
2-[5-(cyclopropylmethyl)-4-[(3-fluoro-4-sulfamoylphenyl) methyl]-3-[5-(4-isopropylphenyl) pyridin-3-yl] pyrazol-1-yl]-1,3-thiazole-4-carboxylic acid,
2-[5-(cyclopropylmethyl)-4-[(3-fluoro-4-sulfamoylphenyl) methyl]-3-[6-(4-isopropylphenyl)pyridin-2-yl] pyrazol-1-yl]-1,3-thiazole-4-carboxylic acid,
2-{3-[3-(4-cyclopropyl-3-fluorophenyl)-4-fluorophenyl]-5-(cyclopropylnethyl)-4-[(3-fluoro-4-sulfamoylphenyl)methyl] pyrazol-1-yl}-1,3-thiazole-4-carboxylic acid,
2-[5-(cyclopropylmethyl)-3-[4-fluoro-3-(4-isopropyl-3-methylphenyl)phenyl]-4-[(3-fluoro-4-sulfamoylphenyl)methyl] pyrazol-1-yl]-1,3-thiazole-4-carboxylic acid,
2-[5-(cyclopropylmethyl)-4-[(3-fluoro-4-sulfamoylphenyl) methyl]-3-[3-(2-methylpyrimidin-5-yl) phenyl] pyrazol-1-yl]-1,3-thiazole-4-carboxylic acid,
2-[5-(cyclopropylmethyl)-4-[(3-fluoro-4-sulfamoylphenyl) methyl]-3-[3-(5-isopropyl-1,3-thiazol-2-yl)phenyl] pyrazol-1-yl]-1,3-thiazole-4-carboxylic acid,
2-[5-(cyclopropylmethyl)-4-[(3-fluoro-4-sulfamoylphenyl) methyl]-3-[3-(5-isopropylpyrimidin-2-yl)phenyl] pyrazol-1-yl]-1,3-thiazole-4-carboxylic acid,
2-[5-(cyclopropylmethyl)-4-[(3-fluoro-4-sulfamoylphenyl) methyl]-3-[3-(5-methylpyrimidin-2-yl)phenyl] pyrazol-1-yl]-1,3-thiazole-4-carboxylicacid,
2-[5-(cyclopropylmethyl)-4-[(3-fluoro-4-sulfamoylphenyl) methyl]-3-[3-(5-isopropylpyridin-2-yl)phenyl] pyrazol-1-yl]-1,3-thiazole-4-carboxylicacid,
2-(5-(cyclopropylmethyl)-4-(3-fluoro-4-sulfamoylbenzyl)-3-(4'-(trifluoromethyl)-[1,1'-biphenyl]-3-yl)-1H-pyrazol-1-yl)thiazole-4-carboxylic acid,
2-(5-(cyclopropylmethyl)-3-(3-(2,3-dihydro-1H-inden-5-yl) phenyl)-4-(3-fluoro-4-sulfamoylbenzyl)-1H-pyrazol-1-yl)thiazole-4-carboxylic acid,
2-(3-(3-(1H-benzo[d] imidazol-2-yl) phenyl)-5-(cyclopropylmethyl)-4-(3-fluoro-4-sulfamoylbenzyl)-1H-pyrazol-1-yl)thiazole-4-carboxylic acid,
2-(3-(4'-cyclopropyl-[1,r-biphenyl]-3-yl)-5-(cyclopropylmethyl)-4-(3-fluoro-4-sulfamoylbenzyl)-1H-pyrazol-1-yl)thiazole-4-carboxylic acid,
2-(5-(cyclopropylmethyl)-3-(3'-ethyl-6-fluoro-4'-methoxy-[1,l'-biphenyl]-3-yl)-4-(3-fluoro-4-sulfamoylbenzyl)-1H-pyrazol-1-yl)thiazole-4-carboxylic acid,
2-(5-(cyclopropylmethyl)-4-(3-fluoro-4-sulfamoylbenzyl)-3-(4'-(perfluoroethyl)-[1,1'-biphenyl]-3-yl)-1H-pyrazol-1-yl)thiazole-4-carboxylic acid,
2-(5-(cyclopropylmethyl)-3-(6-fluoro-4'-(perfluoroethyl)-[1,1'-biphenyl]-3-yl)-4-(3-fluoro-4-sulfamoylbenzyl)-1H-pyrazol-1-yl)thiazole-4-carboxylic acid,
2-(5-(cyclopropylmethyl)-4-(3-fluoro-4-sulfamoylbenzyl)-3-(4'-isobutyl-[1,l'-biphenyl]-3-yl)-1H-pyrazol-1-yl)thiazole-4-carboxylic acid,
2-(5-(cyclopropylmethyl)-3-(6-fluoro-4'-isobutyl-[1,1'-biphenyl]-3-yl)-4-(3-fluoro-4-sulfamoylbenzyl)-1H-pyrazol-1-yl)thiazole-4-carboxylic acid),
2-(5-(cyclopropylmethyl)-4-(3-fluoro-4-sulfamoylbenzyl)-3-(4'-hydroxy-3 '-methyl-[1,1'-biphenyl]-3-yl)-1H-pyrazol-1-yl)thiazole-4-carboxylic acid,
2-(5-(cyclopropylmethyl)-3-(3'-fluoro-4'-hydroxy-[1,1'-biphenyl]-3-yl)-4-(3-fluoro-4-sulfamoylbenzyl)-1H-pyrazol-1-yl)thiazole-4-carboxylic acid,
2-(5-(cyclopropylmethyl)-3-(3'-fluoro-4'-isopropyl-[1,1'-biphenyl]-3-yl)-4-(3-fluoro-4-sulfamoylbenzyl)-1H-pyrazol-1-yl)thiazole-4-carboxylic acid,
2-(5-(cyclopropylmethyl)-4-(3-fluoro-4-sulfamoylbenzyl)-3-(6-((5-methylthiophen-2-yl) ethynyl) pyridin-2-yl)-1H-pyrazol-1-yl)thiazole-4-carboxylic acid,
2-(5-(2-cyclopropylethyl)-4-(3-fluoro-4-sulfamoylbenzyl)-3-(3-((5-methylfuran-2-yl) ethynyl) phenyl)-1H-pyrazol-1-yl)thiazole-4-carboxylic acid,
2-(5-(cyclopropylmethyl)-4-(3-fluoro-4-sulfamoylbenzyl)-3-((5-methylthiophen-2-yl) ethynyl) thiophen-2-yl)-1H-pyrazol-1-yl)thiazole-4-carboxylic acid,
2-(5-(2-cyclopropylethyl)-4-(3-fluoro-4-sulfamoylbenzyl)-3-(3-((5-methylthiazol-2-yl) ethynyl) phenyl)-1H-pyrazol-1-yl)thiazole-4-carboxylic acid,
2-(5-(2-cyclopropylethyl)-4-(3-fluoro-4-sulfamoylbenzyl)-3-(3-((2-methylthiazol-5-yl) ethynyl) phenyl)-1H-pyrazol-1-yl)thiazole-4-carboxylic acid,
2-(5-(cyclopropylmethyl)-4-(3-fluoro-4-sulfamoylbenzyl)-3-(3-((2-methylthiazol-4-yl) ethynyl) phenyl)-1H-pyrazol-1-yl)thiazole-4-carboxylic acid,
2-(5-(cyclopropylmethyl)-4-(3-fluoro-4-sulfamoylbenzyl)-3-(4-((5-methylthiophen-2-yl) ethynyl) thiophen-2-yl)-1H-pyrazol-1-yl)thiazole-4-carboxylic acid,
2-(5-(2-cyclopropylethyl)-3-(3-((2,5-dimethylthiophen-3-yl) ethynyl) phenyl)-4-(3-fluoro-4-sulfamoylbenzyl)-1H-pyrazol-1-yl)thiazole-4-carboxylic acid,
2-(5-(2-cyclopropylethyl)-4-(3-fluoro-4-sulfamoylbenzyl)-3-(3-((5-methylthiophen-3-yl) ethynyl) phenyl)-1H-pyrazol-1-yl)thiazole-4-carboxylic acid,
2-(5-(cyclopropylmethyl)-4-(3-fluoro-4-sulfamoylbenzyl)-3-(3-((5-methylthiophen-3-yl) ethynyl) phenyl)-1H-pyrazol-1-yl)thiazole-4-carboxylic acid,
2-(5-(cyclopropylmethyl)-3-(3-((2,5-dimethylthiophen-3-yl) ethynyl) phenyl)-4-(3-fluoro-4-sulfamoylbenzyl)-1H-pyrazol-1-yl)thiazole-4-carboxylic acid,
2-(5-(cyclopropylmethyl)-4-(3-fluoro-4-sulfamoylbenzyl)-3-(3-(2-(5-methylthiophen-2-yl)-2-oxoethyl) phenyl)-1H-pyrazol-1-yl)thiazole-4-carboxylic acid,
2-(5-(2-cyclopropylethyl)-4-(3-fluoro-4-sulfamoylbenzyl)-3-(3-((2-methylthiazol-4-yl) ethynyl) phenyl)-1H-pyrazol-1-yl)thiazole-4-carboxylic acid,
2-(5-(2-cyclopropylethyl)-3-(3-((5-cyclopropylthiophen-2-yl) ethynyl) phenyl)-4-(3-fluoro-4-sulfamoylbenzyl)-1H-pyrazol-1-yl)thiazole-4-carboxylic acid,
2-(3-(3-((5-cyclobutylthiophen-2-yl) ethynyl) phenyl)-5-(cyclopropylmethyl)-4-(3-fluoro-4-sulfamoylbenzyl)-1H-pyrazol-1-yl)thiazole-4-carboxylic acid,
2-(3-(3-((5-cyclobutylthiophen-2-yl) ethynyl) phenyl)-5-(2-cyclopropylethyl)-4-(3-fluoro-4-sulfamoylbenzyl)-1H-pyrazol-1-yl)thiazole-4-carboxylic acid,
2-(5-(cyclopropylmethyl)-4-(3-fluoro-4-sulfamoylbenzyl)-3-(3-((5-methylthiophen-2-yl)ethynyl)phenyl)-1H-pyrazol-1-yl)oxazole-4-carboxylic acid,
2-(5-(3-cyclopropylpropyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 2-(5-(cyclopropylmethyl)-3-(4-fluoro-3-((5-methylthiophen-2-yl)ethynyl)phenyl)-4-(3-fluoro-4-sulfamoylbenzyl)-1H-pyrazol-1-yl)thiazole-4-carboxylic acid, 2-(5-(cyclopropylmethyl)-3-(6-fluoro-4'-methyl-[1,1'-biphenyl]-3-yl)-4-(4-sulfamoylbenzyl)-1H-pyrazol-1-yl) thiazole-4-carboxylic acid, 2-(5-(cyclopropylmethyl)-4-(2-fluoro-4-sulfamoylbenzyl)-3-(4'-methyl-[1,1'-biphenyl]-3-yl)-1H-pyrazol-1-yl)thiazole-4-carboxylic acid, 2-(3-(3-(cyclopentylethynyl)-4-fluorophenyl)-5-(cyclopropylmethyl)-4-(3-fluoro-4-sulfamoylbenzyl)-1H-pyrazol-1-yl)thiazole-4-carboxylic acid, or a pharmaceutically acceptable salt of any of the foregoing.

2. The method of claim 1, wherein the therapeutically effective amount of the compound of Formula I, or a pharmaceutically acceptable salt thereof, is an amount sufficient to reduce the concentration of oxalate in the patient's urine or blood compared to the level of oxalate in the patient's urine or blood prior to administration of the compound of Formula I, or a pharmaceutically acceptable salt thereof.

3. The method of any of claim 1, wherein the therapeutically effective amount of the compound of Formula I, or a pharmaceutically acceptable salt thereof, is an amount sufficient to reduce LDH activity in the patient's liver compared to the level of LDH activity in the patient's liver prior to administration of the compound of Formula I, or a pharmaceutically acceptable salt thereof.

4. The method of claim 1, wherein the therapeutically effective amount of the compound of Formula I, or a pharmaceutically acceptable salt thereof, is an amount sufficient to decrease the mean size of kidney stones in the patient's kidneys compared to the mean size of kidney stones in the patient's kidneys prior to administration of the compound of Formula I, or a pharmaceutically acceptable salt thereof.

5. The method of claim 1, wherein the therapeutically effective amount of the compound of Formula I, or a pharmaceutically acceptable salt thereof, is an amount sufficient to decrease the total number of kidney stones in the patient's kidneys compared to the total number of kidney stones in the patient's kidneys prior to administration of the compound of Formula I, or a pharmaceutically acceptable salt thereof.

6. The method of claim 1, wherein the disease or disorder associated with elevated oxalate levels is primary hyperoxaluria, idiopathic hyperoxaluria, kidney stone disease, chronic kidney disease (CKD), or end stage renal disease (ESRD).

7. The method of claim 1, wherein the primary hyperoxaluria is primary hyperoxaluria type 1 (PH type 1), primary hyperoxaluria type 2 (PH type 2), or primary hyperoxaluria type 3 (PH type 3).

8. The method claim 1, wherein the patient has a mutation in AGXT, GPHPR, HOGA1, or a combination of any of the foregoing.

9. The method of claim 1, wherein the compound of Formula I, or a pharmaceutically acceptable salt thereof, is administered as a monotherapy.

10. The method of claim 1, wherein the compound of Formula I, or a pharmaceutically acceptable salt thereof, is administered to the patient in combination with at least one additional active agent.

11. The method of claim 10, wherein the at least one additional active agent is selected from Vitamin B-6, phosphate, citrate, stiripentol (DIACOMIT), freeze-dried live Oxalobacter formigenes (OXABACT), reloxaliase (ALLN-177), and RNAi.

12. A method of treating primary hyperoxaluria comprising, administering to the patient a therapeutically effective amount of a compound of Formula I or a pharmaceutically acceptable salt thereof, wherein the compound of Formula (I) is 2-(5-(cyclopropylmethyl)-3-(6-fluoro-4'-methyl-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-4'-(trifluoromethyl)-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-2'-methyl-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-4'-methoxy-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(4-fluoro-3-(1H-inden-2-yl)phenyl)-4-(3-fluoro-4-sulfamoylbenzyl)-1H-pyrazol-1-yl) thiazole-4-carboxylic acid, 2-(5-(cyclopropylmethyl)-3-(6-fluoro-4',4'-dimethyl-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4',4',6-trifluoro-2',3',4',5'-tetrahydro-[1,1'-biphenyl]-3-yl)-1H-pyrazol-1-yl) thiazole-4-carboxylic acid, 2-(5-(cyclopropylmethyl)-3-(4-fluoro-3-(spiro[2.5]oct-5-en-6-yl) phenyl)-4-(3-fluoro-4-sulfamoylbenzyl)-1H-pyrazol-1-yl) thiazole-4-carboxylic acid, 2-(3-(3-(but-1-yn-1-yl)-4-fluorophenyl)-5-(cyclopropylmethyl)-4-(3-fluoro-4-sulfamoylbenzyl)-1H-pyrazol-1-yl) thiazole-4-carboxylic acid, 2-(3-(3-((5-(tert-butyl) thiophen-2-yl) ethynyl)-4-fluorophenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(4-fluoro-3-((2-methylthiazol-5-yl) ethynyl) phenyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(2-cyclopropylethyl)-3-(4-fluoro-3-((5-methylthiophen-2-yl) ethynyl) phenyl)-4-(3-fluoro-4-sulfamoylbenzyl)-1H-pyrazol-1-yl) thiazole-4-carboxylic acid, 2-(5-(cyclopropylmethyl)-3-(4-fluoro-3-((5-methylthiazol-2-yl) ethynyl) phenyl)-4-(3-fluoro-4-sulfamoylbenzyl)-1H-pyrazol-1-yl) thiazole-4-carboxylic acid, 2-(5-(2-cyclopropylethyl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(1-cyclopropylethyl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(cyclopropylmethyl)-3-(3-((5-cyclopropylthiophen-2-yl) ethynyl) phenyl)-4-(3-fluoro-4-sulfamoylbenzyl)-1H-pyrazol-1-yl) thiazole-4-carboxylic acid, 2-(3-(3-((5-chlorothiophen-2-yl) ethynyl) phenyl)-5-(cyclopropylmethyl)-4-(3-fluoro-4-sulfamoylbenzyl)-1H-pyrazol-1-yl) thiazole-4-carboxylic, (E)-2-(5-(cyclopropylmethyl)-4-(3-fluoro-4-sulfamoylbenzyl)-3-(3-(2-(5-methylthiophen-2-yl) vinyl) phenyl)-1H-pyrazol-1-yl) thiazole-4-carboxylic acid, 2-(5-(cyclopropylmethyl)-4-(3-fluoro-4-sulfamoylbenzyl)-3-(3-((3-methylthiophen-2-yl) ethynyl) phenyl)-1H-pyrazol-1-yl) thiazole-4-carboxylic acid, 2-(5-(cyclopropylmethyl)-3-(3-((5-(difluoromethyl) thiophen-2-yl) ethynyl) phenyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3-((5-methyloxazol-2-yl) ethynyl) phenyl)-1H-pyrazol-1-yl) thiazole-4-carboxylic acid, 2-(4-(3-fluoro-4-sulfamoylbenzyl)-5-((1-methylcyclopropyl) methyl)-3-(3-((5-methylthiophen-2-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3-((5-(trifluoromethyl) thiophen-2-yl) ethynyl) phenyl)-1H-pyrazol-1-yl) thiazole-4-carboxylic acid, 2-(5-(cyclopropylmethyl)-3-(3-((3,5-dimethylthiophen-2-yl) ethynyl) phenyl)-4-(3-fluoro-4-sulfamoylbenzyl)-1H-pyrazol-1-yl) thiazole-4-carboxylic, 2-(5-(cyclopropylmethyl)-4-(3-fluoro-4-sulfamoylbenzyl)-3-(3-((5-isopropylthiophen-2-yl) ethynyl) phenyl)-1H-pyrazol-1-yl) thiazole-4-carboxylic acid, 2-(5-(2-cyclopropylpropan-2-yl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3-((5-methylfuran-2-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3-(2-(5-methylthiophen-2-yl) cyclopropyl) phenyl)-1H-pyrazol-1-yl) thiazole-4-carboxylic acid, 2-(4-(3-fluoro-4-sulfamoylbenzyl)-3-(3-((5-methylthiophen-2-yl) ethynyl) phenyl)-5-(spiro[2.2] pentan-1-yl)-1H-pyrazol-1-yl) thiazole-4-carboxylic acid, 2-(5-(cyclopropylmethyl)-4-(3-fluoro-4-sulfamoylbenzyl)-3-(3-((cis)-3-(5-methylthiophen-2-yl) cyclobutyl) phenyl)-1H-pyrazol-1-yl) thiazole-4-carboxylic acid, 2-(5-(cyclopropylmethyl)-4-(3-fluoro-4-sulfamoylbenzyl)-3-(3-(3-(5-methylthiophen-2-yl) cyclobutyl) phenyl)-1H-pyrazol-1-yl) thiazole-4-carboxylic acid, 2-(5-([1, 1'-bi (cyclopropan)]-2-yl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3',4',6-trifluoro-[1,1'-biphenyl]-3-yl)-1H-pyrazol-1-yl) thiazole-4-carboxylic acid, 2-(5-(cyclopropylmethyl)-3-(3',6-difluoro-4'-methyl-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-4'-(trifluoromethyl)-[1,1'-biphenyl]-3-yl)-4-(3-fluoro-4-sulfamoylbenzyl)-1H-pyrazol-1-yl) thiazole-4-carboxylic acid, 2-(3-(4-chloro-6-fluoro-[1, 1'-biphenyl]-3-yl)-5-(cyclopropylmethyl)-4-(3-fluoro-4-sulfamoylbenzyl)-1H-pyrazol-1-yl) thiazole-4-carboxylic acid, 2-(3-(3-acetyl-4-fluorophenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(6-fluoro-3'-methyl-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-4'-isopropyl-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(4-fluoro-3-(5,6,7,8-tetrahydronaphthalen-2-yl) phenyl)-4-(3-fluoro-4-sulfamoylbenzyl)-1H-pyrazol-1-yl) thiazole-4-carboxylic acid, 2-(3-(4'-chloro-3',6-difluoro-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(3-(pyrrolidine-1-carbonyl) phenyl)-4-(4-sulfamoylbenzyl)-1H-pyrazol-1-yl) thiazole-4-carboxylic acid, 2-(5-(cyclopropylmethyl)-3-(6-fluoro-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(3-(3-(tert-butylcarbamoyl)-4-fluorophenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(3-(4,5-dihydrofuran-2-yl)-4-fluorophenyl)-4-(3-fluoro-4-sulfamoylbenzyl)-1H-pyrazol-1-yl) thiazole-4-carboxylic acid, 2-(3-(3'-chloro-6-fluoro-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(6-fluoro-4'-methoxy-3'-methyl-[1, 1'-biphenyl]-3-yl)-4-(3-fluoro-4-sulfamoylbenzyl)-1H-pyrazol-1-yl) thiazole-4-carboxylic, 2-(5-(cyclopropylmethyl)-3-(6-fluoro-3',5'-dimethyl-[1, 1'-biphenyl]-3-yl)-4-(3-fluoro-4-sulfamoylbenzyl)-1H-pyrazol-1-yl) thiazole-4-carboxylic acid, 2-(3-(3-benzamido-4-fluorophenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(6-fluoro-3',5'-dimethoxy-[1, 1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(4-fluoro-3-(2-oxopyrrolidin-1-yl) phenyl)-4-(3-fluoro-4-sulfamoylbenzyl)-1H-pyrazol-1-yl) thiazole-4-carboxylic acid, 2-(5-(cyclopropylmethyl)-3-(3-(2,3-dihydro-1H-inden-5-yl)-4-fluorophenyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3',5',6-trifluoro-[1,1'-biphenyl]-3-yl)-1H-pyrazol-1-yl) thiazole-4-carboxylic acid, 2-(5-(cyclopropylmethyl)-3-(3',5'-dichloro-6-fluoro-[1, 1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(4-fluoro-3-(6-isopropyl-2, 6-diazaspiro[3.3] heptan-2-yl) phenyl)-4-(3-fluoro-4-sulfamoylbenzyl)-1H-pyrazol-1-yl) thiazole-4-carboxylic acid, 2-(5-(cyclopropylmethyl)-3-(4-fluoro-3-(1H-imidazol-2-yl) phenyl)-4-(3-fluoro-4-sulfamoylbenzyl)-1H-pyrazol-1-yl) thiazole-4-carboxylic acid, 2-(3-(3-(1H-benzo[d] imidazol-2-yl)-4-fluorophenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(4-fluoro-3-(2-methyl-1H-imidazol-5-yl) phenyl)-4-(3-fluoro-4-sulfamoylbenzyl)-1H-pyrazol-1-yl) thiazole-4-carboxylic acid, 2-(5-(cyclopropylmethyl)-3-(4-fluoro-3-((5-methylthiophen-2-yl) ethynyl) phenyl)-4-(3-fluoro-4-sulfamoylbenzyl)-1H-pyrazol-1-yl) thiazole-4-carboxamide, 2-(3-(4'-chloro-3'-fluoro-[1,r-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4'-methoxy-3 '-methyl-[1,1'-biphenyl]-3-yl)-1H-pyrazol-1-yl) thiazole-4-carboxylic acid,
2-(3-(4'-chloro-[1,1'-biphenyl]-3-yl)-5-(cyclopropylmethyl)-4-(3-fluoro-4-sulfamoylbenzyl)-1H-pyrazol-1-yl) thiazole-4-carboxylic acid,
2-(5-(cyclopropylmethyl)-3-(3'-fluoro-4'-methyl-[1,1'-biphenyl]-3-yl)-4-(3-fluoro-4-sulfamoylbenzyl)-1H-pyrazol-1-yl) thiazole-4-carboxylic acid,
2-(3-(4'-(tert-butyl)-[1,1'-biphenyl]-3-yl)-5-(cyclopropylmethyl)-4-(3-fluoro-4-sulfamoylbenzyl)-1H-pyrazol-1-yl) thiazole-4-carboxylic acid,
2-(5-(cyclopropylmethyl)-4-(3-fluoro-4-sulfamoylbenzyl)-3-(4'-isopropyl-[11,1'-biphenyl]-3-yl)-1H-pyrazol-1-yl) thiazole-4-carboxylic acid,
2-(3-(3'-chloro-4'-methoxy-[1,l'-biphenyl]-3-yl)-5-(cyclopropylmethyl)-4-(3-fluoro-4-sulfamoylbenzyl)-1H-pyrazol-1-yl) thiazole-4-carboxylic acid,
2-(5-(cyclopropylmethyl)-4-(3-fluoro-4-sulfamoylbenzyl)-3-(3 '-isopropyl-[1,1'-biphenyl]-3-yl)-1H-pyrazol-1-yl) thiazole-4-carboxylic acid,
2-(5-(cyclopropylmethyl)-4-(3-fluoro-4-sulfamoylbenzyl)-3-(3-(5,6,7,8-tetrahydronaphthalen-2-yl) phenyl)-1H-pyrazol-1-yl) thiazole-4-carboxylic acid,
2-(3-(3'-chloro-[1,1'-biphenyl]-3-yl)-5-(cyclopropylmethyl)-4-(3-fluoro-4-sulfamoylbenzyl)-1H-pyrazol-1-yl) thiazole-4-carboxylic acid,
2-(3-(4'-cyano-[1,1'-biphenyl]-3-yl)-5-(cyclopropylmethyl)-4-(3-fluoro-4-sulfamoylbenzyl)-1H-pyrazol-1-yl) thiazole-4-carboxylic acid,
2-(5-(cyclopropylmethyl)-3-(3',5-difluoro-[1,1'-biphenyl]-3-yl)-4-(3-fluoro-4-sulfamoylbenzyl)-1H-pyrazol-1-yl) thiazole4-carboxylic acid,
2-(5-(cyclopropylmethyl)-3-(4'-(dimethylamino)-[1,1'-biphenyl]-3-yl)-4-(3-fluoro-4-sulfamoylbenzyl)-1H-pyrazol-1-yl) thiazole-4-carboxylic acid,
2-(5-(cyclopropylmethyl)-3-(3'-ethyl-4'-methoxy-[1,1'-biphenyl]-3-yl)-4-(3-fluoro-4-sulfamoylbenzyl)-1H-pyrazol-1-yl) thiazole-4-carboxylic acid,
2-(3-(4'-cyclopropyl-[1,1'-biphenyl]-3-yl)-5-(cyclopropylmethyl)-4-(3-fluoro-4-sulfamoylbenzyl)-1H-pyrazol-1-yl) thiazole-4-carboxylic acid,
2-(3-(4'-cyclobutyl-[1,1'-biphenyl]-3-yl)-5-(cyclopropylmethyl)-4-(3-fluoro-4-sulfamoylbenzyl)-1H-pyrazol-1-yl) thiazole-4-carboxylic acid,
2-(3-(4'-chloro-6-fluoro-3'-methyl-[1,1'-biphenyl]-3-yl)-5-(cyclopropylmethyl)-4-(3-fluoro-4-sulfamoylbenzyl)-1H-pyrazol-1-yl) thiazole-4-carboxylic acid,
2-(5-(cyclopropylmethyl)-3-(3'-ethyl-6-fluoro-4'-methoxy-[1,1'-biphenyl]-3-yl)-4-(3-fluoro-4-sulfamoylbenzyl)-1H-pyrazol-1-yl) thiazole-4-carboxylic acid,
2-(5-(cyclopropylmethyl)-4-(3-fluoro-4-sulfamoylbenzyl)-3-(4-(2,2,2-trifluoroethyl)-[1,1'-biphenyl]-3-yl)-1H-pyrazol-1-yl) thiazole-4-carboxylic acid,
2-(3-(3-(tert-butylcarbamoyl) phenyl)-5-(cyclopropylmethyl)-4-(4-sulfamoylbenzyl)-1H-pyrazol-1-yl) thiazole-4-carboxylic acid,
2-(3-(3-(1H-benzo[d] imidazol-2-yl) phenyl)-5-(cyclopropylmethyl)-4-(3-fluoro-4-sulfamoylbenzyl)-1H-pyrazol-1-yl) thiazole-4-carboxylic acid,
2-(5-(cyclopropylmethyl)-3-(4'-(dimethylamino)-6-fluoro-[1,1'-biphenyl]-3-yl)-4-(3-fluoro-4-sulfamoylbenzyl)-1H-pyrazol-1-yl) thiazole-4-carboxylic acid,
2-(3-(3'-chloro-6-fluoro-4'-methoxy-[1,1'-biphenyl]-3-yl)-5-(cyclopropylmethyl)-4-(3-fluoro-4-sulfamoylbenzyl)-1H-pyrazol-1-yl) thiazole-4-carboxylic acid,
2-(3-(3'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl) thiazole-4-carboxylic acid,
2-(3-(4'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl) thiazole-4-carboxylic acid,
2-(5-(cyclopropylmethyl)-3-(3'-(dimethylamino)-6-fluoro-[1,l'-biphenyl]-3-yl)-4-(3-fluoro-4-sulfamoylbenzyl)-1H-pyrazol-1-yl) thiazole-4-carboxylic acid,
2-(5-(cyclopropylmethyl)-3-(4',6-difluoro-3'-methyl-[1,l'-biphenyl]-3-yl)-4-(3-fluoro-4-sulfamoylbenzyl)-1H-pyrazol-1-yl) thiazole-4-carboxylic acid,
2-(5-(cyclopropylmethyl)-3-(3',6-difluoro-[1,1'-biphenyl]-3-yl)-4-(3-fluoro-4-sulfamoylbenzyl)-1H-pyrazol-1-yl) thiazole-4-carboxylic acid,
2-(5-(cyclopropylmethyl)-3-(3-(4,5-dihydrofuran-2-yl)-4-fluorophenyl)-4-(3-fluoro-4-sulfamoylbenzyl)-1H-pyrazol-1-yl) thiazole-4-carboxylic acid,
2-(5-(cyclopropylmethyl)-4-(3-fluoro-4-sulfamoylbenzyl)-3-(4'-methyl-[1,1'-biphenyl]-3-yl)-1H-pyrazol-1-yl) thiazole-4-carboxylic acid,
2-(5-(cyclopropylmethyl)-3-(6-fluoro-3'-isopropyl-[1,l'-biphenyl]-3-yl)-4-(3-fluoro-4-sulfamoylbenzyl)-1H-pyrazol-1-yl) thiazole-4-carboxylic acid,
2-(3-(3'-cyano-6-fluoro-[1,l'-biphenyl]-3-yl)-5-(cyclopropylmethyl)-4-(3-fluoro-4-sulfamoylbenzyl)-1H-pyrazol-1-yl) thiazole-4-carboxylic acid,
2-(3-(4'-cyano-6-fluoro-[1,1'-biphenyl]-3-yl)-5-(cyclopropylmethyl)-4-(3-fluoro-4-sulfamoylbenzyl)-1H-pyrazol-1-yl) thiazole-4-carboxylic acid,
2-(5-(cyclopropylmethyl)-3-(4-fluoro-3-(2-oxopyrrolidin-1-yl) phenyl)-4-(3-fluoro-4-sulfamoylbenzyl)-1H-pyrazol-1-yl) thiazole-4-carboxylic acid,
2-(5-(cyclopropylmethyl)-4-(3-fluoro-4-sulfamoylbenzyl)-3-(3-(5-methylpyridin-2-yl) phenyl)-1H-pyrazol-1-yl) thiazole-4-carboxylic acid,
2-(5-(cyclopropylmethyl)-4-(3-fluoro-4-sulfamoylbenzyl)-3-(3-(6-methylpyridin-3-yl) phenyl)-1H-pyrazol-1-yl) thiazole-4-carboxylic acid,
2-(5-(2-cyclopropylethyl)-4-(3-fluoro-4-sulfamoylbenzyl)-3-(4'-(perfluoroethyl)-[1,1'-biphenyl]-3-yl)-1H-pyrazol-1-yl) thiazole-4-carboxylic acid,
2-(5-(2-cyclopropylethyl)-4-(3-fluoro-4-sulfamoylbenzyl)-3-(4'-isopropyl-[1,1'-biphenyl]-3-yl)-1H-pyrazol-1-yl) thiazole-4-carboxylic acid,
2-(5-(2-cyclopropylethyl)-4-(3-fluoro-4-sulfamoylbenzyl)-3-(4'-isobutyl-[1,l'-biphenyl]-3-yl)-1H-pyrazol-1-yl) thiazole-4-carboxylic acid,
2-(5-(cyclopropylmethyl)-4-(3-fluoro-4-sulfamoylbenzyl)-3-(4'-(5-methylthiophen-2-yl)-[1,1'-biphenyl]-3-yl)-1H-pyrazol-1-yl) thiazole-4-carboxylic acid,
2-(5-(cyclopropylmethyl)-3-(6-fluoro-4'-(5-methylthiophen-2-yl)-[1,1'-biphenyl]-3-yl)-4-(3-fluoro-4-sulfamoylbenzyl)-1H-pyrazol-1-yl) thiazole-4-carboxylic acid,
2-[5-(cyclopropylmethyl)-4-[(3-fluoro-4-sulfamoylphenyl) methyl]-3-[5-(4-isopropylphenyl) pyridin-3-yl] pyrazol-1-yl]-1,3-thiazole-4-carboxylic acid,
2-[5-(cyclopropylmethyl)-4-[(3-fluoro-4-sulfamoylphenyl) methyl]-3-[6-(4-isopropylphenyl) pyridin-2-yl] pyrazol-1-yl]-1,3-thiazole-4-carboxylic acid,
2-{3-[3-(4-cyclopropyl-3-fluorophenyl)-4-fluorophenyl]-5-(cyclopropyhnethyl)-4-[(3-fluoro-4-sulfamoylphenyl) methyl] pyrazol-1-yl}-1,3-thiazole-4-carboxylic acid, 2-[5-(cyclopropylmethyl)-3-[4-fluoro-3-(4-isopropyl-3-methylphenyl) phenyl]-4-[(3-fluoro-4-sulfamoylphenyl) methyl] pyrazol-1-yl]-1,3-thiazole-4-carboxylic acid, 2-[5-(cyclopropylmethyl)-4-[(3-fluoro-4-sulfamoylphenyl) methyl]-3-[3-(2-methylpyrimidin-5-yl) phenyl] pyrazol-1-yl]-1,3-thiazole-4-carboxylic acid, 2-[5-(cyclopropylmethyl)-4-[(3-fluoro-4-sulfamoylphenyl) methyl]-3-[3-(5-isopropyl-1,3-thiazol-2-yl) phenyl] pyrazol-1-yl]-1,3-thiazole-4-carboxylic acid, 2-[5-(cyclopropylmethyl)-4-[(3-fluoro-4-sulfamoylphenyl) methyl]-3-[3-(5-isopropylpyrimidin-2-yl) phenyl] pyrazol-1-yl]-1,3-thiazole-4-carboxylic acid, 2-[5-(cyclopropylmethyl)-4-[(3-fluoro-4-sulfamoylphenyl) methyl]-3-[3-(5-methylpyrimidin-2-yl) phenyl] pyrazol-1-yl]-1,3-thiazole-4-carboxylicacid, 2-[5-(cyclopropylmethyl)-4-[(3-fluoro-4-sulfamoylphenyl) methyl]-3-[3-(5-isopropylpyridin-2-yl) phenyl] pyrazol-1-yl]-1,3-thiazole-4-carboxylicacid, 2-(5-(cyclopropylmethyl)-4-(3-fluoro-4-sulfamoylbenzyl)-3-(4'-(trifluoromethyl)-[1,1'-biphenyl]-3-yl)-1H-pyrazol-1-yl) thiazole-4-carboxylic acid, 2-(5-(cyclopropylmethyl)-3-(3-(2,3-dihydro-1H-inden-5-yl) phenyl)-4-(3-fluoro-4-sulfamoylbenzyl)-1H-pyrazol-1-yl) thiazole-4-carboxylic acid, 2-(3-(3-(1H-benzo[d] imidazol-2-yl) phenyl)-5-(cyclopropylmethyl)-4-(3-fluoro-4-sulfamoylbenzyl)-1H-pyrazol-1-yl) thiazole-4-carboxylic acid, 2-(3-(4'-cyclopropyl-[1,r-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(3'-ethyl-6-fluoro-4'-methoxy-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4'-(perfluoroethyl)-[1,1'-biphenyl]-3-yl)-1H-pyrazol-1-yl) thiazole-4-carboxylic acid, 2-(5-(cyclopropylmethyl)-3-(6-fluoro-4'-(perfluoroethyl)-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4'-isobutyl-[1,1'-biphenyl]-3-yl)-1H-pyrazol-1-yl) thiazole-4-carboxylic acid, 2-(5-(cyclopropylmethyl)-3-(6-fluoro-4'-isobutyl-[1,1'-biphenyl]-3-yl)-4-(3-fluoro-4-sulfamoylbenzyl)-1H-pyrazol-1-yl) thiazole-4-carboxylic acid), 2-(5-(cyclopropylmethyl)-4-(3-fluoro-4-sulfamoylbenzyl)-3-(4'-hydroxy-3'-methyl-[1,1'-biphenyl]-3-yl)-1H-pyrazol-1-yl) thiazole-4-carboxylic acid, 2-(5-(cyclopropylmethyl)-3-(3'-fluoro-4'-hydroxy-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(3'-fluoro-4'-isopropyl-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(6-((5-methylthiophen-2-yl) ethynyl) pyridin-2-yl)-1H-pyrazol-1-yl) thiazole-4-carboxylic acid, 2-(5-(2-cyclopropylethyl)-4-(3-fluoro-4-sulfamoylbenzyl)-3-(3-((5-methylfuran-2-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(5-((5-methylthiophen-2-yl) ethynyl) thiophen-2-yl)-1H-pyrazol-1-yl) thiazole-4-carboxylic acid, 2-(5-(2-cyclopropylethyl)-4-(3-fluoro-4-sulfamoylbenzyl)-3-(3-((5-methylthiazol-2-yl) ethynyl) phenyl)-1H-pyrazol-1-yl) thiazole-4-carboxylic acid, 2-(5-(2-cyclopropylethyl)-4-(3-fluoro-4-sulfamoylbenzyl)-3-(3-((2-methylthiazol-5-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3-((2-methylthiazol-4-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(4-((5-methylthiophen-2-yl) ethynyl) thiophen-2-yl)-1H-pyrazol-1-yl) thiazole-4-carboxylic acid, 2-(5-(2-cyclopropylethyl)-3-(3-((2,5-dimethylthiophen-3-yl) ethynyl) phenyl)-4-(3-fluoro-4-sulfamoylbenzyl)-1H-pyrazol-1-yl) thiazole-4-carboxylic acid, 2-(5-(2-cyclopropylethyl)-4-(3-fluoro-4-sulfamoylbenzyl)-3-(3-((5-methylthiophen-3-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3-((5-methylthiophen-3-yl) ethynyl) phenyl)-1H-pyrazol-1-yl) thiazole-4-carboxylic acid, 2-(5-(cyclopropylmethyl)-3-(3-((2,5-dimethylthiophen-3-yl) ethynyl) phenyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3-(2-(5-methylthiophen-2-yl)-2-oxoethyl) phenyl)-1H-pyrazol-1-yl) thiazole-4-carboxylic acid, 2-(5-(2-cyclopropylethyl)-4-(3-fluoro-4-sulfamoylbenzyl)-3-(3-((2-methylthiazol-4-yl) ethynyl) phenyl)-1H-pyrazol-1-yl) thiazole-4-carboxylic acid, 2-(5-(2-cyclopropylethyl)-3-(3-((5-cyclopropylthiophen-2-yl) ethynyl) phenyl)-4-(3-fluoro-4-sulfamoylbenzyl)-1H-pyrazol-1-yl) thiazole-4-carboxylic acid, 2-(3-(3-((5-cyclobutylthiophen-2-yl) ethynyl) phenyl)-5-(cyclopropylmethyl)-4-(3-fluoro-4-sulfamoylbenzyl)-1H-pyrazol-1-yl) thiazole-4-carboxylic acid, 2-(3-(3-((5-cyclobutylthiophen-2-yl) ethynyl) phenyl)-5-(2-cyclopropylethyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3-((5-methylthiophen-2-yl) ethynyl) phenyl)-1H-pyrazol-1-yl) oxazole-4-carboxylic acid, 2-(5-(3-cyclopropylpropyl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(cyclopropylmethyl)-3-(4-fluoro-3-((5-methylthiophen-2-yl) ethynyl) phenyl)-4-(3-fluoro-4-sulfamoylbenzyl)-1H-pyrazol-1-yl) thiazole-4-carboxylic acid, 2-(5-(cyclopropylmethyl)-3-(6-fluoro-4'-methyl-[1,1'-biphenyl]-3-yl)-4-(4-sulfamoylbenzyl)-1H-pyrazol-1-yl) thiazole-4-carboxylic acid, 2-(5-(cyclopropylmethyl)-4-(2-fluoro-4-sulfamoylbenzyl)-3-(4'-methyl-[1,1'-biphenyl]-3-yl)-1H-pyrazol-1-yl) thiazole-4-carboxylic acid, 2-(3-(3-(cyclopentylethynyl)-4-fluorophenyl)-5-(cyclopropylmethyl)-4-(3-fluoro-4-sulfamoylbenzyl)-1H-pyrazol-1-yl) thiazole-4-carboxylic acid, or a pharmaceutically acceptable salt of any of the foregoing.

13. The method claim 12, wherein the patient has a mutation in AGXT, GPHPR, HOGA1, or a combination of any of the foregoing.

14. The method of claim 12, wherein the compound of Formula I, or a pharmaceutically acceptable salt thereof, is administered as a monotherapy.

15. The method of claim 12, wherein the compound of Formula I, or a pharmaceutically acceptable salt thereof, is administered to the patient in combination with at least one additional active agent selected from Vitamin B-6, phosphate, citrate, stiripentol (DIACOMIT), freeze-dried live Oxalobacter formigenes (OXABACT), reloxaliase (ALLN-177), and RNAi.

16. A method of decreasing the mean size of kidney stones and/or the total number of kidney stones in the kidney of a patient, the method comprising administering to the patient a therapeutically effective amount of a compound of Formula I, or a pharmaceutically acceptable salt thereof wherein the compound of Formula (I) is 2-(5-(cyclopropylmethyl)-3-(6-fluoro-4'-methyl-2',3',4',5'-tetrahydro-[1, 1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-4'-(trifluoromethyl)-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-2'-methyl-2',3',4',5'-tetrahydro-[1, l'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-4'-methoxy-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(4-fluoro-3-(1H-inden-2-yl) phenyl)-4-(3-fluoro-4-sulfamoylbenzyl)-1H-pyrazol-1-lyl) thiazole-4-carboxylic acid, 2-(5-(cyclopropylmethyl)-3-(6-fluoro-4',4'-dimethyl-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4',4',6-trifluoro-2',3',4',5'-tetrahydro-[1,1'-biphenyl]-3-yl)-1H-pyrazol-1-yl) thiazole-4-carboxylic acid, 2-(5-(cyclopropylmethyl)-3-(4-fluoro-3-(spiro[2.5] oct-5-en-6-yl) phenyl)-4-(3-fluoro-4-sulfamoylbenzyl)-1H-pyrazol-1-yl) thiazole-4-carboxylic acid, 2-(3-(3-(but-1-yn-1-yl)-4-fluorophenyl)-5-(cyclopropylmethyl)-4-(3-fluoro-4-sulfamoylbenzyl)-1H-pyrazol-1-yl) thiazole-4-carboxylic acid, 2-(3-(3-((5-(tert-butyl) thiophen-2-yl) ethynyl)-4-fluorophenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(4-fluoro-3-((2-methylthiazol-5-yl) ethynyl) phenyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(2-cyclopropylethyl)-3-(4-fluoro-3-((5-methylthiophen-2-yl) ethynyl) phenyl)-4-(3-fluoro-4-sulfamoylbenzyl)-1H-pyrazol-1-yl) thiazole-4-carboxylic acid, 2-(5-(cyclopropylmethyl)-3-(4-fluoro-3-((5-methylthiazol-2-yl) ethynyl) phenyl)-4-(3-fluoro-4-sulfamoylbenzyl)-1H-pyrazol-1-yl) thiazole-4-carboxylic acid, 2-(5-(2-cyclopropylethyl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(1-cyclopropylethyl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(cyclopropylmethyl)-3-(3-((5-cyclopropylthiophen-2-yl) ethynyl) phenyl)-4-(3-fluoro-4-sulfamoylbenzyl)-1H-pyrazol-1-yl) thiazole-4-carboxylic acid, 2-(3-(3-((5-chlorothiophen-2-yl) ethynyl) phenyl)-5-(cyclopropylmethyl)-4-(3-fluoro-4-sulfamoylbenzyl)-1H-pyrazol-1-yl) thiazole-4-carboxylic, (E)-2-(5-(cyclopropylmethyl)-4-(3-fluoro-4-sulfamoylbenzyl)-3-(3-(2-(5-methylthiophen-2-yl) vinyl) phenyl)-1H-pyrazol-1-yl) thiazole-4-carboxylic acid, 2-(5-(cyclopropylmethyl)-4-(3-fluoro-4-sulfamoylbenzyl)-3-(3-((3-methylthiophen-2-yl) ethynyl) phenyl)-1H-pyrazol-1-yl) thiazole-4-carboxylic acid, 2-(5-(cyclopropylmethyl)-3-(3-((5-(difluoromethyl) thiophen-2-yl) ethynyl) phenyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3-((5-methyloxazol-2-yl) ethynyl) phenyl)-1H-pyrazol-1-yl) thiazole-4-carboxylic acid, 2-(4-(3-fluoro-4-sulfamoylbenzyl)-5-((1-methylcyclopropyl) methyl)-3-(3-((5-methylthiophen-2-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3-((5-(trifluoromethyl) thiophen-2-yl) ethynyl) phenyl)-1H-pyrazol-1-yl) thiazole-4-carboxylic acid, 2-(5-(cyclopropylmethyl)-3-(3-((3,5-dimethylthiophen-2-yl) ethynyl) phenyl)-4-(3-fluoro-4-sulfamoylbenzyl)-1H-pyrazol-1-yl) thiazole-4-carboxylic, 2-(5-(cyclopropylmethyl)-4-(3-fluoro-4-sulfamoylbenzyl)-3-(3-((5-isopropylthiophen-2-yl) ethynyl) phenyl)-1H-pyrazol-1-yl) thiazole-4-carboxylic acid, 2-(5-(2-cyclopropylpropan-2-yl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3-((5-methylfuran-2-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3-(2-(5-methylthiophen-2-yl) cyclopropyl) phenyl)-1H-pyrazol-1-yl) thiazole-4-carboxylic acid, 2-(4-(3-fluoro-4-sulfamoylbenzyl)-3-(3-((5-methylthiophen-2-yl) ethynyl) phenyl)-5-(spiro[2.2] pentan-1-yl)-1H-pyrazol-1-yl) thiazole-4-carboxylic acid, 2-(5-(cyclopropylmethyl)-4-(3-fluoro-4-sulfamoylbenzyl)-3-(3-((cis)-3-(5-methylthiophen-2-yl) cyclobutyl) phenyl)-1H-pyrazol-1-yl) thiazole-4-carboxylic acid, 2-(5-(cyclopropylmethyl)-4-(3-fluoro-4-sulfamoylbenzyl)-3-(3-(3-(5-methylthiophen-2-yl) cyclobutyl) phenyl)-1H-pyrazol-1-yl) thiazole-4-carboxylic acid, 2-(5-([1, 1'-bi(cyclopropan)]-2-yl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3',4',6-trifluoro-[1,1'-biphenyl]-3-yl)-1H-pyrazol-1-yl) thiazole-4-carboxylic acid, 2-(5-(cyclopropylmethyl)-3-(3',6-difluoro-4'-methyl-[1,l'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-4'-(trifluoromethyl)-[1,1'-biphenyl]-3-yl)-4-(3-fluoro-4-sulfamoylbenzyl)-1H-pyrazol-1-yl) thiazole-4-carboxylic acid, 2-(3-(4-chloro-6-fluoro-[1, 1'-biphenyl]-3-yl)-5-(cyclopropylmethyl)-4-(3-fluoro-4-sulfamoylbenzyl)-1H-pyrazol-1-yl) thiazole-4-carboxylic acid, 2-(3-(3-acetyl-4-fluorophenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(6-fluoro-3'-methyl-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(6-fluoro-4'-isopropyl-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(4-fluoro-3-(5,6,7,8-tetrahydronaphthalen-2-yl) phenyl)-4-(3-fluoro-4-sulfamoylbenzyl)-1H-pyrazol-1-yl) thiazole-4-carboxylic acid, 2-(3-(4'-chloro-3',6-difluoro-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(3-(pyrrolidine-1-carbonyl) phenyl)-4-(4-sulfamoylbenzyl)-1H-pyrazol-1-yl) thiazole-4-carboxylic acid, 2-(5-(cyclopropylmethyl)-3-(6-fluoro-2',3',4',5'-tetrahydro-[1,1'-biphenyl]-3-yl)-4-(3-fluoro-4-sulfamoylbenzyl)-1H-pyrazol-1-yl) thiazole-4-carboxylic acid, 2-(3-(3-(tert-butylcarbamoyl)-4-fluorophenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(3-(4,5-dihydrofuran-2-yl)-4-fluorophenyl)-4-(3-fluoro-4-sulfamoylbenzyl)-1H-pyrazol-1-yl) thiazole-4-carboxylic acid, 2-(3-(3'-chloro-6-fluoro-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(6-fluoro-4'-methoxy-3'-methyl-[1, 1'-biphenyl]-3-yl)-4-(3-fluoro-4-sulfamoylbenzyl)-1H-pyrazol-1-yl) thiazole-4-carboxylic, 2-(5-(cyclopropylmethyl)-3-(6-fluoro-3',5'-dimethyl-[1,1'-biphenyl]-3-yl)-4-(3-fluoro-4-sulfamoylbenzyl)-1H-pyrazol-1-yl) thiazole-4-carboxylic acid, 2-(3-(3-benzamido-4-fluorophenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(6-fluoro-3',5'-dimethoxy-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(4-fluoro-3-(2-oxopyrrolidin-1-yl) phenyl)-4-(3-fluoro-4-sulfamoylbenzyl)-1H-pyrazol-1-yl) thiazole-4-carboxylic acid, 2-(5-(cyclopropylmethyl)-3-(3-(2,3-dihydro-1H-inden-5-yl)-4-fluorophenyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3',5',6-trifluoro-[1,1'-biphenyl]-3-yl)-1H-pyrazol-1-yl) thiazole-4-carboxylic acid, 2-(5-(cyclopropylmethyl)-3-(3',5'-dichloro-6-fluoro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(4-fluoro-3-(6-isopropyl-2,6-diazaspiro[3.3] heptan-2-yl) phenyl)-4-(3-fluoro-4-sulfamoylbenzyl)-1H-pyrazol-1-yl) thiazole-4-carboxylic acid, 2-(5-(cyclopropylmethyl)-3-(4-fluoro-3-(1H-imidazol-2-yl) phenyl)-4-(3-fluoro-4-sulfamoylbenzyl)-1H-pyrazol-1-yl) thiazole-4-carboxylic acid, 2-(3-(3-(1H-benzo[d] imidazol-2-yl)-4-fluorophenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(4-fluoro-3-(2-methyl-1H-imidazol-5-yl) phenyl)-4-(3-fluoro-4-sulfamoylbenzyl)-1H-pyrazol-1-yl) thiazole-4-carboxylic acid, 2-(5-(cyclopropylmethyl)-3-(4-fluoro-3-((5-methylthiophen-2-yl) ethynyl) phenyl)-4-(3-fluoro-4-sulfamoylbenzyl)-1H-pyrazol-1-yl) thiazole-4-carboxamide, 2-(3-(4'-chloro-3'-fluoro-[1,r-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4'-methoxy-3 '-methyl-[1,1'-biphenyl]-3-yl)-1H-pyrazol-1-yl) thiazole-4-carboxylic acid, 2-(3-(4'-chloro-[1, 1'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(3'-fluoro-4'-methyl-[1,1'-biphenyl]-3-yl)-4-(3-fluoro-4-sulfamoylbenzyl)-1H-pyrazol-1-yl) thiazole-4-carboxylic acid, 2-(3-(4'-(tert-butyl)-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4'-isopropyl-[11,1'-biphenyl]-3-yl)-1H-pyrazol-1-yl) thiazole-4-carboxylic acid, 2-(3-(3'-chloro-4'-methoxy-[1,l'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3 '-isopropyl-[1,1'-biphenyl]-3-yl)-1H-pyrazol-1-yl) thiazole-4-carboxylic acid, 2-(5-(cyclopropylmethyl)-4-(3-fluoro-4-sulfamoylbenzyl)-3-(3-(5,6,7,8-tetrahydronaphthalen-2-yl) phenyl)-1H-pyrazol-1-yl) thiazole-4-carboxylic acid, 2-(3-(3'-chloro-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(3-(4'-cyano-[1,l'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(3',5-difluoro-[1,1'-biphenyl]-3-yl)-4-(3-fluoro-4-sulfamoylbenzyl)-1H-pyrazol-1-yl) thiazole4-carboxylic acid, 2-(5-(cyclopropylmethyl)-3-(4'-(dimethylamino)-[1,l'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(3'-ethyl-4'-methoxy-[1,1'-biphenyl]-3-yl)-4-(3-fluoro-4-sulfamoylbenzyl)-1H-pyrazol-1-yl) thiazole-4-carboxylic acid, 2-(3-(4'-cyclopropyl-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(3-(4'-cyclobutyl-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(3-(4'-chloro-6-fluoro-3'-methyl-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(3'-ethyl-6-fluoro-4'-methoxy-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4-(2,2,2-trifluoroethyl)-[1,1'-biphenyl]-3-yl)-1H-pyrazol-1-yl) thiazole-4-carboxylic acid, 2-(3-(3-(tert-butylcarbamoyl) phenyl)-5-(cyclopropylmethyl)-4-(4-sulfamoylbenzyl)-1H-pyrazol-1-yl) thiazole-4-carboxylic acid, 2-(3-(3-(1H-benzo[d] imidazol-2-yl) phenyl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(4'-(dimethylamino)-6-fluoro-[1,1'-biphenyl]-3-yl)-4-(3-fluoro-4-sulfamoylbenzyl)-1H-pyrazol-1-yl) thiazole-4-carboxylic acid, 2-(3-(3'-chloro-6-fluoro-4'-methoxy-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(3-(3'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(3-(4'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(3'-(dimethylamino)-6-fluoro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(4',6-difluoro-3'-methyl-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(3',6-difluoro-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(3-(4,5-dihydrofuran-2-yl)-4-fluorophenyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4'-methyl-[1,1'-biphenyl]-3-yl)-1H-pyrazol-1-yl) thiazole-4-carboxylic acid, 2-(5-(cyclopropylmethyl)-3-(6-fluoro-3'-isopropyl-[1,1'-biphenyl]-3-yl)-4-(3-fluoro-4-sulfamoylbenzyl)-1H-pyrazol-1-yl) thiazole-4-carboxylic acid, 2-(3-(3'-cyano-6-fluoro-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(3-(4'-cyano-6-fluoro-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(4-fluoro-3-(2-oxopyrrolidin-1-yl) phenyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3-(5-methylpyridin-2-yl) phenyl)-1H-pyrazol-1-yl) thiazole-4-carboxylic acid, 2-(5-(cyclopropylmethyl)-4-(3-fluoro-4-sulfamoylbenzyl)-3-(3-(6-methylpyridin-3-yl) phenyl)-1H-pyrazol-1-yl) thiazole-4-carboxylic acid, 2-(5-(2-cyclopropylethyl)-4-(3-fluoro-4-sulfamoylbenzyl)-3-(4'-(perfluoroethyl)-[1,1'-biphenyl]-3-yl)-1H-pyrazol-1-yl) thiazole-4-carboxylic acid, 2-(5-(2-cyclopropylethyl)-4-(3-fluoro-4-sulfamoylbenzyl)-3-(4'-isopropyl-[1,1'-biphenyl]-3-yl)-1H-pyrazol-1-yl) thiazole-4-carboxylic acid, 2-(5-(2-cyclopropylethyl)-4-(3-fluoro-4-sulfamoylbenzyl)-3-(4'-isobutyl-[1,1'-biphenyl]-3-yl)-1H-pyrazol-1-yl) thiazole-4-carboxylic acid, 2-(5-(cyclopropylmethyl)-4-(3-fluoro-4-sulfamoylbenzyl)-3-(4'-(5-methylthiophen-2-yl)-[1,1'-biphenyl]-3-yl)-1H-pyrazol-1-yl) thiazole-4-carboxylic acid, 2-(5-(cyclopropylmethyl)-3-(6-fluoro-4'-(5-methylthiophen-2-yl)-[1,1'-biphenyl]-3-yl)-4-(3-fluoro-4-sulfamoylbenzyl)-1H-pyrazol-1-yl) thiazole-4-carboxylic acid, 2-[5-(cyclopropylmethyl)-4-[(3-fluoro-4-sulfamoylphenyl) methyl]-3-[5-(4-isopropylphenyl) pyridin-3-yl] pyrazol-1-yl]-1,3-thiazole-4-carboxylic acid, 2-[5-(cyclopropylmethyl)-4-[(3-fluoro-4-sulfamoylphenyl) methyl]-3-[6-(4-isopropylphenyl) pyridin-2-yl] pyrazol-1-yl]-1,3-thiazole-4-carboxylic acid, 2-{3-[3-(4-cyclopropyl-3-fluorophenyl)-4-fluorophenyl]-5-(cyclopropyhnethyl)-4-[(3-fluoro-4-sulfamoylphenyl) methyl] pyrazol-1-yl}-1,3-thiazole-4-carboxylic acid, 2-[5-(cyclopropylmethyl)-3-[4-fluoro-3-(4-isopropyl-3-methylphenyl) phenyl]-4-[(3-fluoro-4-sulfamoylphenyl) methyl] pyrazol-1-yl]-1,3-thiazole-4-carboxylic acid, 2-[5-(cyclopropylmethyl)-4-[(3-fluoro-4-sulfamoylphenyl) methyl]-3-[3-(2-methylpyrimidin-5-yl) phenyl] pyrazol-1-yl]-1,3-thiazole-4-carboxylic acid, 2-[5-(cyclopropylmethyl)-4-[(3-fluoro-4-sulfamoylphenyl) methyl]-3-[3-(5-isopropyl-1,3-thiazol-2-yl) phenyl] pyrazol-1-yl]-1,3-thiazole-4-carboxylic acid, 2-[5-(cyclopropylmethyl)-4-[(3-fluoro-4-sulfamoylphenyl) methyl]-3-[3-(5-isopropylpyrimidin-2-yl) phenyl] pyrazol-1-yl]-1,3-thiazole-4-carboxylic acid, 2-[5-(cyclopropylmethyl)-4-[(3-fluoro-4-sulfamoylphenyl) methyl]-3-[3-(5-methylpyrimidin-2-yl) phenyl] pyrazol-1-yl]-1,3-thiazole-4-carboxylicacid, 2-[5-(cyclopropylmethyl)-4-[(3-fluoro-4-sulfamoylphenyl) methyl]-3-[3-(5-isopropylpyridin-2-yl) phenyl] pyrazol-1-yl]-1,3-thiazole-4-carboxylicacid, 2-(5-(cyclopropylmethyl)-4-(3-fluoro-4-sulfamoylbenzyl)-3-(4'-(trifluoromethyl)-[1,1'-biphenyl]-3-yl)-1H-pyrazol-1-yl) thiazole-4-carboxylic acid, 2-(5-(cyclopropylmethyl)-3-(3-(2,3-dihydro-1H-inden-5-yl) phenyl)-4-(3-fluoro-4-sulfamoylbenzyl)-1H-pyrazol-1-yl) thiazole-4-carboxylic acid, 2-(3-(3-(1H-benzo[d] imidazol-2-yl) phenyl)-5-(cyclopropylmethyl)-4-(3-fluoro-4-sulfamoylbenzyl)-1H-pyrazol-1-yl) thiazole-4-carboxylic acid, 2-(3-(4'-cyclopropyl-[1,1'-biphenyl]-3-yl)-5-(cyclopropylmethyl)-4-(3-fluoro-4-sulfamoylbenzyl)-1H-pyrazol-1-yl) thiazole-4-carboxylic acid, 2-(5-(cyclopropylmethyl)-3-(3'-ethyl-6-fluoro-4'-methoxy-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4'-(perfluoroethyl)-[1,1'-biphenyl]-3-yl)-1H-pyrazol-1-yl) thiazole-4-carboxylic acid, 2-(5-(cyclopropylmethyl)-3-(6-fluoro-4'-(perfluoroethyl)-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(4'-isobutyl-[1,1'-biphenyl]-3-yl)-1H-pyrazol-1-yl) thiazole-4-carboxylic acid, 2-(5-(cyclopropylmethyl)-3-(6-fluoro-4'-isobutyl-[1,1'-biphenyl]-3-yl)-4-(3-fluoro-4-sulfamoylbenzyl)-1H-pyrazol-1-yl) thiazole-4-carboxylic acid), 2-(5-(cyclopropylmethyl)-4-(3-fluoro-4-sulfamoylbenzyl)-3-(4'-hydroxy-3'-methyl-[1,1'-biphenyl]-3-yl)-1H-pyrazol-1-yl) thiazole-4-carboxylic acid, 2-(5-(cyclopropylmethyl)-3-(3'-fluoro-4'-hydroxy-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-3-(3'-fluoro-4'-isopropyl-[1,1'-biphenyl]-3-yl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(6-((5-methylthiophen-2-yl) ethynyl) pyridin-2-yl)-1H-pyrazol-1-yl) thiazole-4-carboxylic acid, 2-(5-(2-cyclopropylethyl)-4-(3-fluoro-4-sulfamoylbenzyl)-3-(3-((5-methylfuran-2-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(5-((5-methylthiophen-2-yl) ethynyl) thiophen-2-yl)-1H-pyrazol-1-yl) thiazole-4-carboxylic acid, 2-(5-(2-cyclopropylethyl)-4-(3-fluoro-4-sulfamoylbenzyl)-3-(3-((5-methylthiazol-2-yl) ethynyl) phenyl)-1H-pyrazol-1-yl) thiazole-4-carboxylic acid, 2-(5-(2-cyclopropylethyl)-4-(3-fluoro-4-sulfamoylbenzyl)-3-(3-((2-methylthiazol-5-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3-((2-methylthiazol-4-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(4-((5-methylthiophen-2-yl) ethynyl) thiophen-2-yl)-1H-pyrazol-1-yl) thiazole-4-carboxylic acid, 2-(5-(2-cyclopropylethyl)-3-(3-((2,5-dimethylthiophen-3-yl) ethynyl) phenyl)-4-(3-fluoro-4-sulfamoylbenzyl)-1H-pyrazol-1-yl) thiazole-4-carboxylic acid, 2-(5-(2-cyclopropylethyl)-4-(3-fluoro-4-sulfamoylbenzyl)-3-(3-((5-methylthiophen-3-yl) ethynyl) phenyl)-1H-pyrazol-1-yl) thiazole-4-carboxylic acid, 2-(5-(cyclopropylmethyl)-4-(3-fluoro-4-sulfamoylbenzyl)-3-(3-((5-methylthiophen-3-yl) ethynyl) phenyl)-1H-pyrazol-1-yl) thiazole-4-carboxylic acid, 2-(5-(cyclopropylmethyl)-3-(3-((2,5-dimethylthiophen-3-yl) ethynyl) phenyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3-(2-(5-methylthiophen-2-yl)-2-oxoethyl) phenyl)-1H-pyrazol-1-yl) thiazole-4-carboxylic acid, 2-(5-(2-cyclopropylethyl)-4-(3-fluoro-4-sulfamoylbenzyl)-3-(3-((2-methylthiazol-4-yl) ethynyl) phenyl)-1H-pyrazol-1-yl) thiazole-4-carboxylic acid, 2-(5-(2-cyclopropylethyl)-3-(3-((5-cyclopropylthiophen-2-yl) ethynyl) phenyl)-4-(3-fluoro-4-sulfamoylbenzyl)-1H-pyrazol-1-yl) thiazole-4-carboxylic acid, 2-(3-(3-((5-cyclobutylthiophen-2-yl) ethynyl) phenyl)-5-(cyclopropylmethyl)-4-(3-fluoro-4-sulfamoylbenzyl)-1H-pyrazol-1-yl) thiazole-4-carboxylic acid, 2-(3-(3-((5-cyclobutylthiophen-2-yl) ethynyl) phenyl)-5-(2-cyclopropylethyl)-4-(3-fluoro-4-sulfamoylbenzyl)-1H-pyrazol-1-yl) thiazole-4-carboxylic acid, 2-(5-(cyclopropylmethyl)-4-(3-fluoro-4-sulfamoylbenzyl)-3-(3-((5-methylthiophen-2-yl) ethynyl) phenyl)-1H-pyrazol-1-yl) oxazole-4-carboxylic acid, 2-(5-(3-cyclopropylpropyl)-4-(3-fluoro-4-sulfamoylbenzyl)-3-(3-((5-methylthiophen-2-yl) ethynyl) phenyl)-1H-pyrazol-1-yl) thiazole-4-carboxylic acid, 2-(5-(cyclopropylmethyl)-3-(4-fluoro-3-((5-methylthiophen-2-yl) ethynyl) phenyl)-4-(3-fluoro-4-sulfamoylbenzyl)-1H-pyrazol-1-yl) thiazole-4-carboxylic acid, 2-(5-(cyclopropylmethyl)-3-(6-fluoro-4'-methyl-[1,1'-biphenyl]-3-yl)-4-(4-sulfamoylbenzyl)-1H-pyrazol-1-yl) thiazole-4-carboxylic acid, 2-(5-(cyclopropylmethyl)-4-(2-fluoro-4-sulfamoylbenzyl)-3-(4'-methyl-[1,1'-biphenyl]-3-yl)-1H-pyrazol-1-yl) thiazole-4-carboxylic acid, 2-(3-(3-(cyclopentylethynyl)-4-fluorophenyl)-5-(cyclopropylmethyl)-4-(3-fluoro-4-sulfamoylbenzyl)-1H-pyrazol-1-yl) thiazole-4-carboxylic acid, or a pharmaceutically acceptable salt of any of the foregoing.

17. The method claim 16, wherein the patient has a mutation in AGXT, GPHPR, HOGA1, or a combination of any of the foregoing mutations.

18. The method of claim 16, wherein the compound of Formula I, or a pharmaceutically acceptable salt thereof, is administered as a monotherapy.

19. The method of claim 16, wherein the compound of Formula I, or a pharmaceutically acceptable salt thereof, is administered to the patient in combination with at least one additional active agent selected from Vitamin B-6, phosphate, citrate, stiripentol (DIACOMIT), freeze-dried live Oxalobacter formigenes (OXABACT), reloxaliase (ALLN-177), and RNAi.

* * * * *